US012162913B2

(12) United States Patent
Turberg et al.

(10) Patent No.: US 12,162,913 B2
(45) Date of Patent: Dec. 10, 2024

(54) *RHIPICEPHALUS* NICOTINIC ACETYLCHOLINE RECEPTOR AND PEST CONTROL ACTING THEREON

(71) Applicant: ELANCO ANIMAL HEALTH GMBH, Monheim am Rhein (DE)

(72) Inventors: Andreas Turberg, Haan (DE); Melania Akkose, Dormagen (DE); Miral Puinean, Abingdon (GB); Martin Williamson, Harpenden (GB)

(73) Assignee: Blanco Animal Health GmbH, Monheim am Rhein (DE)

( * ) Notice: Subject to any disclaimer, the term of this patent is extended or adjusted under 35 U.S.C. 154(b) by 1275 days.

(21) Appl. No.: 16/074,289

(22) PCT Filed: Jan. 25, 2017

(86) PCT No.: PCT/EP2017/051492
§ 371 (c)(1),
(2) Date: Jul. 31, 2018

(87) PCT Pub. No.: WO2017/133938
PCT Pub. Date: Aug. 10, 2017

(65) Prior Publication Data
US 2021/0221859 A1    Jul. 22, 2021

(30) Foreign Application Priority Data

Feb. 1, 2016 (EP) .................... 16153550

(51) Int. Cl.
| | | |
|---|---|---|
| *C07K 14/435* | (2006.01) | |
| *A01N 43/22* | (2006.01) | |
| *A01N 43/50* | (2006.01) | |
| *C07H 21/00* | (2006.01) | |
| *C12P 21/02* | (2006.01) | |
| *G01N 33/50* | (2006.01) | |
| *G01N 33/566* | (2006.01) | |

(52) U.S. Cl.
CPC ........ *C07K 14/43527* (2013.01); *A01N 43/22* (2013.01); *A01N 43/50* (2013.01); *C07H 21/00* (2013.01); *C12P 21/02* (2013.01); *G01N 33/5023* (2013.01); *G01N 33/566* (2013.01); *G01N 2333/70571* (2013.01)

(58) Field of Classification Search
CPC .. C07K 14/43527; A01N 43/22; A01N 43/50; C07H 21/00; C12P 21/02; G01N 33/5023; G01N 33/566; G01N 2333/70571
See application file for complete search history.

(56) References Cited

U.S. PATENT DOCUMENTS

| | | |
|---|---|---|
| 3,993,648 A | 11/1976 | Powell |
| 4,742,060 A | 5/1988 | Shiokawa et al. |
| 4,849,432 A | 7/1989 | Shiokawa et al. |
| 5,202,242 A | 4/1993 | Mynderse et al. |
| 5,571,901 A | 11/1996 | Boeck et al. |
| 5,631,155 A | 5/1997 | Turner et al. |
| 5,852,012 A | 12/1998 | Maienfisch et al. |

FOREIGN PATENT DOCUMENTS

| | | |
|---|---|---|
| EP | 0376279 B1 | 5/1993 |
| EP | 0302389 B1 | 12/1993 |
| EP | 0649845 A1 | 4/1995 |
| EP | 1621888 A1 | 2/2006 |
| WO | 2005036966 A1 | 4/2005 |
| WO | 2005107468 A1 | 11/2005 |
| WO | 2006061146 A1 | 6/2006 |
| WO | 2006061147 A1 | 6/2006 |
| WO | 2008003738 A1 | 1/2008 |
| WO | 2010099965 A2 | 9/2010 |
| WO | 2014122083 A1 | 8/2014 |

OTHER PUBLICATIONS

Bowie et al (Science, 1990, 257:1306-1310).*
Burgess et al (J. of Cell Bio. 111:2129-2138, 1990).*
Lazar et al. (Molecular and Cellular Biology, 1988, 8:1247-1252).*
Bork (Genome Research, 2000, 10:398-400).*
Erdmanis; Laura et al., "Association of Neonicotinoid Insensitivity with a Conserved Residue in the Loop D Binding Region of the Tick Nicotinic Acetylcholine Receptor", Biochemistry, May 28, 2012, 51, 4627-4629.
Grauso; M., "Novel Putative Nicotinic Acetylcholine Receptor Subunit Genes, Dα5, Dα6 and Dα7, in *Drosophila melanogaster* Identify a New and Highly Conserved Target of Adenosine Deaminase Acting on RNA-Mediated A-to-I pre-mRNA Editing", Genetics Society of America, Jan. 29, 2002, 160/4, 1519-1533.
Hosie; A.M., "Alternative Splicing of a *Drosophila* Gaba Receptor Subunit Gene Identifies Determinants of Agonist Potency", Pergamon, 2001, 102/3, 709-714.
Kita; Tomo, "Expression pattern and function of alternative splice variants of glutamate-gated chloride channel in the housefly *Musca domestica*", Insect Biochemistry and Molecular Biology, 2014, 45, 1-10.
Matsuda; Kazuhiko, "Diverse Actions and Target-Site Selectivity of Neonicotinoids: Structural Insights", Molecular Pharmacology, Mar. 25, 2009, 76/1, 1-10.
Puinean; Alin M., "A nicotinic acetylcholine receptor transmembrane point mutation (G275E) associated with resistance to spinosad in Frankliniella occidentalis", Journal of Neurochemistry, 2012, 124/5, 590-601.
Rinkevich; F.D., "Transcriptional diversity and allelic variation in nicotinic acetycholine receptor subunits of the red flour beetle, *Tribolium castaneum*", Insect Molecular Biology, 2009, 18/2, 233-242.

(Continued)

*Primary Examiner* — Robert A Zeman
(74) *Attorney, Agent, or Firm* — McBee Moore & Vanik IP, LLC

(57) ABSTRACT

Provided are *Rhipicephalus* nicotinic acetylcholine receptors and nucleic acid sequences encoding the same. Provided are furthermore a method of identifying a compound capable of modulating activity of a *Rhipicephalus* nACh receptor as well as a compound effective in modulating activity of a *Rhipicephalus* nicotinic acetylcholine receptor.

3 Claims, 12 Drawing Sheets

Specification includes a Sequence Listing.

(56) References Cited

OTHER PUBLICATIONS

Shimomura; Masaru, "Effects of mutations of a glutamine residue in loop D of the x7 nicotine acetylcholine receptor on agonist profiles for neonicotinoid insecticides and related ligands", British Journal of Pharmacology, 2002, 137/2, 162-169.
Tomizawa; Motohiro, "Neonicotinoid Insecticide Toxicology: Mechanisms of Selective Action", Annual Reviews Pharmacology Toxicology, 2005, 45, 247-268.
Database UniProt [online] Mar. 6, 2013 (Mar. 6, 2013), "Putative acetylcholine receptor from Rhipicephalus pulchellus", XP002768259, retrieved from EBI accession No. UniProt:L7MKP0 Database accession No. L7MKP0.
Database UniProt [online] Jan. 22, 2014 (Jan. 22, 2014), "Putative acetylcholine receptor from *Ixodes ricinus* (Common tick)", XP002771812, retrieved from EBI accession No. UniProt: V5H4U2 Database accession No. V5H4U2.
Database UniProt [online] Jan. 22, 2014 (Jan. 22, 2014), "Putative acetylcholine receptor from *Ixodes ricinus* (Common tick)", XP002771813, retrieved from EBI accession No. UniProt: V5HYY9 Database accession No. V5HYY9.
Database UniProt [Online], Accession No. L7MI75, Mar. 6, 2013.
Liu, B. et al., J. Am. Chem. Soc., vol. 126, 2004, pp. 4076-4077. Abstract only.
Lees Kristin et al: "Functional characterisation of a nicotinic acetylcholine receptor [alpha] subunit from the brown dog tick, *Rhipicephalus sanguineus*", International Journal of Parasitology, Pergamon Press, GB, vol. 44, No. 1, Dec. 1, 2013 (Dec. 1, 2013), pp. 75-81, XP028808655, ISSN: 0020-7519, DOI: 10.1016/J.IJPARA. 2013.11.002. Abstract only.
K. Lees et al: "Transcriptome analysis of the synganglion from the brown dog tick, *Rhipicephalus sanguineus* : Tick synganglion transcriptome", Insect Molecular Biology, vol. 19, No. 3, Jun. 7, 2010 (Jun. 7, 2010), GB, pp. 273-282, XP055388641, ISSN: 0962-1075, DOI: 10.1111/j.1365-2583.2009.00968.x. Abstract only.
Snyder et al., "Preliminary study on the acaricidal efficacy of spinosad administered orally to dogs infested with the brown dog tick, *Rhipicephalus sanguineus* (Latreille, 1806) (Acari: Ixodidae)", Veterinary Parasitology., vol. 166, No. 1-2, Dec. 1, 2009, NL, pp. 131-135, XP055384316, ISSN: 0304-4017, DOI: 10.1016/j.vetpar. 2009.07.046, Category: A.
Jones et al., "Diversity of insect nicotinic acetylcholine receptor subunits.", Advances in Experimental Medicine and Biology United States 2010, vol. 683, Dec. 31, 2010, pp. 25-43, XP055355468, DOI: NLM20737786, Category:A.

\* cited by examiner

| nAChR group | Subunit | Observations |
|---|---|---|
| Dα1 | Rmicro_nAChRα1 | 98.6% similar to *R. sanguineus* nAChRα1 |
| | Rmicro_nAChRα1.2 | Clusters with insect α1s |
| Dα3 | Rmicro_nAChRα3 | Distinct branch with *I. scapularis* α3 (77.3% similar) |
| Dα5-7 | Rmicro_nAChRα5 | Long 5' and 3' end UTRs |
| | Rmicro_nAChRα6 | 69% similar to *D. melanogaster* nAChRα6 |

| nAChR group | Subunit | Observations |
|---|---|---|
| Dβ2 | Rmicro_nAChRα8 | Similar to other insect α8 sequences (~60%) |
| Dβ1 | Rmicro_nAChRβ1 | Distinct branch with *I. scapularis* α3 (88% similar) |
| Divergent subunits | Rmicro_nAChRβ3.1 | Low sequence identity with other nAChRs. |
| | Rmicro_nAChRβ3.2 | |
| | Rmicro_nAChRβ3.3 | |
| | Rmicro_nAChRβ3.4 | |

Fig. 1

```
ACCTCCACCATGTTTCTTCGGGGACTGATTCCAGCCATCGTGTACGTGTGCCTGTGGAC
GGCCTGCCTCCTCTCCACAAACCTCGTGGCCGAGGTGGACGAGACGTGGTCGGCTCGCG
AGAACGACTCCTCGTCGCCGCCGCCGCCACTGAGTCACGAGAAGCGGCTGATGGAC
TCGCTGCTGCGCCACTACGACGCCAGCGTGAGGCCCGTCAAGAACTCCTCGGAGCCCGT
CATCATTCGGCTGGGCATCACGCTCACGCAGATATTCGACCTGGACGAGAAGAATCAAG
TCCTAACAACCATCGTTTGGCTTGACCAGGAATGGTTCGACGAGTACCTCACTTGGGAC
CCGTTGGAGTTTGGAAACTTCAGCAACCTCAGGCTGCCCTGCCACAAGATTTGGCTGCC
TGACATCGTTCTCTACAACAACGCGGACGACTACACGCGGGGCTACTTCCAGACGCGCG
CCATGATCGACCCCCAGGGCCGAGTGTTCTGGCCGCCACCCACCAAGTTTCGCAGCACC
TGCCCGGTGGACGTAACGTACTTCCCTTTCGACGACCAGGTCTGCACAATGAAGTTCGG
TTCTTGGATCTATGACGGGCTACAAGTGGACATCCAGAACCGGACATCCGAGGTTGACC
TGGTCAATTACATGCCCAACGGCGAGTGGGAGCTGCTTGAGGCACGCATGGTGCGCAAC
GTGGTCTACTACCCTTGCTGTCCAGACCAGCCGTTCCCGGACATCACCGTGGTCTTGGT
CATGAGGCGCAAGACGCTCTACTACATGTACAACGTGGTCCTGCCCTGCATCATGATGT
CTGTGCTGACTCTGCTCGTCTTCTGCCTACCGCCGGACTCGGGCGAGAAGATCGCGCTC
GGCGTCACAGTGCTGCTAGCATTCTCCGTGTTCATGCTGGCCATAGCGGAGAAGATGCC
CGAGACATCGGAGTCCATACCCTTACTGGGAATATACCTGACGGCCGTGATGGCCATCA
CGTCCATCTCGGTCGTCATGACCGTGATCGTCCTCAACTTCCACTACCGCGGCCCCAGC
CGGAAAGAAGTGCCAGCGTGGCTCCGCCGTCTCCTGCTCAACAAGTCATCCTCCAGTCG
TGGTTGGTTCTCGAAGCCGGCGCGCCGCAAGACCGTCGGCGACAATCACGTGCACTTCT
ACGACTTGCCATCGCGCACAGCAGCCTCCAAGGACCGCTCAGACCTGGACGACGACGTA
GACGGCAGCAGAAGACCTGCGGCCGACGACACCTTCCGGCTCGTCGTGGACAGCGTCGT
GATCGGCAGCGAAGACCGCTACACTCGCGGCGAGTACGCCGAGCACTCCGCGAGCAACG
AGTCCCCGAGTCCCGTCCTCCACGGCGACATGTCGCGGAACAATGCCTCCGGGTCGGCC
AGGCACCGCCGCTGTCGCGCTGGTGCCGCTAGTGGCGGATCCACTAAGCGCGTGCAGGA
AGAAGTGCTGCGGACTTTGCGGTACCTGATGGAGAAACAGCAGCGCGAGGAGCACCTCA
CCCGGACTGTGAACGAGTGGAGACAGATGGCTCTCGTGATAGATCGCACCTTGTTCTGG
TTCTTTCTGATCATCACAGCCGTGTCATCCRTCTGCTTCCTAGTCGTCATACCCATACA
GAGGCGGGGACTGTGACTGTGACTTGGGCGGAGTTGTGAGCAACTCTGCATTGCCATGA
CGTGCTAAAACACTTAAAGAGAGAGGCAGACGGGAGAGATCCGAGGGATTCATGTGTCA
CCA
```

Fig. 2

MFLRGLIPAIVYVCLWTACLLSTNLVAEVDETWSARENDSSSPPPPPLSHEKR

LMDSLLRHYDASVRPVKNSSEPVIIRLGITLTQIFDLDEKNQVLTTI<u>VWLDQE</u>
<span style="margin-left: auto;">Loop D</span>

<u>WFDEYLTWDPLEFGNFSNLRLPCHKIWLP</u><u>DIVLYNNAD</u>DYTRGYFQ<u>TRAMI</u>
Loop D                                        Loop A           Loop E <u>DPQGRVFWP</u>PPTKFRSTCPVDVTYFPFDDQVCTMKF<u>GSWIYD</u>GLQVDIQN<u>R</u>
Loop E                                   Loop B         Loop F <u>TSEVDL</u>VNYMPNGEWELLEARMVRNVVY<u>YPCCPDQP</u>FPDITVVLMRRKT
Loop F                              Loop C <u>LYYMYNVVLPCIMMSVLTLLVFCL</u>PPDSGEKIA<u>LGVTVLLAFSVFMLAIAEK</u>
TM1                                          TM2

M<u>P</u>ETSESIPLLGI<u>YLTAVMAITSISVVMTVIVL</u>NFHYRGPSRKEVPAWLRRLL
TM2             TM3

LNKSSSSRGWFSKPARRKTVGDNHVHFYDLPSRTAASKDRSDLDDDVDGSR

RPAADDTFRLVVDSVVIGSEDRYTRGEYAEHSASNESPSPVLHGDMSRNNAS

GSARHRRCRAGAASGGSTKRVQEEVLRTLRYLMEKQQREEHLTRTVNEWR

QMALVIDRT<u>LFWFFLIITAVSSVCFLV</u>VIPIQRRGL
TM4

Fig. 3

ACCACGACGCGGACCATGCGCCCCGGACGCCTGTCTGTGCCGCTGCAGCTAGGCTTCTGCGCCAA
CCTGCTGTGGATCGCCGTGCTGCTCACCGCGCCTCAGGACTCTGAACAAGGCGCGCACGAGCGGC
GGCTTCTGGCAGACCTGCTGGCCAACTACAACACCCTGGAGCGGCCCGTGCTCAACGAGTCGGAG
CCGCTCATCCTCAGCTTCGGGCTCACACTGCAGCAGATCATAGACGTCGACGAAAGAATCAGCT
AATTATTACAAATATCTGGTTAACATTGGATTGGATAGATGTGAATCTACGTTGGAACCCAAAAG
ACTACGGCGGAGTGCAGGACCTGCGTATTCCGCCAAACAAAATTTGGAAGCCTGACGTGCTCATG
TACAACAGCGCGGACGAAAAGTTCGACGGCACGTACCCGACCAACGTGGTCGTGCGGAGCAACGG
CAGTTGCAACTACATCCCTCCTGGCATCTTTAAGAGCACGTGCAAGATCGACATTACGTGGTTCC
CTTTTGACGATCAGAAGTGCGACCTGAAGTTCGGCTCCTGGACCTATCACGGTTATCAGCTGGAC
CTTCGTGTCAACAGTGAGGAAGGCGGGGATCTGACTACCTACATTCCCAATGGCGAGTGGGACCT
GATAGGCGTGCCGGGAGTGCGCAACGTTCGCGAGTATGCCTGCTGTCCGGAGCCGTACATCGACA
TCACGTACACCATCCACATCCGGCGGCGCACGCTCTACTACGGCTTCAACCTCATCATTCCCTGC
GTGCTCATCTCGTCCATGACTCTGCTCGGTTTCACGCTGCCCCCGACACCGGAGAGAGGCTCAC
CCTGGGTGTAACCATTTTGCTGTCCCTGACGGTATTCATGCTCCAGCTCGCCGAGACCATGCCTC
CGACGTCCGATGCTGTCTCCATAATAGGAACTTATTTTGCCTGCATCATGATCATGGTTGCCTTT
TCGGTGGTCATGACCGTGGTGGTCCTGAACTATCATCACAGAAATCAAGAGACGACCGAAATGCC
TGCTTTGATTCGCACGGTGTTCCTGGTGTGGCTCCCGTGGCTTCTGCGCATGGAGCCTCCGGGCC
AGAAGGCGAACAGGCGCAGCCTCTTCCTCAACAGCAAGATGAAAGAGCTCGAGCTGAAGGAGCGC
TCATCGCGGAGTCTGCTGGCCAACGTGCTGGACATCGACGACGACTTCCGCACGGCCAACAGCGC
CGCCGCCGCCGACTGCCACGGGTCTCGGACCCCGTTCCTGGGCGGTGGCGGCGGGGCGTCCA
CGGTGCACGCTTGCGTCCACTCGTCGCGTGAACTGAACTTGATCTTGCGCGAGCTGCGCTTCATC
ACGAGCCGCATGCGCAAGGACGAGCAAGAGCGGGAGGTCGTTGGCGAGTGGAAGTTCGCGGCCAT
GGTCGTCGACCGCTGCTGCCTCATCATCTTCTCCCTGTTCACCATCATCTCCACCTGCGCCTGCC
TCTTCTCGGCGCCCCATCTGGTCGCCTAGCGCACCCTGCT

Fig. 4

MRPGRLSVPLQLGFCANLLWIAVLLTAPQDSEQGAHER

RLLADLLANYNTLERPVLNESEPLILSFGLTLQQIIDV

DEKNQLIITN <u>IWLTLDWI</u> DVNLRWNPKDYGGVQDLRIP
                 *Loop D*

PNKIWKP <u>DVLMYNSAD</u> EKFDGTYP <u>TNVVRSNGSCNYI</u>
              *Loop A*                    *Loop E*

PPGIFKSTCKIDITWFPFDDQKCDLKF <u>GSWTYH</u> GYQLD
                                      *Loop B*

LRV <u>NSEEGGDL</u> TTYIPNGEWDLIGVPGVRNVRE <u>YACCP</u>
      *Loop F*                                      *Loop C*

<u>EP</u> YIDITYTIHIRRRT ⟦LYYGFNLIIPCVLISSMTLLGF⟧
*Loop C*                                              *TM1*

⟦TL⟧ PPDTGERLT ⟦LGVTILLSLTVFMLQLAETMP⟧ PTSDAV
*TM1*                                      *TM2*

SIIGT ⟦YFACIMIMVAFSVVMTVVL⟧ NYHHRNQETTEMP
              *TM3*

ALIRTVFLVWLPWLLMEPPGQKANRRSLFLNSKMKEL

ELKERSSRSLLANVLDIDDDFRTANSAAAADCHGSRT

PFLGGGGASTVHACVHSSRELNLILRELRFITSRMRK

DEQEREVVGEWKFAAMVVDRCCLIIFSLFTIISTCACL

FSAPHLVA

Fig. 5

| Subunit combination (in pCR4) | Functionality |
|---|---|
| Rmα1:Rmα1.2:Rmα3:Rmβ1 | - |
| Rmα5 | Yes |
| Rmα6 | Yes |
| Rmβ3.1 | - |
| Rmβ3.2 | - |
| Rmβ3.4 | - |
| Rmβ3.1:Rmβ3.2:Rmβ3.4 | - |

| Subunit combination (in pGEMHE) | Functionality |
|---|---|
| Rmα1:Ratβ2 | Yes |
| Rmα3: Ratβ2 | - |
| Rmα1:Rmβ1 | - |
| Rmα6 | Yes |

Fig. 6

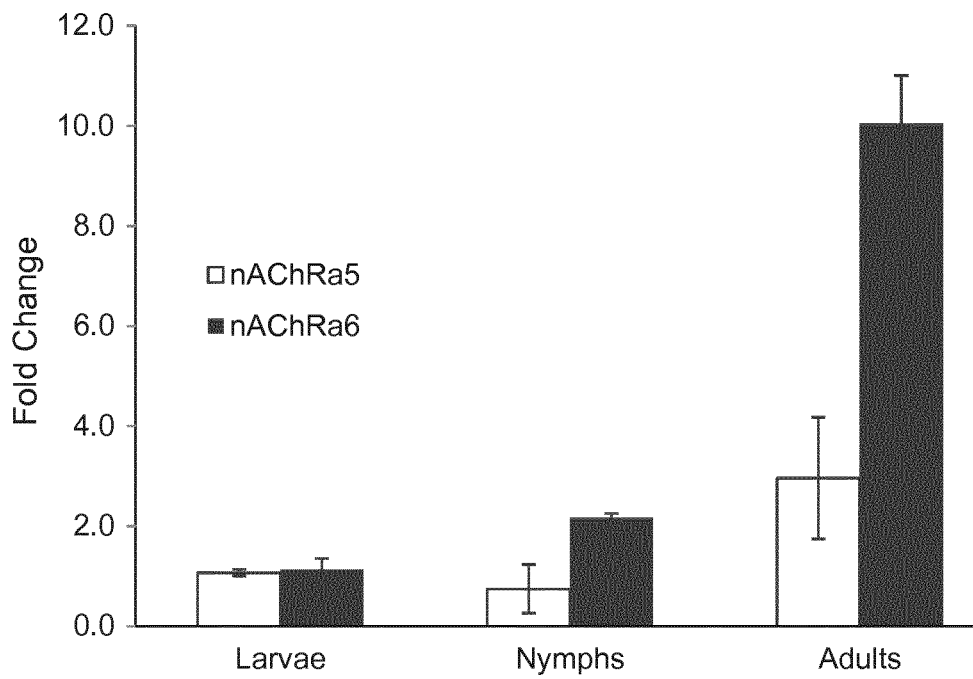

Fig. 7

```
ACATGGGGAAAGCCCGTCCGTCGCCTCGTCCGCGAGGACACGCTTGCCGCGCCGGGCGCGTCCC
TACTGTGCTGCCTCTTTTTCCTCCTGCAGCGCCCACATCACCACTTCGCCTCCAACCCTGCAAC
AGAGATACGCCTCTTCGTGGAGAGAACTTCTAGTCAACTCGCCGCACGCAAGTTTTCCTCCCTG
TGGATTGCTGCGCTGCGTGAAGCGAAACTTACAAAGAAAGTTTTTCGTTCCCCGCGCCTGTGGA
TTCCGATCGACGACGCTGGATCTTTTGTAGCGAAAGTTAGGAACATTAGTTTTGTCAACGAGGC
TCCCTCGAAGGCAGCATTTTTTTCTTCCTTAAAAAAGGGTGTATGAGGCGCGCTACTTAATTTT
TTTTTTTGTCTTCCTGAGTCGGTCTGGGCTTTCCGGAAATTATTTGTTCCTGCCTTGAACAGTT
CTTCGAGCAGTTCATAAGAAGTGTAAAATTAGCGCCACTTTCGTAAGAGGAACAGGAACCTTAA
GAAAAAAGAGATACCTGCAAGTAGAGTTAAAGCTCTCTAATCTAAGCATTCCTCCCCACAGAGA
AAAACGCGCAGTGTACTTGATACGCGCAGTAAACGCCTAGCAAGGTATATTGAGGGGCCTGCGT
CGGCAGCGAGAAGTTTACGCGCGGCCAACCACGAGCTTTACTGCGCAGAAAGAAAGAAAAGGGG
ACGGGACTGCGAAAGCCTAAAAGCTCAACCTAATCAAAGTAAAGCAGGTCGTTCAGATTGTCAT
TTTGTCGAGCTGAAGAAGCGACTTCGCTGCGTACTCGGCCTTAATCGTAGGACAGAAGGAGCAC
CCACATCTGACGCAGTGGTCGAAGGGGGAGACGGTACAGGAGACGTGGAAGTGAAAACAAAAAT
CGCGAAGGACAATGTCGAGCAAGTTGTCTTCGTTGTCAAAGGCGGTCGCCTCGCCGCGAAAACC
CGTAGTCTGCGTGTTGCAGAGATGGTCGATGTTGGGCGTCGAAACTTGAACAAAAGCAGGAGC
TGGCCGTTTCAATTGAACCTCCACCATGTTTCTTCGGGGACTGATTCCAGCCATCGTGTACGTG
TGCCTGTGGACGGCCTGCCTCCTCTCCACAAACCTCGTGGCCGAGGTGGACGAGACGTGGTCGG
CTCGCGAGAACGACTCCTCGTCGCCGCCGCCGCCACTGAGTCACGAGAAGCGGCTGATGGA
CTCGCTGCTGCGCCACTACGACGCCAGCGTGAGGCCCGTCAAGAACTCCTCGGAGCCCGTCATC
ATTCGGCTGGGCATCACGCTCACGCAGATATTCGACCTGGACGAGAAGAATCAAGTCCTAACAA
CCATCGTTTGGCTTGACCAGGAATGGTTCGACGAGTACCTCACTTGGGACCCGTTGGAGTTTGG
AAACTTCAGCAACCTCAGGCTGCCCTGCCACAAGATTTGGCTGCCTGACATCGTTCTCTACAAC
```

Fig. 8 (continued on next page)

```
AACGCGGACGACTACACGCGGGGCTACTTCCAGACGCGCGCCATGATCGACCCCCAGGGCCGAG
TGTTCTGGCCGCCACCCACCAAGTTTCGCAGCACCTGCCCGGTGGACGTAACGTACTTCCCTTT
CGACGACCAGGTCTGCACAATGAAGTTCGGTTCTTGGATCTATGACGGGCTACAAGTGGACATC
CAGAACCGGACATCCGAGGTTGACCTGGTCAATTACATGCCCAACGGCGAGTGGGAGCTGCTTG
AGGCACGCATGGTGCGCAACGTGGTCTACTACCCTTGCTGTCCAGACCAGCCGTTCCCGGACAT
CACCGTGGTCTTGGTCATGAGGCGCAAGACGCTCTACTACATGTACAACGTGGTCCTGCCCTGC
ATCATGATGTCTGTGCTGACTCTGCTCGTCTTCTGCCTACCGCCGGACTCGGGCGAGAAGATCG
CGCTCGGCGTCACAGTGCTGCTAGCATTCTCCGTGTTCATGCTGGCCATAGCGGAGAAGATGCC
CGAGACATCGGAGTCCATACCCTTACTGGGAATATACCTGACGGCCGTGATGGCCATCACGTCC
ATCTCGGTCGTCATGACCGTGATCGTCCTCAACTTCCACTACCGCGGCCCCAGCCGGAAAGAAG
TGCCAGCGTGGCTCCGCCGTCTCCTGCTCAACAAGTCATCCTCCAGTCGTGGTTGGTTCTCGAA
GCCGGCGCGCCGCAAGACCGTCGGCGACAATCACGTGCACTTCTACGACTTGCCATCGCGCACA
GCAGCCTCCAAGGACCGCTCAGACCTGGACGACGACGTAGACGGCAGCAGAAGACCTGCGGCCG
ACGACACCTTCCGGCTCGTCGTGGACAGCGTCGTGATCGGCAGCGAAGACCGCTACACTCGCGG
CGAGTACGCCGAGCACTCCGCGAGCAACGAGTCCCCGAGTCCCGTCCTCCACGGCGACATGTCG
CGGAACAATGCCTCCGGGTCGGCCAGGCACCGCCGCTGTCGCGCTGGTGCCGCTAGTGGCGGAT
CCACTAAGCGCGTGCAGGAAGAAGTGCTGCGGACTTTGCGGTACCTGATGGAGAAACAGCAGCG
CGAGGAGCACCTCACCCGGACTGTGAACGAGTGGAGACAGATGGCTCTCGTGATAGATCGCACC
TTGTTCTGGTTCTTTCTGATCATCACAGCCGTGTCATCCRTCTGCTTCCTAGTCGTCATACCCA
TACAGAGGCGGGGACTGTGACTGTGACTTGGGCGGAGTTGTGAGCAACTCTGCATTGCCATGAC
GTGCTAAAACACTTAAAGAGAGAGGCAGACGGGAGAGATCCGAGGGATTCATGTGTCACCATTT
TGACTAAACTCTGGTGGTATGGAGCCTGTATTCGTTTCGCCTAAATAATTGGTTTACAACTCTC
TAAAATACTAGCACATCGTAGGCGCGCTGAAGTTTAGTACTTCTCAAGAGTAAACGTTAGAAGG
CATCTGCAGCCTTTTTGATGTTAGAGACAAGTGTACACACAATATTGATAATCCTAGCCACGAA
TTCTTGCTATGTTCATCTCGGAGTTTGCTAAATATTCTTTAACAGCGCTAATATTGTCTAATTT
CTAGACAAGTTGCATCTATTGGGAAAATCAGAGGTGGAATTCACAAAGTATGTCACTTGTTACT
ATTCGTGATTATTGACCATCAAGCTTACATAATATTTCCAGCATATGTGTTGGTTGAAACTTCC
TTTAAATTCTTTAAACTAATATGATAATGAGTAAAGAAAGTTATAAGCCAAGTTTAAATCTCAC
CGAGGTGTATCGTACAAAACACCAATAAAATGCTGTATAATTAGTTTCGCTATCAAATGGTAAG
AACATTATTAGTCTTTGAAGATATGCGAGTCTTATTATGCAGTGTACACACATGCATCACCTTG
AGTGTTGTGATTTTGATTAGGCAAAATTAAAGGTCGAAACGGTGATCCAAGCAATTATGTTTCG
CATAATATCCTTGCGCCTCCTGTTGGAGTGTTTGTATATTTTTCTCCTTGGAAACAAGCTTGC
ATTCGTGCCAAAAGAGCCACGTTATTACAGATGTGCGTCCAAGAAAAGAGTGGGCAAATGAAGT
GTGTCCACGGAGCTTAATGAATGCAATTATTCGACTACAATAACGTCACTTTCACACTCACTTC
TTTGACGGATTGCGCGTTTTAAAAAGCGCGATTGTTCATAATGTCTTCGTCGAAACCGCTGTG
CTATATTTAGGTATTGTCAGGTTTGTCTTTGTTAGTGTGCCCTACCATCATGTACAAAACTGGT
CGAGAAGAATTCGAGGAGGTGCAGGCAAAAAATATATATTTCTTAGTCTGCAGCCAGTTTCTC
CTATAGATAACGAACCACTACTATGGTGCCTATGCTGTTCTAAAAATCTAACTTAGCGCAAACC
AGCACTCGCACGTTCTCAAGCGTCTGGCATTACTTTATTAAGGAGGGATTTCATTGAGTGCAAT
CACGACAGCTCCATCACCGCGAACTCACCATGTGTGTGATACAACAGACCGTTTAACTGCAGTG
CTACAGCATAACTTGTCATAAATGGGCCAAAATGAGTAACCAAATATTAGGTATAAAGTTGCGT
AGCTTTTCACGACCACTTTCGCAACACCACATTAAGTATATAGGCATGTGCGACACAGGCACAA
AAATCCCGGGAACATGACTCAATTCACAGGATTCACCTCTGAATTATTTTTTTCTTTGCATCT
```

Fig. 8 (continued on next page)

```
TAGACTGCATCTTCATTATTCAACCATCTTTAGGCTTGCATAGAAATTTCCCACGTATTTCCTG
CGACGGCAGTACTGAAAGTACGTACTAATCTTTAGACAAGTGCTCAGAGTAACACAAGCACATC
GTTGCTCAATACTACACTAATCATAGTATCTTCCGGTAGATGTATATCGTGCTAGTGACTTGTC
CATTGCTTGCCGCTGCTGTAGTAGTAATTTTACGCATCCAAAGTGCGATCATGTAGTTGCTTGC
AAGGCACGTGGATGATAAAATATACTACTACAGCGATCTACAGCGTTTGTGTCTTGTTTTTGTT
GTTGTTACGTTGTTGATTGGTGTGAGCGGTCGATGACGTAGCATTGTCATCACAAACAGCCTGT
TGAACGCGTATGGCATCTTTGCGTCGAGAATACCAGCAAAACTGAAACGGAGCGTGCATGGAGC
ATTTGCGACCAATTTACGACCCCTATTTGTATGTGATTTGATTAATAAAGTCTGTGCTCAGGGA
AGACAGAAATTTGGACGGCATAAAGCAGCCTCGGGAACCACTAGCAACGCACTTAAGCGTTTGT
TTTATAGAAAAATTTTCTTCTTTCGCTATATTGCGATCACTTGTTGTTGTTGGGCCTGCTTAAG
TTCTTTCAGATGCACCTATGCACAACCGTTCTTTTGATGCCCGAGTCATATCACTGCTCAGACC
GAAATGCGGACGAGGGCCTGAGCAGCGGTGTGACTTGAGCGCACGATTTCGTATTTTTGCACAG
AGATATTTCCTACTTAAGGCTTCCTTCTCAAATCCGACTGTGGATTTTGTGTTAGAGCGCAAAA
TTTGTTTGTCTCCATGCACGCGAGCTGCTTTAGCCTTACTTGTGTTTTGGGGCGAGAAAATCTG
TGTAGTTGTTTGTGCAATAAACGACCACTACAGGAAAAAAAAAAAAAAAAAAAAAAAAAAAAAA
A
```

Fig. 8 (continued from prev. page)

```
GAAGAGGCCCGCAGGCCCACCACTCGCGGCGTACCACGACGCGGACCATGCGCCCCGGACGCCT
GTCTGTGCCGCTGCAGCTAGGCTTCTGCGCCAACCTGCTGTGGATCGCCGTGCTGCTCACCGCG
CCTCAGGACTCTGAACAAGGCGCGCACGAGCGGCGGCTTCTGGCAGACCTGCTGGCCAACTACA
ACACCCTGGAGCGGCCCGTGCTCAACGAGTCGGAGCCGCTCATCCTCAGCTTCGGGCTCACACT
GCAGCAGATCATAGACGTCGACGAAAGAATCAGCTAATTATTACAAATATCTGGTTAACATTG
GATTGGATAGATGTGAATCTACGTTGGAACCCAAAAGACTACGGCGGAGTGCAGGACCTGCGTA
TTCCGCCAAACAAAATTTGGAAGCCTGACGTGCTCATGTACAACAGCGCGGACGAAAAGTTCGA
CGGCACGTACCCGACCAACGTGGTCGTGCGGAGCAACGGCAGTTGCAACTACATCCCTCCTGGC
ATCTTTAAGAGCACGTGCAAGATCGACATTACGTGGTTCCCTTTTGACGATCAGAAGTGCGACC
TGAAGTTCGGCTCCTGGACCTATCACGGTTATCAGCTGGACCTTCGTGTCAACAGTGAGGAAGG
CGGGGATCTGACTACCTACATTCCCAATGGCGAGTGGGACCTGATAGGCGTGCCGGGAGTGCGC
AACGTTCGCGAGTATGCCTGCTGTCCGGAGCCGTACATCGACATCACGTACACCATCCACATCC
GGCGGCGCACGCTCTACTACGGCTTCAACCTCATCATTCCCTGCGTGCTCATCTCGTCCATGAC
TCTGCTCGGTTTCACGCTGCCCCCCGACACCGGAGAGAGGCTCACCCTGGGTGTAACCATTTTG
CTGTCCCTGACGGTATTCATGCTCCAGCTCGCCGAGACCATGCCTCCGACGTCCGATGCTGTCT
CCATAATAGGAACTTATTTTGCCTGCATCATGATCATGGTTGCCTTTTCGGTGGTCATGACCGT
GGTGGTCCTGAACTATCATCACAGAAATCAAGAGACGACCGAAATGCCTGCTTTGATTCGCACG
GTGTTCCTGGTGTGGCTCCCGTGGCTTCTGCGCATGGAGCCTCCGGGCCAGAAGGCGAACAGGC
GCAGCCTCTTCCTCAACAGCAAGATGAAAGAGCTCGAGCTGAAGGAGCGCTCATCGCGGAGTCT
GCTGGCCAACGTGCTGGACATCGACGACGACTTCCGCACGGCCAACAGCGCCGCCGCCGCCGCC
GACTGCCACGGGTCTCGGACCCCGTTCCTGGGCGGTGGCGGCGGGGCGTCCACGGTGCACGCTT
GCGTCCACTCGTCGCGTGAACTGAACTTGATCTTGCGCGAGCTGCGCTTCATCACGAGCCGCAT
GCGCAAGGACGAGCAAGAGCGGGAGGTCGTTGGCGAGTGGAAGTTCGCGGCCATGGTCGTCGAC
CGCTGCTGCCTCATCATCTTCTCCCTGTTCACCATCATCTCCACCTGCGCCTGCCTCTTCTCGG
CGCCCCATCTGGTCGCCTAGCGCACCCTGCTYCTAGGACAGCACWTTAACCGCCACCAGCTTCC
```

Fig. 9 (continued on next page)

```
TCCACCGGCGGCCTTCCTCTCGGAGAGCTTGTTCGCTACGTTCTTTTGCGCAAGCCCTGCTTGT
TAGAGCGCGGCTTCYGAGATTGATTGCTGGAGCCAATCTCGAAGGCCACAATCTCACAGCGCGG
GCTCGTGTGCGAGAACGTGGCTCGTGAAGAGTTCCAGGTGACGCCCTTGTTGCAACAYCCCGTG
AAGTCCTGTCCACTTCCCCACGCCATCACGTGCGAAGAGATGCAGCGCGAAACACGTAYGACGC
GAAGACTTCGTACCGCACTGACCCTTACTGTGGGGAGGAGGAAGACACGTGGAGGTCGCAGGAG
CTAGTTTTTTTTTAAGTCTCAACTCATGTGCCAATCATGAGCCGCCACTTGTGCGAAAGCGTTG
GACCATCTCGGAGGATCTGGTAGCACCGTCCGAAGCTGGTGCCTTGGCCGTCGCTTTCATTCTA
TATAGGATAAAATAACTTCATGTATGGCTGCCAAACTGTTTGAAGGGTCAAGCGGACTTATCAA
CCGAGCCCAACGAAGGAAGTAAAGCACCGGGTCTTCCCTCTACGAGCTTCGTGATCGTGAGATG
CCCGCCATGATGCGACGCCACTYGTTACTTGCTTGACCACCGTCATGGACGGCTCGTCGGAGTA
GGATAAGCCACGCRCGCAACGTCATCTTGCCAGTCCTTTCTTTCGTCGGTAATGGTGCGTATG
AGTAAAAAAAAA
```

Fig. 9 (continued from prev. page)

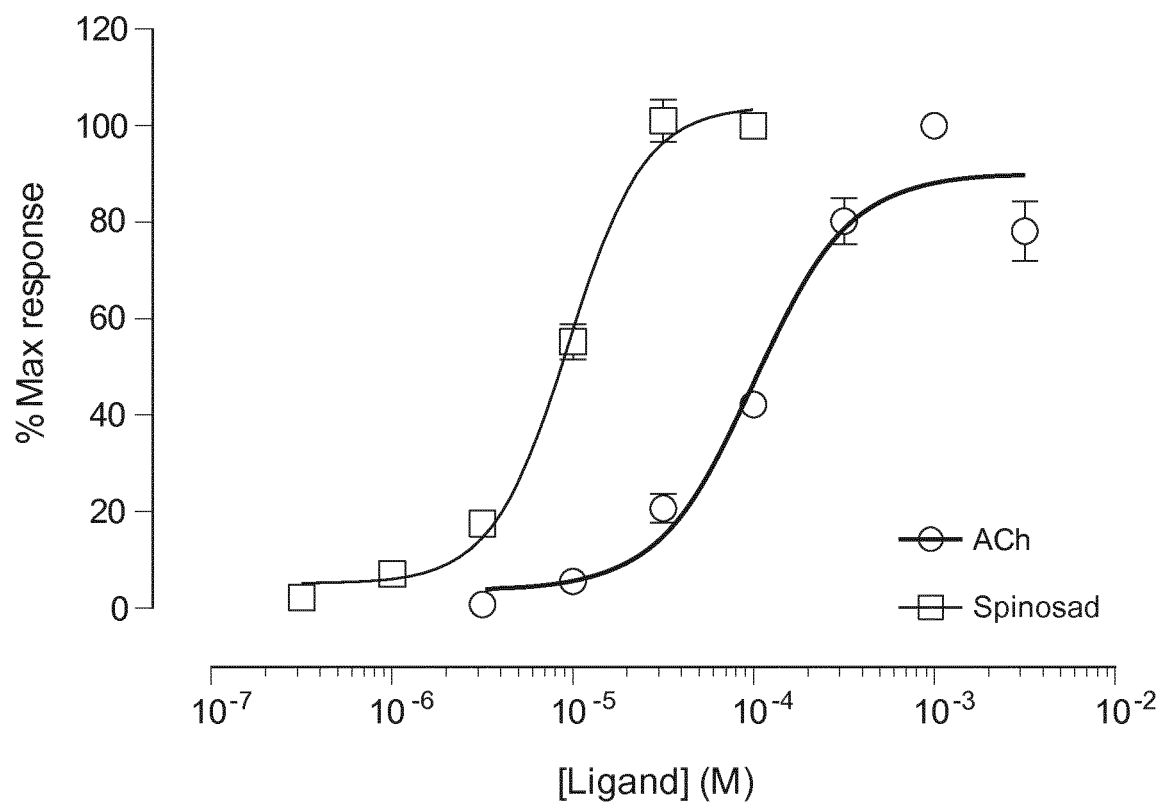

Fig. 10

```
ACCACGACGCGGACCATGCGCCCCGGACGCCTGTCTGTGCCGCTGCAGCTAGGCTTCTGCGCC
AACCTGCTGTGGATCGCCGTGCTGCTCACCGCGCCTCAGGACTCTGAACAAGGCGCGCACGAG
CGGCGGCTTCTGGCAGACCTGCTGGCCAACTACAACACCCTGGAGCGGCCCGTGCTCAACGAG
TCGGAGCCGCTCATCCTCAGCTTCGGGCTCACACTGCAGCAGATCATAGACGTCGACGAAAAG
AATCAAATAATAACAACAAACGTGTGGTTAAATCTGGATTGGATAGATGTGAATCTACGTTGG
AACCCAAAAGACTACGGCGGAGTGCAGGACCTGCGTATTCCGCCAAACAAATTTGGAAGCCT
GACGTGCTCATGTACAACAGCGCGGACGAAAGTTCGACGGCACGTACCCGACCAACGTGGTC
GTGCGGAGCAACGGCAGTTGCAACTACATCCTCCTGGCATCTTTAAGAGCACGTGCAAGATC
GACATTACGTGGTTCCCTTTTGACGATCAGAAGTGCGACCTGAAGTTCGGCTCCTGGACCTAT
CACGGTTATCAGCTGGACCTTCGTGTCAACAGTGAGGAAGGCGGGGATCTGACTACCTACATT
CCCAATGGCGAGTGGGACCTGATAGGCGTGCCGGGAGTGCGCAACGTTCGCGAGTATGCCTGC
TGTCCGGAGCCGTACATCGACATCACGTACACCATCCACATCCGGCGGCGCACGCTCTACTAC
GGCTTCAACCTCATCATTCCCTGCGTGCTCATCTCGTCCATGACTCTGCTCGGTTTCACGCTG
CCCCCCGACACCGGAGAGAGGCTCACCCTGGGTGTAACCATTTTGCTGTCCCTGACGGTATTC
ATGCTCCAGCTCGCCGAGACCATGCCTCCGACGTCCGATGCTGTCTCCATAATAGGAACTTAT
TTTGCCTGCATCATGATCATGGTTGCCTTTTCGGTGGTCATGACCGTGGTGGTCCTGAACTAT
CATCACAGAAATCAAGAGACGACCGAAATGCCTGCTTTGATTCGCACGGTGTTCCTGGTGTGG
CTCCCGTGGCTTCTGCGCATGGAGCCTCCGGGCCAGAAGGCGAACAGGCGCAGCCTCTTCCTC
AACAGCAAGATGAAAGAGCTCGAGCTGAAGGAGCGCTCATCGCGGAGTCTGCTGGCCAACGTG
CTGGACATCGACGACGACTTCCGCACGGCCAACAGCGCCGCCGCCGCCGACTGCCACGGG
TCTCGGACCCCGTTCCTGGGCGGTGGCGGCGGGGCGTCCACGGTGCACGCTTGCGTCCACTCG
TCGCGTGAACTGAACTTGATCTTGCGCGAGCTGCGCTTCATCACGAGCCGCATGCGCAAGGAC
GAGCAAGAGCGGGAGGTCGTTGGCGAGTGGAAGTTCGCGGCCATGGTCGTCGACCGCTGCTGC
CTCATCATCTTCTCCCTGTTCACCATCATCTCCACCTGCGCCTGCCTCTTCTCGGCGCCCCAT
CTGGTCGCCTAGCGCACCCTGCT
```

Fig. 16

```
MRPGRLSVPLQLGFCANLLWIAVLLTAPQDSEQGAHERRLLADLLANYNTLE
RPVLNESEPLILSFGLTLQQIIDVDEKNQIITTNVWLNLDWIDVNLRWNPKD
YGGVQDLRIPPNKIWKPDVLMYNSADEKFDGTYPTNVVRSNGSCNYIPPGI
FKSTCKIDITWFPFDDQKCDLKFGSWTYHGYQLDLRVNSEEGGDLTTYIPNG
EWDLIGVPGVRNVREYACCPEPYIDITYTIHIRRRTLYYGFNLIIPCVLISS
MTLLGFTLPPDTGERLTLGVTILLSLTVFMLQLAETMPPTSDAVSIIGTYFA
CIMIMVAFSVVMTVVVLNYHHRNQETTEMPALIRTVFLVWLPWLLRMEPPGQ
KANRRSLFLNSKMKELELKERSSRSLLANVLDIDDDFRTANSAAAADCHGS
RTPFLGGGGASTVHACVHSSRELNLILRELRFITSRMRKDEQEREVVGEWK
FAAMVVDRCCLIIFSLFTIISTCACLFSAPHLVA
```

Fig. 17

RHIPICEPHALUS NICOTINIC ACETYLCHOLINE RECEPTOR AND PEST CONTROL ACTING THEREON

REFERENCE TO A SEQUENCE LISTING

This documentation includes a sequence listing.

FIELD OF THE INVENTION

Disclosed are a nicotinic acetylcholine receptor (nAChR) of *Rhipicephalus* ticks and an agent for pest control acting on this receptor. Disclosed is also a method of identifying a compound suitable as an agent for the pest control of *Rhipicephalus* ticks.

BACKGROUND

The following discussion of the background is merely provided to aid the reader in understanding the invention and is not admitted to describe or constitute prior art to the present invention.

A large number of ticks of the genus *Rhipicephalus* are of economic, medical, and veterinary importance because they are vectors of pathogens. Diseases transmitted by ticks of this genus include East Coast fever, anaplasmosis, babesiosis, rickettsiosis, Boutonneuse fever, Lyme disease, Q fever, Rocky Mountain spotted fever, and Crimean-Congo haemorrhagic fever. While most members of the genus *Rhipicephalus* are native to tropical Africa, some ticks such as the brown dog tick (*Rhipicephalus sanguineus*), also called kennel tick or pan-tropical dog tick, and *Rhipicephalus bursa*, are also found in southern Europe.

An important member of the genus *Rhipicephalus* is *Rhipicephalus microplus* (formerly *Boophilus microplus*), which is considered to be the most important tick parasite of livestock in the world. *Rhipicephalus microplus* can be found on a variety of hosts such as cattle, buffalo, the horse, donkey, goat, sheep, deer, the pig, dog as well as some wild animals. The tick particularly affects cattle in the tropical and subtropical regions. Heavy infestations on animals can decrease productivity and damage hides. *R. microplus* can also transmit babesiosis or "cattle fever" (caused by *Babesia bigemina* and *Babesia bovis*) and anaplasmosis (caused by *Anaplasma marginale*). Another vector of babesiosis is *Rhipicephalus annulatus*.

Both *R. microplus* and *R. annulatus* were essentially eliminated from the U.S. by 1943, however, they exist in Mexico, and despite a permanent quarantine zone along the Mexican border outbreaks at the Mexican border are frequent. *R. microplus* has also posed a major problem for the cattle industry in northern Australia for almost 100 years. Today, the ticks are confined to an area of northern and eastern Australia through the controlled movement of cattle and by climatic conditions which limit their spread.

In Central and South America, about 175 million cattle are exposed to *R. microplus*, which corresponds to approximately 70% of the cattle raised in this region. As a further example, *R. microplus* is one of the most important ticks infesting dairy animals of India, particularly the Punjab region. *R. microplus* has been suggested to have been introduced into East and South Africa from Madagascar, where it had originally arrived with cattle from southern Asia. In South Africa *R. microplus* is now established inter alia in areas along the southern and eastern coasts of the Western and Eastern Cape Provinces, and it is also present in the coastal regions of Mozambique, Tanzania and Kenya.

The tick is also found in parts of the eastern and central provinces of Zambia, throughout Malawi and to the east and north of Lake Malawi in Tanzania. *R. microplus* is also found in West Africa, mainly in Ivory Coast, Benin, Burkina Faso and Mali. There are serious concerns that this tick could spread to the entire West African region.

The most common and wide spread cattle tick in Africa is *Rhipicephalus decoloratus*, the African blue tick. Similar to *R. microplus*, cattle are the main host of this tick but it also feeds on horses, donkeys, sheep, goats and the preferred feeding sites of all stages on cattle are, back, upper legs, neck, shoulders, dewlap and the belly. The tick it is so far responsible for the transmission of babesiosis, anaplasmosis (caused by *Anaplasma marginale*) and theileriosis (caused by *Borrelia theileri*) in cattle, sheep, goats and horses in West Africa, East Africa and Southern Africa. Elands can be asymptomatic carriers of *A. marginale* and could thus serve as a reservoir of infection for domestic cattle. *R. decoloratus* is also suspected of being a vector of *Babesia trautmanni*, the cause of porcine babesiosis.

Apart from the diseases they transmit, both *R. decoloratus* and *R. microplus* can have a significant impact on cattle production. Some of the most relevant effects include irritation, weight loss, and damage of leather. Comparing mid-lactation Holstein-Friesian cows infested with *R. microplus* for 15 weeks, and uninfested control cows, it is reported from Australia that over the trial period control cows produced 2.86 l more milk and 0.14 kg more butterfat per day and had gained 10.6 kg more live-weight than the infested cows.

The main vector of *Theileria parva*, causing East Coast fever and Corridor disease in cattle, is a further member of the genus *Rhipicephalus*, namely *Rhipicephalus appendiculatus*, the brown ear tick. It is hypothesized that the saliva of *R. appendiculatus* contains a toxin and if large numbers of ticks infest an animal this toxin can interfere with the immune processes of the host, resulting in a loss of condition and outbreaks of babesiosis, anaplasmosis and heartwater in animals that were previously immune to these diseases. Severe infestations can lead to crumpling of the ear and infestations of the ear with the larvae of *Chrysomya bezziana* may occur. The tick is also responsible for the transmission of *Rickettsia conorii* to humans.

Yet another member of the genus *Rhipicephalus*, namely *R. zambeziensis*, is the vector for Corridor disease (caused by *Theileria parva*), benign bovine theileriosis (caused by *Theileria taurotragi*) and ehrlichiosis (caused by *Erhlichia bovis*).

The chemical control using acaricides is central in the efforts to eradicate *Rhipicephalus* such as *R. microplus* and *R. decoloratus*, however, the ticks have developed resistance to most agents used so far, such as organophosphates, pyrethroids, amidines and macrocyclic lactones. It would thus be advantageous to have further means available that can serve in controlling *Rhipicephalus* ticks.

SUMMARY

The present disclosure can be taken to generally relate to the control of one or more *Rhipicephalus* ectoparasites. Provided are an agent and a combination that can be applied to an animal infested with a tick of the genus *Rhipicephalus*. Furthermore, a method and a system for identifying compounds suitable for the control of ticks of the genus *Rhipicephalus* are provided. In some embodiments the animal is a livestock animal infested with *Rhipicephalus microplus*.

According to a first aspect, there is provided a nucleic acid molecule. The nucleic acid molecule encodes a polypeptide. This polypeptide may contain an amino acid sequence that has at least about 95%, including at least about 97% sequence identity to SEQ ID NO: 10. The encoded polypeptide may also contain an amino acid sequence, which has at least about 95%, including at least about 97% sequence identity to SEQ ID NO: 11. The encoded polypeptide may also contain an amino acid sequence, which has at least about 95%, including at least about 97% sequence identity to SEQ ID NO:12. The encoded polypeptide may also contain an amino acid sequence, which has at least about 95%, including at least about 97% sequence identity to SEQ ID NO: 13. The encoded polypeptide may also contain an amino acid sequence, which has at least about 95%, including at least about 97% sequence identity to SEQ ID NO:14. The encoded polypeptide may also contain an amino acid sequence that is a fragment of a continuous length of about 200 or more amino acids. Such a fragment represents a polypeptide, which has at least about 95%, including at least about 97% amino acid sequence identity to SEQ ID NO: 10. The encoded polypeptide may also contain an amino acid sequence that corresponds to a fragment of an amino acid sequence, with the fragment having at least about 98% sequence identity to a portion of SEQ ID NO: 10. The encoded polypeptide may also contain an amino acid sequence that is a fragment of a polypeptide, which has at least about 95%, including at least about 97% amino acid sequence identity to SEQ ID NO: 11. The encoded polypeptide may also contain an amino acid sequence that corresponds to a fragment of an amino acid sequence, with the fragment having at least about 95%, including at least about 97% sequence identity to a portion of SEQ ID NO: 11. The encoded polypeptide may also contain an amino acid sequence that is a fragment of a polypeptide, which has at least about 95%, including at least about 97% amino acid sequence identity to SEQ ID NO:12. The encoded polypeptide may also contain an amino acid sequence that corresponds to a fragment of an amino acid sequence, with the fragment having at least about 95%, including at least about 97% sequence identity to a portion of SEQ ID NO:12. The encoded polypeptide may also contain an amino acid sequence that is a fragment of a polypeptide, which has at least about 95%, including at least about 97% amino acid sequence identity to SEQ ID NO: 13. The encoded polypeptide may also contain an amino acid sequence that corresponds to a fragment of an amino acid sequence, with the fragment having at least about 95%, including at least about 97% sequence identity to a portion of SEQ ID NO: 13. The encoded polypeptide may also contain an amino acid sequence that is a fragment of a polypeptide, which has at least about 95%, including at least about 97% amino acid sequence identity to SEQ ID NO:14. The encoded polypeptide may also contain an amino acid sequence that corresponds to a fragment of an amino acid sequence, with the fragment having at least about 95%, including at least about 97% sequence identity to a portion of SEQ ID NO:14. Any such fragment is generally included in a functional nACh receptor subunit. In some embodiments the nucleic acid molecule encodes a fragment that is a portion of a functional nACh receptor subunit. In some embodiments the fragment encoded by the nucleic acid molecule defines a functional fragment of a nACh receptor subunit.

The nucleic acid sequence on the nucleic acid molecule according to the first aspect, which encodes a fragment of a continuous length of about 200 or more amino acids, is generally a continuous sequence.

In some embodiments the nucleic acid molecule according to the first aspect encodes a polypeptide, which includes an amino acid sequence that has at least about 95%, including at least about 97% sequence identity to SEQ ID NO: 2. In some embodiments the nucleic acid molecule according to the first aspect encodes a polypeptide, which essentially consists of an amino acid sequence that has at least about 95%, including at least about 97% sequence identity to SEQ ID NO: 2. In some embodiments the nucleic acid molecule according to the first aspect encodes a polypeptide, which consists of an amino acid sequence that has at least about 95%, including at least about 97% sequence identity to SEQ ID NO: 2.

In some embodiments the nucleic acid molecule according to the first aspect encodes a polypeptide that includes a fragment of a polypeptide, which has at least about 95%, including at least about 97% amino acid sequence identity to SEQ ID NO: 2. In some embodiments the nucleic acid molecule according to the first aspect encodes a polypeptide that includes to a fragment of an amino acid sequence that has at least about 98% sequence identity to SEQ ID NO: 2. In some embodiments the nucleic acid molecule according to the first aspect encodes a polypeptide that essentially consists of a fragment of a polypeptide, which has at least about 95%, including at least about 97% amino acid sequence identity to SEQ ID NO: 2. In some embodiments the nucleic acid molecule according to the first aspect encodes a polypeptide that essentially consists of a fragment of an amino acid sequence that has at least about 98% sequence identity to SEQ ID NO: 2, In some embodiments the nucleic acid molecule according to the first aspect encodes a polypeptide that consists of a fragment of a polypeptide, which has at least about 95%, including at least about 97% amino acid sequence identity to SEQ ID NO: 2. In some embodiments the nucleic acid molecule according to the first aspect encodes a polypeptide that corresponds to a fragment of an amino acid sequence that has at least about 98% sequence identity to SEQ ID NO: 2. Any such encoded fragment generally defines a functional fragment of a nACh receptor subunit. In some embodiments the fragment encoded by the nucleic acid molecule is a portion of a functional nACh receptor subunit. In some embodiments the fragment encoded by the nucleic acid molecule defines a functional fragment of a nACh receptor subunit.

In some embodiments the nucleic acid molecule according to the first aspect encodes a polypeptide, which includes an amino acid sequence that has at least about 95%, including at least about 97% sequence identity to SEQ ID NO: 4. In some embodiments the nucleic acid molecule according to the first aspect encodes a polypeptide, which essentially consists of an amino acid sequence that has at least about 95%, including at least about 97% sequence identity to SEQ ID NO: 4. In some embodiments the nucleic acid molecule according to the first aspect encodes a polypeptide, which consists of an amino acid sequence that has at least about 95%, including at least about 97% sequence identity to SEQ ID NO: 4.

In some embodiments the nucleic acid molecule according to the first aspect encodes a polypeptide that includes a fragment of a polypeptide, which has at least about 95%, including at least about 97% amino acid sequence identity to SEQ ID NO: 4. In some embodiments the nucleic acid molecule according to the first aspect encodes a polypeptide that includes to a fragment of an amino acid sequence that has at least about 98% sequence identity to SEQ ID NO: 4. In some embodiments the nucleic acid molecule according to the first aspect encodes a polypeptide that essentially consists of a fragment of a polypeptide, which has at least about 95%, including at least about 97% amino acid sequence identity to SEQ ID NO: 4. In some embodiments the nucleic acid molecule according to the first aspect encodes a polypeptide that essentially consists of a fragment of an amino acid sequence that has at least about 98% sequence identity to SEQ ID NO: 4, In some embodiments the nucleic acid molecule according to the first aspect encodes a polypeptide that consists of a fragment of a polypeptide, which has at least about 95%, including at least about 97% amino acid sequence identity to SEQ ID NO: 4. In some embodiments the nucleic acid molecule according to the first aspect encodes a polypeptide that corresponds to a fragment of an amino acid sequence that has at least about 98% sequence identity to SEQ ID NO: 4. Any such encoded fragment generally defines a functional fragment of a nACh receptor subunit. In some embodiments the fragment encoded by the nucleic acid molecule is a portion of a functional nACh receptor subunit.

In some embodiments the nucleic acid molecule according to the first aspect encodes a polypeptide, which includes an amino acid sequence that has at least about 95%, including at least about 97% sequence identity to SEQ ID NO: 6. In some embodiments the nucleic acid molecule according to the first aspect encodes a polypeptide, which essentially consists of an amino acid sequence that has at least about 95%, including at least about 97% sequence identity to SEQ ID NO: 6. In some embodiments the nucleic acid molecule according to the first aspect encodes a polypeptide, which consists of an amino acid sequence that has at least about 95%, including at least about 97% sequence identity to SEQ ID NO: 6.

In some embodiments the nucleic acid molecule according to the first aspect encodes a polypeptide that includes a fragment of a polypeptide, which has at least about 95%, including at least about 97% amino acid sequence identity to SEQ ID NO: 6. In some embodiments the nucleic acid molecule according to the first aspect encodes a polypeptide that includes to a fragment of an amino acid sequence that has at least about 98% sequence identity to SEQ ID NO: 6. In some embodiments the nucleic acid molecule according to the first aspect encodes a polypeptide that essentially consists of a fragment of a polypeptide, which has at least about 95%, including at least about 97% amino acid sequence identity to SEQ ID NO: 6. In some embodiments the nucleic acid molecule according to the first aspect encodes a polypeptide that essentially consists of a fragment of an amino acid sequence that has at least about 98% sequence identity to SEQ ID NO: 6, In some embodiments the nucleic acid molecule according to the first aspect encodes a polypeptide that consists of a fragment of a polypeptide, which has at least about 95%, including at least about 97% amino acid sequence identity to SEQ ID NO: 6. In some embodiments the nucleic acid molecule according to the first aspect encodes a polypeptide that corresponds to a fragment of an amino acid sequence that has at least about 98% sequence identity to SEQ ID NO: 6. Any such encoded fragment generally defines a functional fragment of a nACh receptor subunit. In some embodiments the fragment encoded by the nucleic acid molecule is a portion of a functional nACh receptor subunit.

In some embodiments the nucleic acid molecule according to the first aspect contains one or more regulatory regions such as a promoter. A respective regulatory region is operably linked to the sequence that encodes the polypeptide defined in the foregoing. In some embodiments the nucleic acid molecule according to the first aspect contains an expression cassette, in which the sequence that encodes the polypeptide is included. In some embodiments the nucleic acid molecule is an isolated nucleic acid molecule. In some embodiments the nucleic acid molecule is included in a vector. The nucleic acid molecule according to the first aspect may in some embodiments be a nucleic acid molecule of a host organism such as a chromosome. In such embodiments the nucleic acid molecule contains a heterologous sequence that encodes the above defined polypeptide.

According to a second aspect, there is provided a nucleic acid molecule. The nucleic acid molecule contains a nucleotide sequence, which may have about 95% or more, including about 97% or more sequence identity to SEQ ID NO: 15. The nucleotide sequence contained in the nucleic acid molecule may also have about 95% or more, including about 97% or more sequence identity to SEQ ID NO: 16. The nucleotide sequence contained in the nucleic acid molecule may furthermore have about 95% or more, including about 97% or more sequence identity to SEQ ID NO: 17. The nucleic acid molecule may also contain a nucleotide sequence that has about 95% or more, including about 97% or more sequence identity to SEQ ID NO: 18. The nucleic acid molecule may also contain a nucleotide sequence that has about 95% or more, including about 97% or more sequence identity to SEQ ID NO: 19. The nucleic acid molecule may also contain a nucleotide sequence that has about 95% or more, including about 97% or more sequence identity to a fragment of at least about 500 bases of SEQ ID NO: 15. The nucleic acid molecule may also contain a nucleotide sequence that has about 95% or more, including about 97% or more sequence identity to a fragment of at least about 500 bases of SEQ ID NO: 16. The nucleic acid molecule may furthermore contain a nucleotide sequence that has about 95% or more, including about 97% or more sequence identity to a fragment of at least about 500 bases of SEQ ID NO: 17. The nucleic acid molecule may also contain a nucleotide sequence that has about 95% or more, including about 97% or more sequence identity to a fragment of at least about 500 bases of SEQ ID NO: 18. The nucleic acid molecule may also contain a nucleotide sequence that has about 95% or more, including about 97% or more sequence identity to a fragment of at least about 500 bases of SEQ ID NO: 19. Any such fragment generally encodes a portion of a functional nACh receptor subunit. In some embodiments such a fragment encodes a fragment that defines a functional fragment of a nACh receptor subunit.

A fragment encoded by the nucleic acid molecule according to the second aspect is generally a fragment of a continuous length. The nucleic acid sequence on the nucleic acid molecule according to the second aspect, which encodes the fragment, is generally also a continuous sequence.

In some embodiments the nucleic acid molecule according to the second aspect contains a nucleotide sequence that contains a nucleotide sequence, which may have about 98% or more, including 98.5% or more, sequence identity to SEQ ID NO: 15. The nucleotide sequence contained in the nucleic acid molecule may in some embodiments also have about 98% or more, including 98.5% or more, sequence identity to SEQ ID NO: 16. The nucleotide sequence contained in the nucleic acid molecule may furthermore have about 98% or more, including 98.5% or more, sequence identity to SEQ ID NO: 17. The nucleic acid molecule may also contain a nucleotide sequence that has about 98% or more, including 98.5% or more, sequence identity to SEQ ID NO: 18. In some embodiments the nucleic acid molecule may contain a nucleotide sequence that has about 98% or more, including 98.5% or more, sequence identity to SEQ ID NO: 19.

In some embodiments the nucleic acid molecule may also contain a nucleotide sequence that has about 95% or more, including about 97% or more sequence identity to a fragment of at least about 600 bases of SEQ ID NO: 15. The nucleic acid molecule may also contain a nucleotide sequence that has about 95% or more, including about 97% or more sequence identity to a fragment of at least about 600 bases of SEQ ID NO: 16. The nucleic acid molecule may furthermore contain a nucleotide sequence that has about 95% or more, including about 97% or more sequence identity to a fragment of at least about 600 bases of SEQ ID NO: 17. The nucleic acid molecule may also contain a nucleotide sequence that has about 95% or more, including about 97% or more sequence identity to a fragment of at least about 600 bases of SEQ ID NO: 18.

The nucleic acid molecule may also contain a nucleotide sequence that has about 95% or more, including about 97% or more sequence identity to a fragment of at least about 600 bases of SEQ ID NO: 19.

In some embodiments the nucleic acid molecule may also contain a nucleotide sequence that has about 98% or more, including 98.5% or more, sequence identity to a fragment of at least about 600 bases of SEQ ID NO: 15. The nucleic acid molecule may also contain a nucleotide sequence that has about 98% or more, including 98.5% or more, sequence identity to a fragment of at least about 600 bases of SEQ ID NO: 16. The nucleic acid molecule may furthermore contain a nucleotide sequence that has about 98% or more, including 98.5% or more, sequence identity to a fragment of at least about 600 bases of SEQ ID NO: 17. The nucleic acid molecule may also contain a nucleotide sequence that has about 98% or more, including 98.5% or more, sequence identity to a fragment of at least about 600 bases of SEQ ID NO: 18. The nucleic acid molecule may furthermore contain a nucleotide sequence that has about 98% or more, including 98.5% or more, sequence identity to a fragment of at least about 600 bases of SEQ ID NO: 19.

The nucleic acid molecule according to the second aspect may in some embodiments also be a nucleic acid molecule according to the first aspect.

In some embodiments the nucleic acid molecule according to the second aspect contains a nucleotide sequence, which may have about 98% or more sequence identity to SEQ ID NO: 1. The nucleotide sequence contained in the nucleic acid molecule may have about 98% or more sequence identity to SEQ ID NO: 3. The nucleotide sequence contained in the nucleic acid molecule may have about 98% or more sequence identity to SEQ ID NO: 5. The nucleic acid molecule may also contain a nucleotide sequence that has about 98% or more sequence identity to SEQ ID NO: 7. The nucleotide sequence included in the nucleic acid molecule may have about 98% or more sequence identity to SEQ ID NO: 8. The nucleotide sequence contained in the nucleic acid molecule may have about 98% or more sequence identity to SEQ ID NO: 9. The nucleic acid molecule may also contain a nucleotide sequence that has about 98% or more sequence identity to a fragment of SEQ ID NO: 1. The nucleic acid molecule may also contain a nucleotide sequence that corresponds to a fragment of a nucleotide sequence that has about 98% or more sequence identity to SEQ ID NO: 1. A respective fragment encodes a functional fragment of a nicotinic acetylcholine receptor (nACh receptor) subunit. The nucleic acid molecule may also contain a nucleotide sequence that has about 98% or more sequence identity to a fragment of SEQ ID NO: 3. The nucleic acid molecule may also contain a nucleotide sequence that corresponds to a fragment of a nucleotide sequence that about 98% or more sequence identity to SEQ ID NO: 3. A respective fragment generally encodes a functional fragment of a nACh receptor subunit. In some embodiments the nucleic acid molecule encodes a fragment that is a portion of a functional nACh receptor subunit. The nucleic acid molecule may also contain a nucleotide sequence that has about 98% or more sequence identity to a fragment of SEQ ID NO: 5. The nucleic acid molecule may also contain a nucleotide sequence that corresponds to a fragment of a nucleotide sequence that has about 98% or more sequence identity to SEQ ID NO: 5. A respective fragment encodes a functional fragment of a nACh receptor subunit. The nucleic acid molecule may also contain a nucleotide sequence that has about 98% or more sequence identity to a fragment of SEQ ID NO: 7. The nucleic acid molecule may also contain a nucleotide sequence that corresponds to a fragment of a nucleotide sequence that has about 98% or more sequence identity to SEQ ID NO: 7. A respective fragment generally encodes a functional fragment of a nACh receptor subunit. In some embodiments the fragment encoded by the nucleic acid molecule is a portion of a functional nACh receptor subunit. The nucleic acid molecule may also contain a nucleotide sequence that has about 98% or more sequence identity to a fragment of SEQ ID NO: 8. The nucleic acid molecule may also contain a nucleotide sequence that corresponds to a fragment of a nucleotide sequence that about 98% or more sequence identity to SEQ ID NO: 8. A respective fragment generally encodes a functional fragment of a nACh receptor subunit. In some embodiments the nucleic acid molecule encodes a fragment that is a portion of a functional nACh receptor subunit. The nucleic acid molecule may also contain a nucleotide sequence that has about 98% or more sequence identity to a fragment of SEQ ID NO: 9. The nucleic acid molecule may also contain a nucleotide sequence that corresponds to a fragment of a nucleotide sequence that has about 98% or more sequence identity to SEQ ID NO: 9. Also such a fragment generally encodes a functional fragment of a nACh receptor subunit. In some embodiments the fragment encoded by the nucleic acid molecule is a portion of a functional nACh receptor subunit.

In some embodiments the nucleic acid molecule according to the second aspect contains one or more regulatory regions such as a promoter. A respective regulatory region may be operably linked to the sequence that may have about 95% or more, including about 97% or more sequence identity to SEQ ID NO: 15. A respective regulatory region may also be operably linked to the sequence that may have about 95% or more, including about 97% or more sequence identity to SEQ ID NO: 16. The regulatory region may also be operably linked to the sequence that may have about 95% or more, including about 97% or more sequence identity to SEQ ID NO: 17. The regulatory region may furthermore be operably linked to the sequence that may have about 95% or more, including about 97% or more sequence identity to SEQ ID NO: 18. The regulatory region may furthermore be operably linked to the sequence that may have about 95% or more, including about 97% or more sequence identity to SEQ ID NO: 19. The regulatory region may also be operably linked to the sequence that has about 95% or more, including about 97% or more sequence identity to a fragment as defined above. In some embodiments the nucleic acid molecule according to the second aspect contains an expression cassette, in which the sequence that encodes the polypeptide is included. In some embodiments the nucleic acid molecule is an isolated nucleic acid molecule. In some embodiments the nucleic acid molecule is included in a vector. The nucleic acid molecule according to the second aspect may in some embodiments be a nucleic acid molecule of a host organism such as a chromosome. In such embodiments the nucleic acid molecule contains a heterologous sequence that encodes the above defined polypeptide.

According to a third aspect, there is provided a polypeptide. The polypeptide may be encoded by a nucleic acid molecule according to the first aspect. The polypeptide may also be encoded by a nucleic acid molecule according to the second aspect. In some embodiments the polypeptide may be encoded by a nucleic acid molecule according to the first aspect, which is also a nucleic acid molecule according to the second aspect.

The polypeptide according to the third aspect may be expressed by a nucleic acid molecule according to the first aspect and/or by a nucleic acid molecule according to the second aspect. In some embodiments the polypeptide may be expressed by a vector that includes the nucleic acid molecule according to the first aspect and/or the nucleic acid molecule according to the second aspect.

The polypeptide according to the third aspect is a subunit of a nACh receptor. Generally a polypeptide according to the third aspect defines a functional nACh receptor subunit. In some embodiments the polypeptide according to the third aspect is included in a heteropentamer. The respective heteropentamer can be taken to define the nACh receptor. In some embodiments the polypeptide according to the third aspect is included in a homopentamer. The respective homopentamer can likewise be taken to define the nACh receptor.

In embodiments where the polypeptide according to the third aspect defines a fragment of a nACh receptor subunit, this fragment is generally defined by an amino acid sequence of a continuous length.

According to a fourth aspect, there is provided a host cell. The host cell contains a heterologous nucleic acid sequence, which encodes a polypeptide. This polypeptide may include an amino acid sequence that has at least about 95%, including at least about 97% sequence identity to SEQ ID NO: 10. The encoded polypeptide may also contain an amino acid sequence, which has at least about 95%, including at least about 97% sequence identity to SEQ ID NO: 11. The encoded polypeptide may also contain an amino acid sequence, which has at least about 95%, including at least about 97% sequence identity to SEQ ID NO: 12. The encoded polypeptide may also contain an amino acid sequence, which has at least about at least about 95%, including 97% sequence identity to SEQ ID NO: 13. The encoded polypeptide may furthermore contain an amino acid sequence, which has at least about at least about 95%, including about 97% sequence identity to SEQ ID NO: 14. The encoded polypeptide may also contain an amino acid sequence that is a fragment of a continuous length of about 200 or more amino acids. Such a fragment represents a polypeptide, which has at least about 95%, including at least about 97% amino acid sequence identity to SEQ ID NO: 10. The encoded polypeptide may also contain an amino acid sequence that corresponds to a fragment of an amino acid sequence, with the fragment having at least about 98% sequence identity to a portion of SEQ ID NO: 10. The encoded polypeptide may also contain an amino acid sequence that is a fragment of a polypeptide, which has at least about 95%, including at least about 97% amino acid sequence identity to SEQ ID NO: 11. The encoded polypeptide may also contain an amino acid sequence that corresponds to a fragment of an amino acid sequence, with the fragment having at least about 95%, including at least about 97% sequence identity to a portion of SEQ ID NO: 11. The encoded polypeptide may also contain an amino acid sequence that is a fragment of a polypeptide, which has at least about 95%, including at least about 97% amino acid sequence identity to SEQ ID NO: 12. The encoded polypeptide may also contain an amino acid sequence that corresponds to a fragment of an amino acid sequence, with the fragment having at least about 95%, including at least about 97% sequence identity to a portion of SEQ ID NO: 12. The encoded polypeptide may also contain an amino acid sequence that is a fragment of a polypeptide, which has at least about 95%, including at least about 97% amino acid sequence identity to SEQ ID NO: 13. The encoded polypeptide may also contain an amino acid sequence that corresponds to a fragment of an amino acid sequence, with the fragment having at least about 98% sequence identity to a portion of SEQ ID NO: 13. The encoded polypeptide may furthermore contain an amino acid sequence that is a fragment of a polypeptide, which has at least about 95%, including at least about 97% amino acid sequence identity to SEQ ID NO: 14. The encoded polypeptide may also contain an amino acid sequence that corresponds to a fragment of an amino acid sequence, with the fragment having at least about 98% sequence identity to a portion of SEQ ID NO: 14. Any such fragment is generally included in a functional nACh receptor subunit. In some embodiments the heterologous nucleic acid sequence encodes a fragment that is a portion of a functional nACh receptor subunit. In some embodiments the heterologous nucleic acid sequence encodes a fragment that defines a functional fragment of a nACh receptor subunit.

A fragment encoded by the heterologous nucleic acid sequence included in the host cell according to the fourth aspect is generally a fragment of a continuous length. The heterologous nucleic acid sequence encoding the fragment is generally also a continuous sequence.

In some embodiments the heterologous nucleic acid sequence included in the host cell according to the fourth aspect is operably linked to one or more regulatory regions such as a promoter. In some embodiments the heterologous nucleic acid sequence is included in an expression cassette. In some embodiments the heterologous nucleic acid sequence is included in a nucleic acid molecule that is distinct from the host cell's genome. The heterologous nucleic acid sequence may for example be included in a nucleic acid molecule that is distinct from the host cell's chromosome. In some embodiments the heterologous nucleic acid sequence is included in a vector. In some embodiments the heterologous nucleic acid sequence is integrated into a nucleic acid molecule of a host organism such as a chromosome.

The heterologous nucleic acid sequence included in the host cell according to the fourth aspect may in some embodiments be included in a nucleic acid molecule according to the first aspect. In some embodiments the heterologous nucleic acid sequence may be included in a nucleic acid molecule according to the second aspect.

In some embodiments the host cell according to the fourth aspect contains a polypeptide according to the third aspect.

According to a fifth aspect, there is provided a host cell. The host cell contains a heterologous nucleic acid sequence, which may have about 95% or more, including about 97% or more sequence identity to SEQ ID NO: 15. The heterologous nucleic acid sequence may also have about 95% or more, including about 97% or more sequence identity to SEQ ID NO: 16. The heterologous nucleic acid sequence may furthermore have about 95% or more, including about 97% or more sequence identity to SEQ ID NO: 17. The heterologous nucleic acid sequence may furthermore have about 95% or more, including about 97% or more sequence identity to SEQ ID NO: 18. The heterologous nucleic acid sequence may furthermore have about 95% or more, including about 97% or more sequence identity to SEQ ID NO: 19. The heterologous nucleic acid sequence may also have about 95% or more, including about 97% or more sequence identity to a fragment of at least about 500 bases of SEQ ID NO: 15. The heterologous nucleic acid sequence may also contain a nucleotide sequence that has about 95% or more, including about 97% or more sequence identity to a fragment of at least about 500 bases of SEQ ID NO: 16. The heterologous nucleic acid sequence may furthermore have about 95% or more, including about 97% or more sequence identity to a fragment of at least about 500 bases of SEQ ID NO: 17. The heterologous nucleic acid sequence may also have about 95% or more, including about 97% or more sequence identity to a fragment of at least about 500 bases of SEQ ID NO: 18. The heterologous nucleic acid sequence may furthermore have about 95% or more, including about 97% or more sequence identity to a fragment of at least about 500 bases of SEQ ID NO: 19. Any such fragment generally encodes a portion of a functional nACh receptor subunit. In some embodiments the fragment encoded by the heterologous nucleic acid sequence that is a portion of a functional nACh receptor subunit.

A fragment encoded by the heterologous nucleic acid sequence included in the host cell according to the fifth aspect is generally a fragment of a continuous length. The heterologous nucleic acid sequence encoding the fragment is generally also a continuous sequence.

In some embodiments the heterologous nucleic acid sequence included in the host cell according to a fifth aspect contains a nucleotide sequence, which may have about 98% or more, including 98.5% or more, sequence identity to SEQ ID NO: 15. The heterologous nucleic acid sequence may in some embodiments also have about 98% or more, including 98.5% or more, sequence identity to SEQ ID NO: 16. The heterologous nucleic acid sequence may furthermore have about 98% or more, including 98.5% or more, sequence identity to SEQ ID NO: 17. The heterologous nucleic acid sequence may also have about 98% or more, including 98.5% or more, sequence identity to SEQ ID NO: 18. The heterologous nucleic acid sequence may in some embodiments also have about 98% or more, including 98.5% or more, sequence identity to SEQ ID NO: 19.

In some embodiments the heterologous nucleic acid sequence may have about 95% or more, including about 97% or more sequence identity to a fragment of at least about 600 bases of SEQ ID NO: 15. The heterologous nucleic acid sequence may have about 95% or more, including about 97% or more sequence identity to a fragment of at least about 600 bases of SEQ ID NO: 16. The heterologous nucleic acid sequence may furthermore have about 95% or more, including about 97% or more sequence identity to a fragment of at least about 600 bases of SEQ ID NO: 17. The heterologous nucleic acid sequence may also have about 95% or more, including about 97% or more sequence identity to a fragment of at least about 600 bases of SEQ ID NO: 18. The heterologous nucleic acid sequence may also have about 95% or more, including about 97% or more sequence identity to a fragment of at least about 600 bases of SEQ ID NO: 19.

In some embodiments the heterologous nucleic acid sequence may also have about 98% or more, including 98.5% or more, sequence identity to a fragment of at least about 600 bases of SEQ ID NO: 15. The heterologous nucleic acid sequence may also have about 98% or more, including 98.5% or more, sequence identity to a fragment of at least about 600 bases of SEQ ID NO: 16. The heterologous nucleic acid sequence may have about 98% or more, including 98.5% or more, sequence identity to a fragment of at least about 600 bases of SEQ ID NO: 17. The heterologous nucleic acid sequence may also have about 98% or more, including 98.5% or more, sequence identity to a fragment of at least about 600 bases of SEQ ID NO: 18. The heterologous nucleic acid sequence may furthermore have about 98% or more, including 98.5% or more, sequence identity to a fragment of at least about 600 bases of SEQ ID NO: 19.

In some embodiments the heterologous nucleic acid sequence included in the host cell according to a fifth aspect contains a nucleotide sequence, which may have about 98% or more sequence identity to SEQ ID NO: 1. The heterologous nucleic acid sequence may have about 98% or more sequence identity to SEQ ID NO: 3. The heterologous nucleic acid sequence may also have about 98% or more sequence identity to SEQ ID NO: 5. The heterologous nucleic acid sequence may also have about 98% or more sequence identity to SEQ ID NO: 7. The heterologous nucleic acid sequence may also have about 98% or more sequence identity to SEQ ID NO: 8. The heterologous nucleic acid sequence may furthermore have about 98% or more sequence identity to SEQ ID NO: 9. The heterologous nucleic acid sequence may also have about 98% or more sequence identity to a fragment of SEQ ID NO: 1. The heterologous nucleic acid sequence may furthermore correspond to a fragment of a nucleotide sequence that has about 98% or more sequence identity to SEQ ID NO: 1. A respective fragment encodes a functional fragment of a nicotinic acetylcholine receptor (nACh receptor) subunit. The heterologous nucleic acid sequence may also have about 98% or more sequence identity to a fragment of SEQ ID NO: 3. The heterologous nucleic acid sequence may also correspond to a fragment of a nucleotide sequence that about 98% or more sequence identity to SEQ ID NO: 3. A respective fragment generally encodes a functional fragment of a nACh receptor subunit. In some embodiments the fragment encoded by the heterologous nucleic acid sequence is a portion of a functional nACh receptor subunit. The heterologous nucleic acid sequence may also have about 98% or more sequence identity to a fragment of SEQ ID NO: 5. The heterologous nucleic acid sequence may also correspond to a fragment of a nucleotide sequence that has about 98% or more sequence identity to SEQ ID NO: 5. A respective fragment encodes a functional fragment of a nACh receptor subunit. The heterologous nucleic acid sequence may also have about 98% or more sequence identity to a fragment of SEQ ID NO: 7. The heterologous nucleic acid sequence may furthermore correspond to a fragment of a nucleotide sequence that has about 98% or more sequence identity to SEQ ID NO: 7. Also such a fragment generally encodes a functional fragment of a nACh receptor subunit. In some embodiments the fragment encoded by the heterologous nucleic acid sequence is a portion of a functional nACh receptor subunit. The heterologous nucleic acid sequence may also have about 98% or more sequence identity to a fragment of SEQ ID NO: 8. The heterologous nucleic acid sequence may also correspond to a fragment of a nucleotide sequence that about 98% or more sequence identity to SEQ ID NO: 8. A respective fragment generally encodes a functional fragment of a nACh receptor subunit. In some embodiments the fragment encoded by the heterologous nucleic acid sequence is a portion of a functional nACh receptor subunit. The heterologous nucleic acid sequence may also have about 98% or more sequence identity to a fragment of SEQ ID NO: 9. The heterologous nucleic acid sequence may also correspond to a fragment of a nucleotide sequence that about 98% or more sequence identity to SEQ ID NO: 9. A respective fragment generally encodes a functional fragment of a nACh receptor subunit. In some embodiments the fragment encoded by the heterologous nucleic acid sequence is a portion of a functional nACh receptor subunit.

In some embodiments the heterologous nucleic acid sequence included in the host cell according to the fifth aspect is operably linked to one or more regulatory regions such as a promoter. In some embodiments the heterologous nucleic acid sequence included in the host cell according to a fifth aspect is included in an expression cassette. In some embodiments the heterologous nucleic acid sequence is included in a nucleic acid molecule that is distinct from the host cell's genome. The heterologous nucleic acid sequence may for example be included in a nucleic acid molecule that is distinct from the host cell's chromosome. In some embodiments the heterologous nucleic acid sequence is included in a vector. In some embodiments the heterologous nucleic acid sequence is integrated into a nucleic acid molecule of a host organism such as a chromosome.

In some embodiments the host cell according to the fifth aspect contains a polypeptide according to the third aspect.

According to a sixth aspect, there is provided a method of identifying a compound capable of modulating activity of a *Rhipicephalus* nACh receptor. The method includes contacting a polypeptide according to the third aspect with a compound suspected to modulate activity of a *Rhipicephalus* nACh receptor. The method furthermore includes detecting the activity of the polypeptide according to the third aspect.

The method according to a sixth aspect may in some embodiments be an in vitro method. The method may in some embodiments include providing a polypeptide according to the third aspect. In the method the polypeptide according to the third aspect may be included in a host cell. The method may for example be based on using a host cell according to the fourth aspect and/or according to the fifth aspect. Such a method may include providing a host cell according to the fourth aspect and/or according to the fifth aspect. The method may for example be based on using a fraction of a host cell according to the fourth aspect and/or according to the fifth aspect, which includes a polypeptide according to the third aspect, expressed by the host cell. The method may for example be based on using a cell membrane of a respective host cell. As a further example, the method may be based on using an enriched polypeptide according to the third aspect. The method may for also be based on using an isolated or purified polypeptide according to the third aspect. The polypeptide may for example be reconstituted in a lipid layer, such as a lipid double layer.

Detecting the activity of the polypeptide according to the third aspect is generally based on the use of the polypeptide according to the third aspect, whether included in a host cell according to the fourth aspect and/or according to the fifth aspect or otherwise, in the form of a pentamer. The polypeptide may be used in the form of a homopentamer. The polypeptide may also be used in the form of a heteropentamer.

Detecting the activity of the polypeptide according to the third aspect may include detecting a current such as an inward current, of a cation. Examples of a suitable cation include, but are not limited to $Na^+$ and $K^+$. The detection may for example be performed by a voltage measurement. The detection may for example be performed via a suitable spectroscopic, photochemical, photometric or fluorometric detection technique, generally in combination with a dye. Detecting the activity of the polypeptide according to the third aspect may include a control measurement. Such a control measurement may be based on the use of a ligand of the polypeptide according to the third aspect. A ligand of the polypeptide according to the third aspect is for example acetylcholine. A control measurement may furthermore be based on the use of a compound known not to cause any current when contacted with the polypeptide according to the third aspect. A control measurement may also be based on the use of a compound known to block the activity of the polypeptide according to the third aspect.

Detecting the activity of the polypeptide according to the third aspect may include comparing the detected activity of the polypeptide according to the third aspect, when contacted with a compound suspected to modulate activity of a *Rhipicephalus* nACh receptor, to a control measurement. Detecting the activity of the polypeptide according to the third aspect may include comparing the detected activity to a threshold value. A respective threshold value may be a predetermined value.

The method according to a sixth aspect may in some embodiments be a method for determining whether a compound has agonist or antagonist activity relative to a *Rhipicephalus* nACh receptor.

According to a seventh aspect, there is provided a method of controlling an ectoparasite of the genus *Rhipicephalus*. The method includes applying a compound effective in modulating activity of a polypeptide according to the third aspect. Particular aspects of this method may also be taken to relate to a compound effective in modulating activity of a polypeptide encoded by the nucleic acid molecule encoding a polypeptide, wherein the polypeptide comprises an amino acid sequence having at least 95% sequence identity to at least one of SEQ ID NO: 10, SEQ ID NO: 11, SEQ ID NO: 12, SEQ ID NO: 13 or to SEQ ID NO: 14, or a fragment of at least 200 amino acids thereof, the fragment being comprised in a functional nACh receptor subunit, wherein the nucleic acid molecule encodes a polypeptide sequence having at least 95% sequence identity to at least one of (i) SEQ ID NO: 2, SEQ ID NO: 4, or to SEQ ID NO: 6, or a fragment thereof, the fragment defining a functional fragment of a nACh receptor subunit; or (ii) SEQ ID NO: 15, SEQ ID NO: 16, SEQ ID NO: 17, SEQ ID NO: 18 or to SEQ ID NO: 19, or to a fragment of at least 600 bases thereof, the fragment encoding a portion of a functional nACh receptor subunit, wherein the nucleotide sequence has at least about 98% sequence identity to at least one of SEQ ID NO: 1, SEQ ID NO: 3, SEQ ID NO: 5, SEQ ID NO: 7, SEQ ID NO: 8 or to SEQ ID NO: 9, or to a fragment thereof encoding a functional fragment of a nACh receptor subunit, wherein the nucleic acid molecule further comprises one or more regulatory regions operatively linked to the nucleic acid sequence encoding said amino acid sequence, wherein the polypeptide is a homopentamer, or, a host cell comprising a heterologous nucleic acid sequence encoding a polypeptide, wherein the polypeptide comprises an amino acid sequence having at least 97% sequence identity to at least one of SEQ ID NO: 10, SEQ ID NO: 11, SEQ ID NO: 12 or to SEQ ID NO: 13, or a fragment of at least 200 amino acids thereof, the fragment being comprised in a functional nACh receptor subunit for use in a method of controlling an ectoparasite of the genus *Rhipicephalus*.

The method according to a seventh aspect may include applying the compound effective in modulating activity of a polypeptide according to the third aspect to an animal infested with an ectoparasite of the genus *Rhipicephalus*. The method may include contacting an ectoparasite of the genus *Rhipicephalus* with the respective compound. Such a compound is in typical embodiments obtainable with a method according to the sixth aspect. In some embodiments such a compound has been obtained with a method according to the sixth aspect.

In some embodiments the method according to the seventh aspect includes combining the compound effective in modulating activity of a polypeptide according to the third aspect with a compound of the following formula (VI):

(VI)

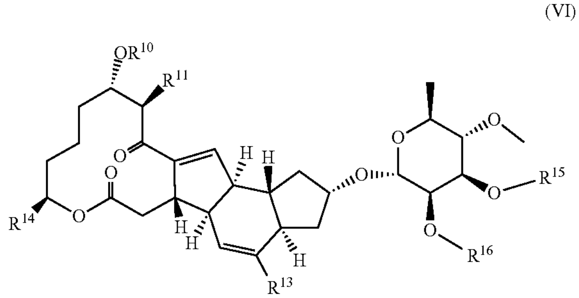

In this formula $R^{11}$, $R^{13}$, $R^{14}$, $R^{15}$ and $R^{16}$ may, independently from one another, be a hydrogen atom or an alkyl group. Any one or more of $R^{11}$, $R^{13}$, $R^{14}$, $R^{15}$ and $R^{16}$ may for example be an alkyl group with a main chain of one to six carbon atoms. $R^{10}$ may be H or one of the following groups:

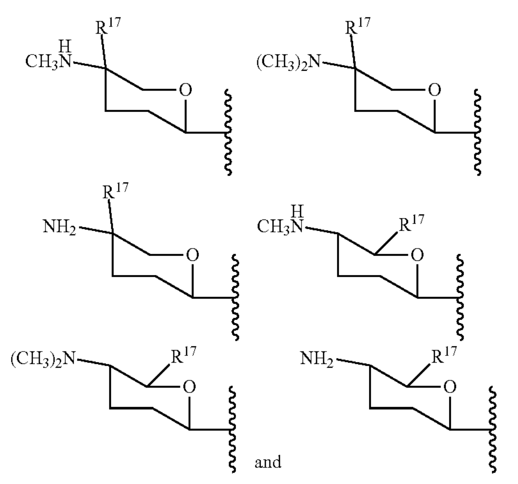

and

In this moiety $R^{17}$ may be an alkyl group with a main chain of one to six carbon atoms. In some embodiments $R^{17}$ may be an alkyl group with a main chain of one to three carbon atoms. More detailed information on compounds of formula (VI) can be found in U.S. Pat. Nos. 5,571,901, 5,631,155 and 5,202,242.

In this regard there is also provided the use of a neonicotinoid and spinosad in a method of controlling an ectoparasite of the genus *Rhipicephalus*. In some embodiments the use concerns a combination of imidacloprid and spinosad in a method of controlling an ectoparasite of the genus *Rhipicephalus*.

According to an eighth aspect, there is provided an antibody specific for a polypeptide according to the third aspect. Provided is also the use of an antibody specific for a polypeptide according to the third aspect for studying subunit composition, structure of functional domains, as well as in diagnostic applications and therapeutic applications. In some embodiments the antibody is a monoclonal antibody.

BRIEF DESCRIPTION OF THE DRAWINGS

FIG. 1 illustrates the situatedness and classification of the diverse subunits of nicotinic acetylcholine receptors from *R. microplus*.

FIG. 2 depicts the cloned cDNA sequence of the *R. microplus* nAChRα5 (Rma5), SEQ ID NO: 1. The sequence includes the START methionine and the STOP codon.

FIG. 3 depicts the amino acid sequence of the cloned sequence of the *R. microplus* nAChRα5 (Rma5), SEQ ID NO: 2. Expected loops in the folded polypeptide are indicated with lines, expected transmembrane regions (TM) are indicated by boxes.

FIG. 4 depicts the cloned cDNA sequence of a first splice variant of the *R. microplus* nAChRα6 (Rma6), SEQ ID NO: 3, including the START methionine and the STOP codon. The underlined region represents the difference to a second splice variant identified, depicted in FIG. 16.

FIG. 5 depicts the amino acid sequence of the cloned sequence of the first splice variant of *R. microplus* nAChRα6 (Rma6), SEQ ID NO: 4. Expected loops in the folded polypeptide are indicated with lines, expected transmembrane regions (TM) are indicated by boxes.

FIG. 6 depicts the results of experiments on the formation of functional *R. microplus* nicotinic acetylcholine receptors in *Xenopus* oocytes. Full length cDNA of identified *R. microplus* nAChR subunits was cloned into the pCR4 or the pGEMHE vector, and the identity of the respective subunit(s) assessed by sequencing. cRNA was synthesized and injected into deffoliculated *Xenopus* oocytes, and the presence of functional receptors was analysed after 72 hours, using the two-electrode voltage clamp technique.

FIG. 7 shows *R. microplus* nAChRα5 and nAChRα6 expression during life stages of *R. microplus*. Gene expression was normalised on the basis of sodium channel gene expression.

FIG. 8 depicts the complete nucleic acid sequence of the *R. microplus* nAChRα5 (Rma5), SEQ ID NO: 20, as identified in the *R. microplus* transcriptome. The sequence includes the 5' and 3' UTRs. The 5' and 3' ends were confirmed following RACE amplification, cloning and sequencing.

FIG. 9 depicts the complete nucleic acid sequence of the *R. microplus* nAChRα6 (Rma6), SEQ ID NO: 21, as assembled following 5' and 3' RACE amplification, cloning and sequencing. The sequence includes the 5' and 3' UTRs.

FIG. 10 shows dose response curves of Acetylcholine and Spinosad on *Xenopus* oocytes expressing Rma5 homopentamers (subunits of SEQ ID NO: 2).

FIG. 11A depicts a representative trace showing a response of an Rma5 homopentamer (subunits of SEQ ID NO: 2) to the application of acetylcholine (ACh, 300 μM).

Figure 14A:
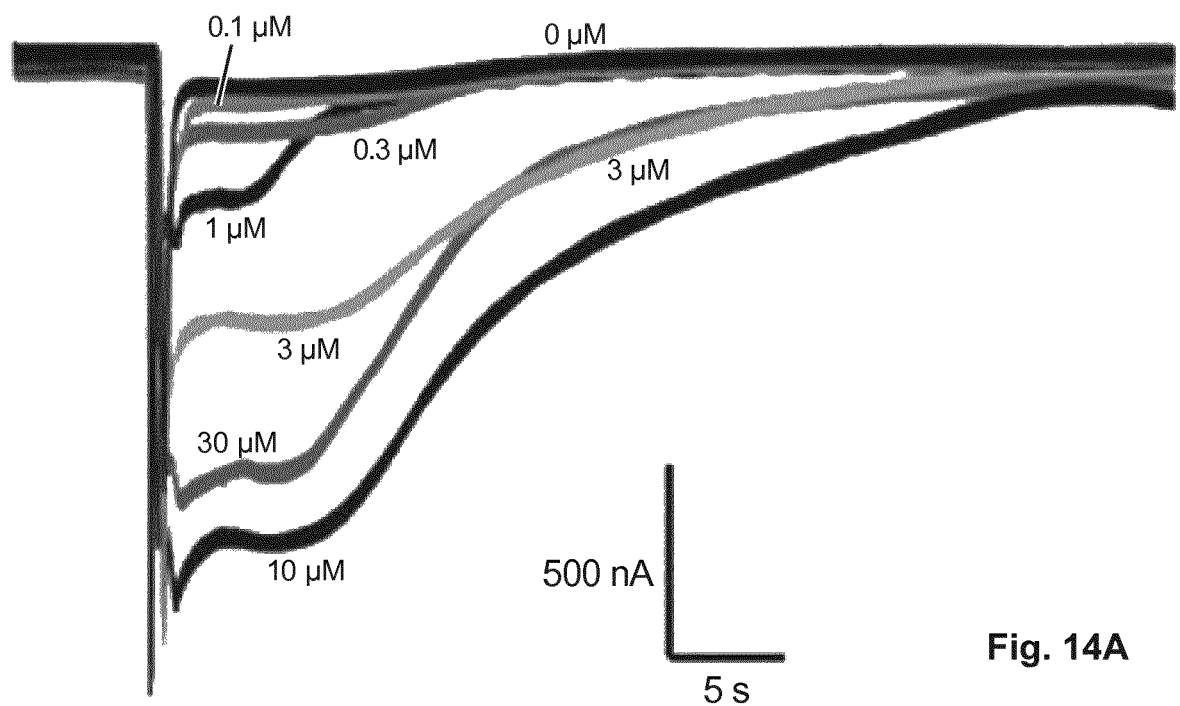
Figure 14B:
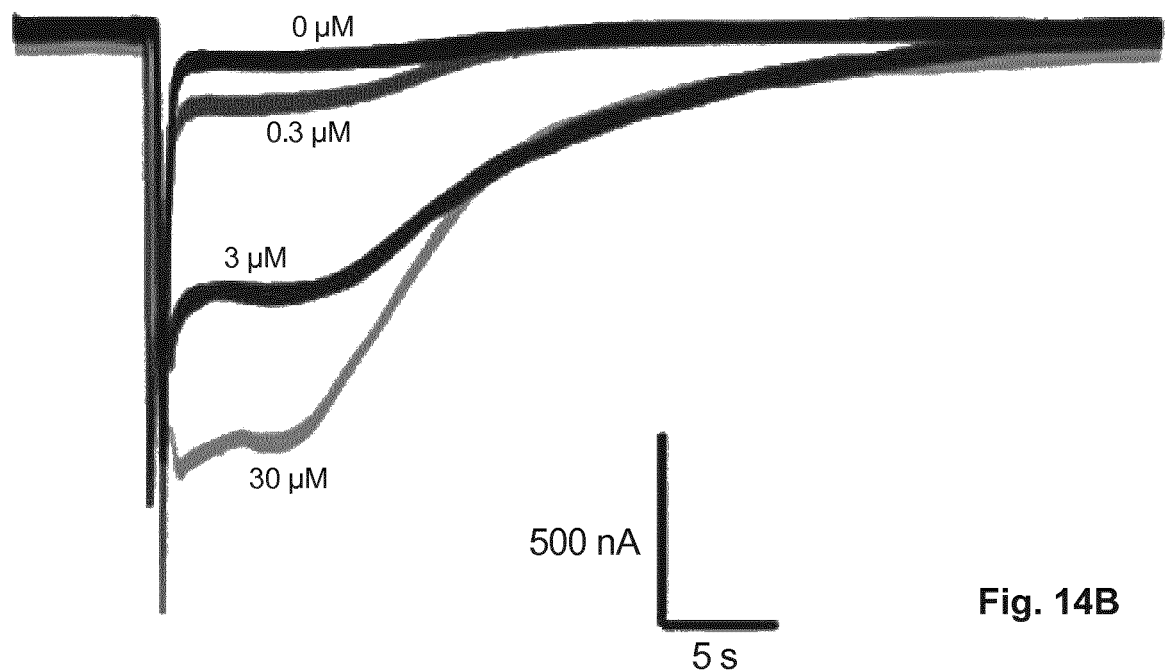

FIG. 14A depicts representative responses of Rma6 homopentamers to ACh (10 μM) following a 15 s pre-application of spinosad. Indicated values are the concentration of spinosad used in the 15 s pre-application in μM. The following concentrations were used: 0 μM, 0.1 μM, 0.3 μM, 1 μM, 3 μM, 10 μM, and 30 μM. FIG. 14B depicts is a copy of FIG. 14B, showing fewer traces for ease of reference. Traces of the following concentrations are shown: 0 μM, 0.3 μM, 3 μM, and 30 μM.

Figure 15:
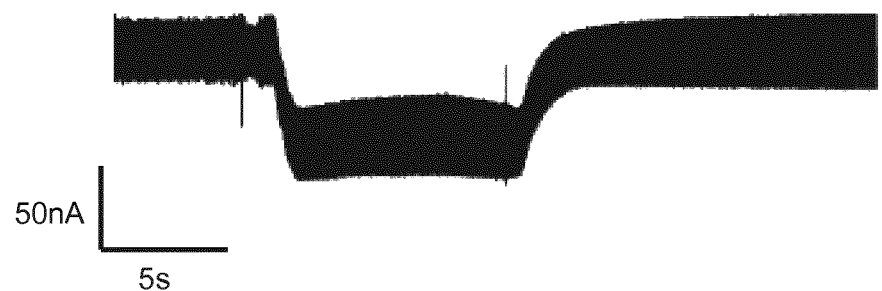

FIG. 15 shows a representative response of Rma6 to imidacloprid (100 μM).

FIG. 16 depicts the cloned cDNA sequence of a second splice variant of the *R. microplus* nAChRα6 (Rma6), SEQ ID NO: 5, including the START methionine and the STOP codon. The underlined region represents the difference to the first splice variant identified, depicted in FIG. 4.

FIG. 17 depicts the amino acid sequence of the cloned sequence of the second splice variant of *R. microplus* nAChRα6 (Rma6), SEQ ID NO: 6. The underlined region differs from the first splice variant identified, depicted in FIG. 5.

DETAILED DESCRIPTION

Provided herein are, amongst others, means for screening test compounds for their suitability as pesticidal agents for the control of *Rhipicephalus* ticks. In particular a test system is provided that is based on techniques that are well established in the art. In addition, readily available and obtainable compounds are provided that are suitable for the control of *Rhipicephalus* ticks. Provided are also nucleic acid sequences encoding nicotinic acetylcholine receptor subunits and polypeptides representing such receptor subunits.

Definitions

Unless otherwise stated, the following terms used in this document, including the description and claims, have the definitions given below.

The word "about" as used herein refers to a value being within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. The term "about" is also used to indicate that the amount or value in question may be the value designated or some other value that is approximately the same. The phrase is intended to convey that similar values promote equivalent results or effects as described herein. In this context "about" may refer to a range above and/or below of up to 10%. The word "about" refers in some embodiments to a range above and below a certain value that is up to 5%, such as up to up to 2%, up to 1%, or up to 0.5% above or below that value. In one embodiment "about" refers to a range up to 0.1% above and below a given value.

The term "detect" or "detecting", as well as the term "determine" or "determining" when used in the context of a signal such as a current, refers to any method that can be used to detect the flow of ions. Detection can be done both on a qualitative and a quantitative level. When used herein in combination with the words "level", "amount" or "value", the words "detect", "detecting", "determine" or "determining" are understood to generally refer to a quantitative rather than a qualitative level. Accordingly, a method as described herein may include a quantification of a current.

An "effective amount" of a compound, such as a pesticidal compound, is an amount—either as a single dose or as part of a series of doses—sufficient to provide a desire benefit in pest control, in particular to reduce the number of pest organisms on a subject such as an animal. A respective benefit may also be a reduction in reproduction or viability of a pest organism, or a benefit in the treatment or management of an undesired or pathological condition, or to delay or minimize one or more symptoms associated with the presence of the condition. Such a condition may be associated with or the result of infestation.

The term "essentially consists of" is understood to allow the presence of additional components in a sample or a composition that do not affect the properties of the sample or a composition. As an illustrative example, a pharmaceutical composition may include excipients if it essentially consists of an active ingredient.

The terms "expressing" and "expression" in reference to a polypeptide are intended to be understood in the ordinary meaning as used in the art. A polypeptide is expressed by a cell via transcription of a nucleic acid into mRNA, followed by translation into an initial polypeptide, which is folded and possibly further processed to a mature polypeptide. The polypeptides discussed in this disclosure are in addition being transported to the surface of the respective cell and integrated into the cell membrane. Hence, the statement that a cell is expressing such a polypeptide indicates that the polypeptide is found on the surface of the cell and implies that the polypeptide has been synthesized by the expression machinery of the respective cell.

With regard to the respective biological process itself, the terms "expression", "gene expression" or "expressing" refer to the entirety of regulatory pathways converting the information encoded in the nucleic acid sequence of a gene first into messenger RNA (mRNA) and then to a polypeptide. Accordingly, the expression of a gene includes its transcription into a primary hnRNA, the processing of this hnRNA into a mature RNA and the translation of the mRNA sequence into the corresponding amino acid sequence of the polypeptide. In this context, it is also noted that the term "gene product" refers not only to a polypeptide, including e.g. a mature polypeptide (including a splice variant thereof) encoded by that gene and a respective precursor protein where applicable, but also to the respective mRNA, which may be regarded as the "first gene product" during the course of gene expression.

By "fragment" in reference to a polypeptide such as receptor molecule is meant any amino acid sequence present in a corresponding polypeptide, as long as it is shorter than the full length sequence and as long as it is capable of performing the function of interest of the protein—in the case of an ionotropic receptor in the form of a ligand-gated ion channel the diffusion of ions, including a resulting current, through the channel in response to a specific ligand.

A functional nicotinic AChR, as used herein, is a receptor that shows an activity of nicotinic AChRs as assessed by any in vitro or in vivo detection technique disclosed herein or known to those of skill in the art. Possession of any such activity that may be assessed by any method known to those of skill in the art and provided herein is sufficient to designate a receptor as functional. When reference is made to a functional subunit of a nicotinic AChR, a respective subunit is capable of being combined with other subunits, and/or functional fragments of subunits, of a nicotinic AChR, thereby forming a functional nicotinic AChR. Methods for detecting nAChR protein and/or activity include, for example, assays that measure nicotine binding, $^{86}$Rb ion-flux, $Ca^{2+}$ influx, and/or the electrophysiological response of cells containing a heterologous nucleic acid sequence encoding one or more receptor subunits. Since all combinations of alpha and beta subunits may not form functional receptors, numerous combinations of alpha and beta subunits should be tested in order to fully characterize a particular subunit and cells which produce the same. Hence, as used herein, "functional" with respect to a recombinant or heterologous nicotinic AChR, or a fragment thereof, means that the receptor channel is able to provide for and regulate entry of nicotinic AChR-permeable ions, such as, for example, $Na^+$, $K^+$, $Ca^{2+}$ or $Ba^{2+}$, in response to a stimulus and/or bind ligands with known affinity for the receptor. It will typically be advantageous to select a setting where such nicotinic AChR activity is distinguishable from any endogenous AChR activity that may be produced by the host cell, for instance by electrophysiological, pharmacological and other means known to those of skill in the art.

As used herein, a "heterologous" nucleic acid molecule or a "heterologous" nucleic acid sequence is a nucleic acid molecule and sequence, respectively, that does not occur naturally as part of the genome of the cell in which it is present, or a nucleic acid sequence which is found in a location or locations in the genome that differ from that in which it occurs in nature. Typically, a heterologous nucleic acid molecule and/or sequence carries or is a sequence that is not endogenous to the host cell and has been artificially introduced into the cell. The cell that expresses a heterologous nucleic acid sequence may contain DNA encoding the same or different expression products. A heterologous nucleic acid sequence need not be expressed and may be integrated into the host cell genome or maintained episomally.

The term "inhibiting" a tick refers to a decrease in the numbers of living ticks, regardless of their live stage, or a decrease in the number of viable adult ticks, larvae, nymphs or eggs. The extent of reduction accomplished by a compound depends, naturally, upon the application rate of the compound, the particular compound used, and the target tick species. At least an inactivating amount should be used.

The term "isolated" indicates that the cell or cells, or the peptide(s) or nucleic acid molecule(s) has/have been removed from its/their normal physiological environment, e.g. a natural source, or that a peptide or nucleic acid is synthesized. Use of the term "isolated" indicates that a naturally occurring sequence has been removed from its normal cellular (i.e., chromosomal) environment. Thus, the sequence may be in a cell-free solution or placed in a different cellular environment. An isolated cell or isolated cells may for instance be included in a different medium such as an aqueous solution than provided originally, or placed in a different physiological environment. Typically isolated cells, peptides or nucleic acid molecule(s) constitute a higher fraction of the total cells, peptides or nucleic acid molecule(s) present in their environment, e.g. solution/ suspension as applicable, than in the environment from which they were taken. An isolated polypeptide or nucleic acid molecule is an oligomer or a polymer of amino acids (2 or more amino acids) or nucleotides coupled to each other, including a polypeptide or nucleic acid molecule that is isolated from a natural source or that is synthesized. The term "isolated" does not imply that the sequence is the only amino acid chain or nucleotide chain present, but that it is essentially free, e.g. about 90-95% pure or more, of e.g. non-amino acid material and/or non-nucleic acid material, respectively, naturally associated with it.

The term "locus" when used in connection with ticks refers to the environment in which a tick lives or where its eggs, larvae or nymphs are present, including the air surrounding them, the food they eat, or objects or materials which they contact. An active compound may for example be applied to grass that the larvae live on. Adult ticks may be controlled by applying the active compound to the animal that is infested, for instance topically. Oral administration of the compounds disclosed herein may be performed by mixing the compound in the animal's feed or drinking water, vitamin or mineral supplement, or by administering oral dosage forms such as drenches, tablets, bolus, salt block or capsules. It is contemplated that the compounds might also be useful to protect textiles, paper, stored grain, or seeds by applying an active compound to such substance.

A compound that "modulates the activity of a nicotinic AChR" refers to a compound that alters the activity of nAChR so that activity of the nAChR is different in the presence of the compound than in the absence of the compound or signal. Such compounds may include agonists, inverse agonists and antagonists. The term agonist refers to a substance, such as ACh, that activates receptor function. The term agonist also refers to a partial agonist. An agonist of a nAChR typically binds to the binding site of the natural receptor agonist, i.e. the acetylcholine binding site. An agonist of a nAChR may nevertheless also bind to a site that overlaps with, but is not identical to, the acetylcholine binding site. The term inverse agonist is applicable to a receptor that shows constitutive, also called intrinsic or basal, activity level in the absence of any ligand. For such a receptor an agonist increases the activity of a receptor above its basal level. An inverse agonist may bind to the receptor in a manner comparable to an agonist such as ACh, but it decreases the activity below the basal level. An agonist, including an inverse agonist, may induce receptor desensitization or it may not induce receptor desensitization. Without being bound by theory, it can be envisaged that an inactive and an active form of a ligand-bound AChR exist. The underlying idea, also termed a two state model of receptor activation, can be imagined as being analogous to Michaelis and Menten's concept that enzymatic conversion of a substrate proceeds as a two-step process involving the formation of an inactive complex. As a result a distinction can be made between ligand binding and receptor activation, and different receptor states can be envisaged with kinetic parameters determining the rate of conversion between these states. The term antagonist refers to a substance that interferes with receptor function. Typically, the effect of both an antagonist and an inverse agonist is observed as a blocking of activation by an agonist. An antagonist may be a competitive or a non-competitive antagonist. A competitive antagonist, or competitive blocker, interacts with or near the site specific for the agonist, e.g. ACh, for the same or closely situated site. A non-competitive antagonist or blocker inactivates the functioning of the receptor by interacting with a site other than the site that interacts with the natural receptor agonist, i.e. the acetylcholine binding site.

As used herein, nAChR or nACh receptor means nicotinic acetylcholine receptor.

The term "nucleic acid molecule" as used herein refers to any nucleic acid in any possible configuration, such as single stranded, double stranded or a combination thereof. Examples of nucleic acids include for instance DNA molecules, RNA molecules, analogues of the DNA or RNA generated using nucleotide analogues or using nucleic acid chemistry, locked nucleic acid molecules (LNA), protein nucleic acids molecules (PNA), alkylphosphonate and alkylphosphotriester nucleic acid molecules and tecto-RNA molecules (e.g. Liu, B., et al., J. Am. Chem. Soc. (2004) 126, 4076-4077). LNA has a modified RNA backbone with a methylene bridge between C4' and O2', providing the respective molecule with a higher duplex stability and nuclease resistance. Alkylphosphonate and alkylphosphotriester nucleic acid molecules can be viewed as a DNA or an RNA molecule, in which phosphate groups of the nucleic acid backbone are neutralized by exchanging the P—OH groups of the phosphate groups in the nucleic acid backbone to an alkyl and to an alkoxy group, respectively. DNA or RNA may be of genomic or synthetic origin and may be single or double stranded. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label.

Many nucleotide analogues are known and can be used for nucleic acids that are used in the methods described herein. A nucleotide analogue is a nucleotide containing a modification at for instance the base, sugar, or phosphate moieties. As an illustrative example, a substitution of 2'-OH residues of siRNA with 2'F, 2'O-Me or 2'H residues is known to improve the in vivo stability of the respective RNA. Modifications at the base moiety may be a natural or a synthetic modification of A, C, G, and T/U, a different purine or pyrimidine base, such as uracil-5-yl, hypoxanthin-9-yl, and 2-aminoadenin-9-yl, as well as a non-purine or a non-pyrimidine nucleotide base. Other nucleotide analogues serve as universal bases. Examples of universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

The terms "operably linked" or "operatively linked" as used herein, refer to the functional relationship of nucleic acids with regulatory and effector sequences of nucleotides, such as promoters, enhancers, transcriptional and translational stop sites, and other signal sequences. For example, operable linkage of nucleic acids to a promoter refers to the physical and functional relationship between the nucleic acids and the promoter such that the transcription of such nucleic acids is initiated from the promoter by an RNA polymerase that specifically recognizes, binds to and transcribes the nucleic acids. In order to optimize expression and/or in vitro transcription, it may be advantageous to remove or alter 5' and/or 3' untranslated portions of a clone, for instance to remove extra, potential alternative translation initiation (i.e., start) codons or other sequences that may interfere with or reduce expression, either at the level of transcription or translation. In some embodiments consensus ribosome binding sites can be inserted immediately 5' of the start codon to enhance expression. For expression of nAChR subunits in amphibian oocytes, it may also be advantageous to surround the subunit coding sequence with *Xenopus* β-globin gene 5' and 3' untranslated sequences for optimum protein production.

The terms "polypeptide" and "protein" are used interchangeably and refer to a polymer of amino acid residues and are not limited to a certain minimum length of the product. Where both terms are used concurrently, this twofold naming accounts for the use of both terms side by side in the art.

The term "purified" is understood to be a relative indication in comparison to the original environment of the cell, thereby representing an indication that the cell is relatively purer than in the natural environment. It therefore includes, but does not only refer to, an absolute value in the sense of absolute purity from other cells (such as a homogeneous cell population). Compared to the natural level, the level after purifying the cell will generally be at least 2-5 fold greater (e.g., in terms of cells/ml). Purification of at least one order of magnitude, such as about two or three orders, including for example about four or five orders of magnitude is expressly contemplated. It may be desired to obtain the cell at least essentially free of contamination, in particular free of other cells, at a functionally significant level, for example about 95%, about 95%, or 99% pure. With regard to a nucleic acid, peptide or a protein, the above applies mutatis mutandis. In this case purifying the nucleic acid, peptide or protein will for instance generally be at least 2-5 fold greater (e.g., in terms of mg/ml).

The word "recombinant" is used in this document to describe a nucleic acid molecule that, by virtue of its origin, manipulation, or both is not associated with all or a portion of the nucleic acid molecule with which it is associated in nature. Generally a recombinant nucleic acid molecule includes a sequence which does not naturally occur in the respective wildtype organism or cell. Typically a recombinant nucleic acid molecule is obtained by genetic engineering, usually constructed outside of a cell. Generally a recombinant nucleic acid molecule is substantially identical and/or substantial complementary to at least a portion of the corresponding nucleic acid molecule occurring in nature. A recombinant nucleic acid molecule may be of any origin, such as genomic, cDNA, mammalian, bacterial, viral, semi-synthetic or synthetic origin. The term "recombinant" as used with respect to a protein/polypeptide means a polypeptide produced by expression of a recombinant polynucleotide.

"Stringent" conditions is a term commonly used in the art. Stringent conditions are conditions under which a first nucleic acid sequence will only hybridize to a second nucleic acid sequence, if the two sequences have a high homology. Stringent conditions are sequence-dependent and will be different in different circumstances. Stringent conditions may be selected to be about 5-10° C. lower than the thermal melting point (Tm) for the specific sequence at a defined ionic strength pH. As an example, stringent hybridization conditions may be hybridization in 6×sodium chloride/sodium citrate (SSC), 0.5% SDS at about 68° C. followed by one or more washes in 2×SSC, 0.5% SDS at room temperature. Another example of stringent hybridization conditions is hybridization in 6×SSC at about 45° C., followed by one or more washes in 0.2×SSC, 0.1% SDS at about 50-65° C.

The term "subject" as used herein, also addressed as an individual, refers to an animal, generally a mammal. A subject may be a mammalian species such as a cattle or a goat. The subject may also be a sheep. In some embodiments the subject is a horse. The subject may also be a dog or a cat.

In some embodiments the subject is a ferret or a chinchilla. In some embodiments the subject is a pig. The subject may also be a monkey, a rabbit, a mouse, a rat, a Guinea pig, a hamster, an ape or a human.

The term "variant" as used herein can refer to a nucleotide sequence in which the sequence differs from the sequence most prevalent in a population, for example by one nucleotide, in the case of the point mutations described herein. For example, some variations or substitutions in the nucleotide sequence encoding a nAChR can alter a codon so that a different amino acid is encoded resulting in a variant polypeptide. The term "variant" can also refer to a polypeptide in which the sequence differs from a given sequence as explained further below. A variant may for example be a polypeptide in which the sequence differs from the sequence most prevalent in a population. A polypeptide sequence can for instance differ at a position that does not change the amino acid sequence of the encoded polypeptide, i.e. a conserved change. Variant polypeptides can be encoded by a mutated nAChR sequence.

The terms "comprising", "including," containing", "having" etc. shall be read expansively or open-ended and without limitation. Singular forms such as "a", "an" or "the" include plural references unless the context clearly indicates otherwise. Thus, for example, reference to a "vector" includes a single vector as well as a plurality of vectors, either the same—e.g. the same operon—or different. Likewise reference to "cell" includes a single cell as well as a plurality of cells. Unless otherwise indicated, the term "at least" preceding a series of elements is to be understood to refer to every element in the series. The terms "at least one" and "at least one of" include for example, one, two, three, four, or five or more elements. It is furthermore understood that slight variations above and below a stated range can be used to achieve substantially the same results as a value within the range. Also, unless indicated otherwise, the disclosure of ranges is intended as a continuous range including every value between the minimum and maximum values.

The scope and meaning of any use of a term will be apparent from the specific context in which the term is used. Certain further definitions for selected terms used throughout this document are given in the appropriate context of the detailed description, as applicable. Unless otherwise defined, all other scientific and technical terms used in the description, figures and claims have their ordinary meaning as commonly understood by one of ordinary skill in the art.

Action of Compounds on Nicotinic Acetylcholine Receptors

Control of ticks and mites has focused on the use of acaricides, such as organophosphates, carbamates, pyrethroids, formamidine compounds, amidines, and macrocyclic lactones, although with limited success. On the other hand, one of the most widely used insecticides in the world is the neonicotinoid imidacloprid. Neonicotinoids such as imidacloprid are known to be specific for insect nervous tissue without affecting mammals or mites in the same manner. Ticks, being arachnids rather than insects, have likewise been regarded as practically unaffected by imidacloprid. The present inventors were therefore surprised by the finding that imidacloprid induced responses on a nicotinic acetylcholine receptor from *R. microplus* that they had expressed in *Xenopus* oocytes.

Neonicotinoids are very potent for protecting crops against piercing-sucking insects. Some of these compounds are also used in veterinary medicine, especially for controlling fleas in cats and dogs.

Acetylcholine is a neurotransmitter acting in the autonomic nervous system and at the neuromuscular junction. In the brain acetylcholine acts as a neuromodulator. Receptors for acetylcholine are either agonist-gated ion channels (nAChRs) or G-protein-coupled receptors (mAChRs) which in turn activate ionic channels. NAChRs belong to the superfamily of neurotransmitter-gated ion channels and define a pentameric transmembrane complex (for an overview see e.g. Tomizawa and Casida, Annu. Rev. Pharmacol. Toxicol. [2005] 45:247-268). Binding of acetylcholine to a nAChR causes a rotation of helices of the receptor by 15°, resulting in a transient opening of a central pore that defines an integral cation-selective ion channel. In vivo, this results in the influx of extracellular sodium and calcium into the cell, and efflux of intracellular potassium out of the cell, disrupting the balance of the membrane potential. With $Na^+$ influx dominating over $K^+$ efflux, depolarization occurs. NAChRs generally have a long extracellular N-terminal ligand binding domain, four transmembrane regions and an extracellular C terminus.

The selectivity of neonicotinoid insecticides is known to be largely attributable to differences in binding to insect versus mammalian nAChRs. (-)-Nicotine and acetylcholine have a quaternary ($sp^3$) nitrogen atom, a hydrogen bond acceptor, namely a pyridine nitrogen vs. a carboxyl oxygen, and a "dummy point" that imposes directionality to the pyridine nitrogen, and the oxygen, respectively (Tomizawa and Casida, 2005, supra). In contrast thereto, neonicotinoids have a nitro or cyano group or an equivalent electronegative moiety, and show coplanarity between this tip and a substituted guanidine/amidine moiety.

nAChRs can form both homopentamers and heteropentamers. In the body, the muscle-type receptors are found in the form of heteropentamers that contain $\alpha_1$, $\beta_1$, γ, and δ subunits (embryonic form), or as heteropentamers that contain $\alpha_1$, $\beta_1$, δ, and ε subunits (adult form). Neuronal subtypes have been found as homomeric $\alpha_2$-$\alpha_{10}$ subunits or as heteromeric subunits of a respective α subunit type and $\beta_2$-$\beta_4$ subunits. For heteromeric nAChRs containing non-α subunits, it has been observed that acetylcholine binds at the interface of the N-terminal regions of α- and non-α subunits. For homomers or heteropentamers containing two different α subunits, the acetylcholine binding site is thought to be formed at the interface of two adjacent α subunits (Matsuda et al., Mol. Pharmacol. [2009] 76:1-10).

The agonist binding site of a nAChR is formed by six distinct amino-acid loops (loops A-F). Generally two agonist binding sites are thought to be present on the extracellular surface of a heteropentamer of a nAChR receptor-cation-channel. On a homopentamer five agonist binding sites formed by loops A-F on adjacent edges of the subunits are thought to exist. The 2-nitroimino-imidazolidine moiety of imidacloprid undergoes particular interactions with tyrosine residues in loop C of *Lymnaea stagnalis* and *Aplysia californica* receptors, also found in insect receptors (Matsuda et al., 2009, supra). In the sequences of the *Rhipicephalus* $\alpha_5$- and $\alpha_6$ subunits identified by the inventors this tyrosine residue is also found, cf. FIG. 3 and FIG. 5.

Furthermore, imidacloprid forms CH-7c hydrogen bonds with a tryptophan ring in loop B of *Lymnaea stagnalis* and *Aplysia californica* nAChRs. The respective tryptophan moiety is highly conserved and also present in the sequences of the *Rhipicephalus* $\alpha_5$- and $\alpha_6$ subunits identified by the inventors. This tryptophan ring is not believed to be involved in the selectivity of insect nAChRs for imidacloprid (Matsuda et al., 2009, supra).

Furthermore the nitro group of imidacloprid has been found to form a hydrogen bond with a glutamine residue in loop D of *Lymnaea stagnalis* and *Aplysia californica* nAChRs. The corresponding residues of insect nAChRs are basic and thus able to tether the nitro group of neonicotinoids by an electrostatic force. An uncharged or negatively charged residues is usually found at this position in vertebrate species, and this position has been thought to play a key role in the neonicotinoid insensitivity (Erdmanis et al., Biochemistry [2012] 51, 4627-4629). Nevertheless, *Homo sapiens* $\alpha_3$- and $\alpha_4$ subunits also contain a basic residue at this position, whereas vertebrate $\alpha_7$ receptors have a glutamine at the homologue position in loop D. Imidacloprid is a partial agonist on the latter receptors. A β-subunit of a nAChR from the wolf spider, and a β-subunit of the deer tick (*Ixodes scapularis*) both contain a glutamine at this position (Erdmanis et al., 2012, supra).

In the sequences of the *Rhipicephalus* $\alpha$s subunit identified by the inventors a glutamine residue can be identified, however relative to the sequences of *Lymnaea stagnalis* and *Aplysia californica* it is moved by one position in the C-terminal direction cf. FIG. 3. At the position of the glutamine in the *Lymnaea stagnalis* and *Aplysia californica* receptors, *Rhipicephalus* $\alpha$s has an acid residue in the form of an aspartic acid side chain. The sequences of the *Rhipicephalus* $\alpha_6$ subunit identified by the inventors does not contain any a glutamine residue in expected loop D, cf. FIG. 5. Instead of a basic residue *Rhipicephalus* $\alpha$s has an acidic residue and *Rhipicephalus* $\alpha_6$ has threonine, thus providing a hydroxy group for a potential hydrogen bond. How these two residues in loop D of the *Rhipicephalus* subunits would be able to bind imidacloprid, would, however, remain speculative.

As also explained below, the *Rhipicephalus* $\alpha_5$ subunit and the *Rhipicephalus* $\alpha_6$ subunit identified by the inventors shows different characteristics in ligand binding. Responses to ACh were found to be non-desensitizing with Rma5, while responses to ACh were found to be desensitizing with Rma6. Rma6 was found to be activated by a neonicotinoid, whereas Rma5 was found to be activated by a spinosyn compound. Previous studies have shown that when the glutamine residue in loop D of chicken alpha7 is mutated to an acidic residue, the responses to imidacloprid are significantly reduced (Shimomura et al., British Journal of Pharmacology [2002] 137, 162-169). The sequence differences between *Rhipicephalus* $\alpha$s and *Rhipicephalus* $\alpha_6$, may explain differences found by the inventors, when ion currents through receptors of these two subunits were analysed.

In addition mutations of the X residue in the YXCC motif in loop C of nAChR a subunits have been identified as strongly influencing neonicotinoid sensitivity of the nAChRs (Matsuda et al., 2009, supra). *Rhipicephalus* $\alpha_5$ has a proline residue at this position, known to be sterically rigid and contributing to the formation of a turn. *Rhipicephalus* $\alpha_6$ has an alanine, providing a small nonpolar residue. In the fruit fly *Drosophila melanogaster* a proline residue can be found, while in vertebrate $\alpha_4$ subunits there is a glutamate. In *Lymnaea stagnalis* and *Aplysia californica* this position is occupied by a serine, which in *Lymnaea stagnalis* contacts a glutamine in loop F, also present in the *Rhipicephalus* subunits. In *Aplysia californica* the serine forms a hydrogen bond with the $NO_2$ of imidacloprid. In vertebrate $\alpha_2$ and $\alpha_4$ subunits, having a glutamic acid residue at this position electrostatic repulsion can be assumed when in contact with acidic residues in loop F (Matsuda et al., 2009, supra). No such repulsion can apparently be expected in the receptor subunits of *Rhipicephalus* identified by the inventors.

The expression of nAChR a subunits in oocytes is generally difficult to achieve. The present inventors were surprised to find that *Rhipicephalus* $\alpha_5$ and $\alpha_6$ subunits expressed very well. The use of nAChRs formed by these subunits is thus particularly suitable for processes of identifying and/or optimizing a compound acting as a modulator thereof, such as screening techniques.

Expression of the *Rhipicephalus* $\alpha_5$ nAChR does not seem to vary between different life stages of the tick, see FIG. 7. Accordingly, when a compound effective in modulating activity of the *Rhipicephalus* $\alpha$s nAChR is applied, the effect can be expected to equally concern adults, larvae and nymphs. Expression of the *Rhipicephalus* $\alpha_6$ nAChR is significantly up-regulated in adults compared to nymphs and larvae, see FIG. 7. If a compound effective in modulating activity of the *Rhipicephalus* $\alpha_6$ nAChR is applied, the effect can be expected to particularly concern adults, larvae and nymphs. With the parasitic phase of *Rhipicephalus microplus* being around 20 to 25 days, a repeated application after about three weeks may thus in some embodiments be advantageous. This time frame may vary for other *Rhipicephalus* ticks.

Finally, it is to be understood that *Rhipicephalus microplus* serves as an illustrative example in several passages of this document. However, provided herein are methods and agents to control various species of the genus *Rhipicephalus*. Two further illustrative examples are *Rhipicephalus annulatus* and *Rhipicephalus appendiculatus*. Yet, two further examples are *Rhipicephalus aquatilis* and *Rhipicephalus armatus*. Another example of a tick that can be controlled using a method, a use, and a compound as disclosed herein is *Rhipicephalus arnoldi*. Two more examples are *Rhipicephalus bequaerti* and *Rhipicephalus bergeoni*. Another suitable example is *Rhipicephalus boueti*. Two further examples are *Rhipicephalus bursa* and *Rhipicephalus camicasi*. Two further illustrative examples of ticks to be controlled are *Rhipicephalus capensis* and *Rhipicephalus carnivoralis*. Two more examples are *Rhipicephalus complanatus* and *Rhipicephalus compositus*. Two further examples are *Rhipicephalus congolensis* and *Rhipicephalus cuspidatus*. Another example of a tick that can be controlled is *Rhipicephalus decoloratus*. Two further examples are *Rhipicephalus deltoideus* and *Rhipicephalus distinctus*. In some embodiments the tick that is controlled is one or both of *Rhipicephalus duttoni* or *Rhipicephalus dux*. Two further examples are *Rhipicephalus evertsi* and *Rhipicephalus exophthalmos*. Two more examples are *Rhipicephalus sanguineus* and *Rhipicephalus senegalensis*. A large number of further members of the genus *Rhipicephalus* can be controlled, such as *Rhipicephalus follis, Rhipicephalus fulvus, Rhipicephalus geigyi, Rhipicephalus gertrudae, Rhipicephalus glabroscutatum, Rhipicephalus guilhoni, Rhipicephalus haemaphysaloides, Rhipicephalus hoogstraali, Rhipicephalus humeralis, Rhipicephalus hurti, Rhipicephalus interventus, Rhipicephalus jeanneli, Rhipicephalus kochi, Rhipicephalus kohlsi, Rhipicephalus leporis, Rhipicephalus longiceps, Rhipicephalus longicoxatus, Rhipicephalus longus, Rhipicephalus lounsburyi, Rhipicephalus lunulatus, Rhipicephalus maculatus, Rhipicephalus masseyi, Rhipicephalus microplus, Rhipicephalus moucheti, Rhipicephalus muehlensi, Rhipicephalus muhsamae, Rhipicephalus neumanni, Rhipicephalus nitens, Rhipicephalus oculatus, Rhipicephalus oreotragi, Rhipicephalus pilans, Rhipicephalus planus, Rhipicephalus praetextatus, Rhipi-*

*cephalus pravus, Rhipicephalus pseudolongus, Rhipicephalus pulchellus, Rhipicephalus pumilio, Rhipicephalus punctatus, Rhipicephalus pusillus, Rhipicephalus ramachandrai, Rhipicephalus rossicus, Rhipicephalus scalpturatus, Rhipicephalus schulzei, Rhipicephalus sculptus, Rhipicephalus serranoi, Rhipicephalus simpsoni, Rhipicephalus simus, Rhipicephalus sulcatus, Rhipicephalus supertritus, Rhipicephalus theileri, Rhipicephalus tricuspis, Rhipicephalus turanicus, Rhipicephalus warburtoni, Rhipicephalus zambeziensis*, and *Rhipicephalus zumpti*.

Nucleic Acid Sequences Encoding Nicotinic
Acetylcholine Receptor Subunits, and the
Corresponding Polypeptides A nucleic acid molecule provided herein may encode a polypeptide that contains an amino acid sequence that has at least about 98% sequence identity to SEQ ID NO: 10. SEQ ID NO: 10 is represented by the following sequence:

```
LVAEVDETWSARENDSSSPPPPPLSHEKRLMDSLLRHYDASVRPVKNSSE
PVIIRLGITLTQIFDLDEKNQVLTTIVWLDQEWFDEYLTWDPLEFGNFSN
LRLPCHKIWLPDIVLYNNADDYTRGYFQTRAMIDPQGRVFWPPPTKFRST
CPVDVTYFPFDDQVCTMKFGSWIYDGLQVDIQNRTSEVDLVNYMPNGEWE
LLEARMVRNVVYYPCCPDQPFPDITVVLVMRRKTLYYMYNVVLPCIMMSV
LTLLVFCLPPDSGEKIALGVTVLLAFSVFMLAIAEKMPETSESIPLLGIY
LTAVMAITSISVVMTVIVLNFHYRGPSRKEVPAWLRRLLLNKSSSSRGWF
SKPARRKTVGDNHVHFYDLPSRTAASKDRSDLDDDVDGSRRPAADDTFRL
VVDSVVIGSEDRYTRGEYAEHSASNESPSPVLHGDMSRNNASGSARHRRC
RAGAASGGSTKRVQEEVLRTLRYLMEKQQREEHLTRTVNEWRQMALVIDR
TLFWFFLIITAVSSVCFLVVIPI
```

In some embodiments a nucleic acid molecule provided herein may encode a polypeptide that contains an amino acid sequence that has at least about 99% sequence identity to SEQ ID NO: 10. The encoded polypeptide may also contain an amino acid sequence that is a fragment of a continuous length of about 150 or more amino acids. In some embodiments the encoded polypeptide may also contain an amino acid sequence that is a fragment of a continuous length of about 200 or more, such as 250 or more amino acids. In some embodiments the encoded polypeptide may contain an amino acid sequence that is a fragment of a continuous length of about 300 or more amino acids. Such a fragment represents a polypeptide, which may have at least about 98% amino acid sequence identity to SEQ ID NO: 10. In some embodiments the encoded polypeptide includes an amino acid sequence that is a fragment having at least about 99% amino acid sequence identity to SEQ ID NO: 10.

Any fragment of a polypeptide disclosed herein may include a sequence that contains two or more loops as indicated in FIG. 3 and FIG. 5. The mapping of these loops is known to the person skilled in the art, and their relevance for ligand binding has been shown (e.g. Shimomura et al., 2002, supra). A fragment may for example include a sequence that contains loops B and D. A fragment may include a sequence that contains loops C and D. In some embodiments a respective fragment may include a sequence that contains three or four loops as indicated in FIG. 3 and FIG. 5. As an example, a fragment may include a sequence that contains loops B, C and D. A fragment may also include a sequence that contains loops B, C, D and F. In some embodiments a fragment of a polypeptide disclosed herein may include a sequence that contains five loops as indicated in FIG. 3 and FIG. 5. In some embodiments a fragment of a polypeptide disclosed herein may include all six loops A to C as illustrated in FIG. 3 or FIG. 5.

In some embodiments the encoded polypeptide may contain an amino acid sequence that has at least about 99.5%, including at least about 99.8%, sequence identity to SEQ ID NO: 10. A fragment included in an encoded polypeptide may also represent a polypeptide that has at least about 99.5%, including at least about 99.8%, amino acid sequence identity to SEQ ID NO: 10.

In some embodiments a nucleic acid molecule provided herein may be a nucleic acid molecule that hybridizes to the sequence of to SEQ ID NO: 10 under stringent hybridization conditions. In some embodiments a nucleic acid molecule provided herein may be a nucleic acid molecule that hybridizes to the sequence of to SEQ ID NO: 10 under highly stringent hybridization conditions.

A nucleic acid molecule provided herein may also encode a polypeptide that contains an amino acid sequence that has at least about 98% sequence identity to SEQ ID NO: 11. SEQ ID NO: 11 is represented by the following sequence:

```
LLTAPQDSEQGAHERRLLADLLANYNTLERPVLNESEPLILSFGLTLQQI
IDVDEKNQLIITNIWLTLDWIDVNLRWNPKDYGGVQDLRIPPNKIWKPDV
LMYNSADEKFDGTYPTNVVVRSNGSCNYIPPGIFKSTCKIDITWFPFDDQ
KCDLKFGSWTYHGYQLDLRVNSEEGGDLTTYIPNGEWDLIGVPGVRNVRE
YACCPEPYIDITYTIHIRRRTLYYGFNLIIPCVLISSMTLLGFTLPPDTG
ERLTLGVTILLSLTVFMLQLAETMPPTSDAVSIIGTYFACIMIMVAFSVV
MTVVVLNYHHRNQETTEMPALIRTVFLVWLPWLLRMEPPGQKANRRSLFL
NSKMKELELKERSSRSLLANVLDI
```

In some embodiments a nucleic acid molecule provided herein may encode a polypeptide that contains an amino acid sequence that has at least about 96% sequence identity to SEQ ID NO: 11. The encoded polypeptide may also contain an amino acid sequence that is a fragment of a continuous length of about 150 or more amino acids. In some embodiments the encoded polypeptide may also contain an amino acid sequence that is a fragment of a continuous length of about 200 or more, such as about 250 or more amino acids. In some embodiments the encoded polypeptide may contain an amino acid sequence that is a fragment of a continuous length of about 300 or more amino acids. Such a fragment represents a polypeptide, which may have at least about 95%, such as about 96% amino acid sequence identity to SEQ ID NO: 11. In some embodiments the encoded polypeptide includes an amino acid sequence that is a fragment having at least about 95%, such as about 96% amino acid sequence identity to SEQ ID NO: 11.

In some embodiments an amino acid sequence of the sequence of SEQ ID NO: 11 is included in a sequence of SEQ ID NO: 11. A nucleic acid molecule as described herein may in some embodiments encode a polypeptide that contains an amino acid sequence that has at least about 94% sequence identity to SEQ ID NO: 11.

A nucleic acid molecule provided herein may in some embodiments encode a polypeptide that contains an amino acid sequence that has at least about 98% sequence identity to SEQ ID NO: 12. SEQ ID NO: 12 is represented by the following sequence:

IAVLLTAPQDSEQGAHERRLLADLLANYNTLERPVLNESEPLILSFGLTL

QQIIDVDEKNQLIITNIWLTLDWIDVNLRWNPKDYGGVQDLRIPPNKIWK

PDVLMYNSADEKFDGTYPTNVVVRSNGSCNYIPPGIFKSTCKIDITWFPF

DDQKCDLKFGSWTYHGYQLDLRVNSEEGGDLTTYIPNGEWDLIGVPGVRN

VREYACCPEPYIDITYTIHIRRRTLYYGFNLIIPCVLISSMTLLGFTLPP

DTGERLTLGVTILLSLTVFMLQLAETMPPTSDAVSIIGTYFACIMIMVAF

SVVMTVVVLNYHHRNQETTEMPALIRTVFLVWLPWLLRMEPPGQKANRRS

LFLNSKMKELELKERSSRSLLANVLDID

In some embodiments a nucleic acid molecule provided herein may encode a polypeptide that contains an amino acid sequence that has at least about 96% sequence identity to SEQ ID NO: 12. The encoded polypeptide may also contain an amino acid sequence that is a fragment of a continuous length of about 150 or more amino acids. In some embodiments the encoded polypeptide may also contain an amino acid sequence that is a fragment of a continuous length of about 200 or more, such as about 250 or more amino acids. In some embodiments the encoded polypeptide may contain an amino acid sequence that is a fragment of a continuous length of about 300 or more amino acids. Such a fragment represents a polypeptide, which may have at least 95%, such as about 96% amino acid sequence identity to SEQ ID NO: 12. In some embodiments the encoded polypeptide includes an amino acid sequence that is a fragment having at least about 95%, such as about 96% amino acid sequence identity to SEQ ID NO: 12.

A nucleic acid molecule provided herein may also encode a polypeptide that contains an amino acid sequence that has at least about 98% sequence identity to SEQ ID NO: 13. SEQ ID NO: 13 is represented by the following sequence:

LLTAPQDSEQGAHERRLLADLLANYNTLERPVLNESEPLILSFGLTLQQI

IDVDEKNQIITTNVWLNLDWIDVNLRWNPKDYGGVQDLRIPPNKIWKPDV

LMYNSADEKFDGTYPTNVVVRSNGSCNYIPPGIFKSTCKIDITWFPFDDQ

KCDLKFGSWTYHGYQLDLRVNSEEGGDLTTYIPNGEWDLIGVPGVRNVRE

YACCPEPYIDITYTIHIRRRTLYYGFNLIIPCVLISSMTLLGFTLPPDTG

ERLTLGVTILLSLTVFMLQLAETMPPTSDAVSIIGTYFACIMIMVAFSVV

MTVVVLNYHHRNQETTEMPALIRTVFLVWLPWLLRMEPPGQKANRRSLFL

NSKMKELELKERSSRSLLANVLDI

In some embodiments a nucleic acid molecule provided herein may encode a polypeptide that contains an amino acid sequence that has at least about 96% sequence identity to SEQ ID NO: 13. The encoded polypeptide may also contain an amino acid sequence that is a fragment of a continuous length of about 150 or more amino acids. In some embodiments the encoded polypeptide may also contain an amino acid sequence that is a fragment of a continuous length of about 200 or more, such as about 250 or more amino acids. In some embodiments the encoded polypeptide may contain an amino acid sequence that is a fragment of a continuous length of about 300 or more amino acids. Such a fragment represents a polypeptide, which may have at least 95%, such as about 96% amino acid sequence identity to SEQ ID NO: 13. In some embodiments the encoded polypeptide includes an amino acid sequence that is a fragment having at least about 95%, such as about 96% amino acid sequence identity to SEQ ID NO: 13.

In some embodiments an amino acid sequence of the sequence of SEQ ID NO: 13 is included in a sequence of SEQ ID NO: 14. A nucleic acid molecule as described herein may in some embodiments encode a polypeptide, which contains an amino acid sequence that has at least about 94% sequence identity to SEQ ID NO: 14.

A nucleic acid molecule provided herein may in some embodiments encode a polypeptide that contains an amino acid sequence that has at least about 98% sequence identity to SEQ ID NO: 14. SEQ ID NO: 14 is represented by the following sequence:

IAVLLTAPQDSEQGAHERRLLADLLANYNTLERPVLNESEPLILSFGLTL

QQIIDVDEKNQIITTNVWLNLDWIDVNLRWNPKDYGGVQDLRIPPNKIWK

PDVLMYNSADEKFDGTYPTNVVVRSNGSCNYIPPGIFKSTCKIDITWFPF

DDQKCDLKFGSWTYHGYQLDLRVNSEEGGDLTTYIPNGEWDLIGVPGVRN

VREYACCPEPYIDITYTIHIRRRTLYYGFNLIIPCVLISSMTLLGFTLPP

DTGERLTLGVTILLSLTVFMLQLAETMPPTSDAVSIIGTYFACIMIMVAF

SVVMTVVVLNYHHRNQETTEMPALIRTVFLVWLPWLLRMEPPGQKANRRS

LFLNSKMKELELKERSSRSLLANVLDID

In some embodiments a nucleic acid molecule provided herein may contain an amino acid sequence that has at least about 96% sequence identity to SEQ ID NO: 14. The encoded polypeptide may also contain an amino acid sequence that is a fragment of a continuous length of about 150 or more amino acids. In some embodiments the encoded polypeptide may also contain an amino acid sequence that is a fragment of a continuous length of about 200 or more, such as about 250 or more amino acids. In some embodiments the encoded polypeptide may contain an amino acid sequence that is a fragment of a continuous length of about 300 or more amino acids. Such a fragment represents a polypeptide, which may have at least 95%, such as about 96% amino acid sequence identity to SEQ ID NO: 14. In some embodiments the encoded polypeptide includes an amino acid sequence that is a fragment having at least about 95%, such as about 96% amino acid sequence identity to SEQ ID NO: 14.

In some embodiments a nucleic acid molecule provided herein may contain an amino acid sequence that has at least about 99%, including at least about 99.5% sequence identity to SEQ ID NO: 2. In some embodiments a nucleic acid molecule provided herein may essentially consist of an amino acid sequence that has at least about 99%, including at least about 99.5% sequence identity to SEQ ID NO: 2. In some embodiments a nucleic acid molecule provided herein may consist of an amino acid sequence that has at least about 99%, including at least about 99.5% sequence identity to SEQ ID NO: 2.

In some embodiments a nucleic acid molecule provided herein may contain an amino acid sequence that has at least about 99%, including at least about 99.5% sequence identity to SEQ ID NO: 4. In some embodiments a nucleic acid molecule provided herein may essentially consist of an amino acid sequence that has at least about 99%, including at least about 99.5% sequence identity to SEQ ID NO: 4. In some embodiments a nucleic acid molecule provided herein may consist of an amino acid sequence that has at least about 99%, including at least about 99.5% sequence identity to SEQ ID NO: 4.

In some embodiments a nucleic acid molecule provided herein may contain an amino acid sequence that has at least about 99%, including at least about 99.5% sequence identity to SEQ ID NO: 6. In some embodiments a nucleic acid molecule provided herein may essentially consist of an amino acid sequence that has at least about 99%, including at least about 99.5% sequence identity to SEQ ID NO: 6. In some embodiments a nucleic acid molecule provided herein may consist of an amino acid sequence that has at least about 99%, including at least about 99.5% sequence identity to SEQ ID NO: 6.

A fragment included in a polypeptide provided herein may in some embodiments represent a polypeptide, which may have about 99%, including at least about 99.5% sequence identity to SEQ ID NO: 2. A fragment included in a polypeptide provided herein may in some embodiments represent a polypeptide, which may have about 99%, including at least about 99.5% sequence identity to SEQ ID NO: 4. In some embodiments a fragment included in a polypeptide provided herein may represent a polypeptide, which may have about 99%, including at least about 99.5% sequence identity to SEQ ID NO: 6.

In some embodiments a nucleic acid molecule encoding a polypeptide provided herein may contain a nucleic acid sequence that has at least about 99%, including at least about 99.5% sequence identity to SEQ ID NO: 15. SEQ ID NO: 15 is represented by the following sequence:

CTCGTGGCCGAGGTGGACGAGACGTGGTCGGCTCGCGAGAACGACTCCTC

GTCGCCGCCGCCGCCGCCACTGAGTCACGAGAAGCGGCTGATGGACTCGC

TGCTGCGCCACTACGACGCCAGCGTGAGGCCCGTCAAGAACTCCTCGGAG

CCCGTCATCATTCGGCTGGGCATCACGCTCACGCAGATATTCGACCTGGA

CGAGAAGAATCAAGTCCTAACAACCATCGTTTGGCTTGACCAGGAATGGT

TCGACGAGTACCTCACTTGGGACCCGTTGGAGTTTGGAAACTTCAGCAAC

CTCAGGCTGCCCTGCCACAAGATTTGGCTGCCTGACATCGTTCTCTACAA

CAACGCGGACGACTACACGCGGGGCTACTTCCAGACGCGCGCCATGATCG

ACCCCCAGGGCCGAGTGTTCTGGCCGCCACCCACCAAGTTTCGCAGCACC

TGCCCGGTGGACGTAACGTACTTCCCTTTCGACGACCAGGTCTGCACAAT

GAAGTTCGGTTCTTGGATCTATGACGGGCTACAAGTGGACATCCAGAACC

GGACATCCGAGGTTGACCTGGTCAATTACATGCCCAACGGCGAGTGGGAG

CTGCTTGAGGCACGCATGGTGCGCAACGTGGTCTACTACCCTTGCTGTCC

AGACCAGCCGTTCCCGGACATCACCGTGGTCTTGGTCATGAGGCGCAAGA

CGCTCTACTACATGTACAACGTGGTCCTGCCCTGCATCATGATGTCTGTG

CTGACTCTGCTCGTCTTCTGCCTACCGCCGGACTCGGGCGAGAAGATCGC

GCTCGGCGTCACAGTGCTGCTAGCATTCTCCGTGTTCATGCTGGCCATAG

CGGAGAAGATGCCCGAGACATCGGAGTCCATACCCTTACTGGGAATATAC

CTGACGGCCGTGATGGCCATCACGTCCATCTCGGTCGTCATGACCGTGAT

CGTCCTCAACTTCCACTACCGCGGCCCCAGCCGGAAAGAAGTGCCAGCGT

GGCTCCGCCGTCTCCTGCTCAACAAGTCATCCTCCAGTCGTGGTTGGTTC

TCGAAGCCGGCGCGCCGCAAGACCGTCGGCGACAATCACGTGCACTTCTA

CGACTTGCCATCGCGCACAGCAGCCTCCAAGGACCGCTCAGACCTGGACG

ACGACGTAGACGGCAGCAGAAGACCTGCGGCCGACGACACCTTCCGGCTC

GTCGTGGACAGCGTCGTGATCGGCAGCGAAGACCGCTACACTCGCGGCGA

GTACGCCGAGCACTCCGCGAGCAACGAGTCCCCGAGTCCCGTCCTCCACG

GCGACATGTCGCGGAACAATGCCTCCGGGTCGGCCAGGCACCGCCGCTGT

CGCGCTGGTGCCGCTAGTGGCGGATCCACTAAGCGCGTGCAGGAAGAAGT

GCTGCGGACTTTGCGGTACCTGATGGAGAAACAGCAGCGCGAGGAGCACC

TCACCCGGACTGTGAACGAGTGGAGACAGATGGCTCTCGTGATAGATCGC

ACCTTGTTCTGGTTCTTTCTGATCATCACAGCCGTGTCATCCRTCTGCTT

CCTAGTCGTCATACCCATA

In some embodiments a nucleic acid molecule encoding a polypeptide provided herein may essentially consist of a acid sequence that has at least about 99%, including at least about 99.5% sequence identity to SEQ ID NO: 15. In some embodiments a nucleic acid molecule encoding a polypeptide provided herein may consist of a nucleic acid sequence that has at least about 99%, including at least about 99.5% sequence identity to SEQ ID NO: 15.

A nucleic acid molecule encoding a polypeptide provided herein may be a nucleic acid molecule that hybridizes to the sequence SEQ ID NO: 15 under stringent hybridization conditions. In some embodiments a nucleic acid molecule provided herein may be a nucleic acid molecule that hybridizes to the sequence of to SEQ ID NO: 15 under highly stringent hybridization conditions.

In some embodiments a nucleic acid molecule encoding a polypeptide provided herein may contain a nucleic acid sequence that has at least about 99%, including at least about 99.5% sequence identity to SEQ ID NO: 16. SEQ ID NO: 16 is represented by the following sequence:

CTGCTCACCGCGCCTCAGGACTCTGAACAAGGCGCGCACGAGCGGCGGCT

TCTGGCAGACCTGCTGGCCAACTACAACACCCTGGAGCGGCCCGTGCTCA

ACGAGTCGGAGCCGCTCATCCTCAGCTTCGGGCTCACACTGCAGCAGATC

ATAGACGTCGACGAAAAGAATCAGCTAATTATTACAAATATCTGGTTAAC

ATTGGATTGGATAGATGTGAATCTACGTTGGAACCCAAAAGACTACGGCG

GAGTGCAGGACCTGCGTATTCCGCCAAACAAAATTTGGAAGCCTGACGTG

CTCATGTACAACAGCGCGGACGAAAAGTTCGACGGCACGTACCCGACCAA

CGTGGTCGTGCGGAGCAACGGCAGTTGCAACTACATCCCTCCTGGCATCT

TTAAGAGCACGTGCAAGATCGACATTACGTGGTTCCCTTTTGACGATCAG

AAGTGCGACCTGAAGTTCGGCTCCTGGACCTATCACGGTTATCAGCTGGA

CCTTCGTGTCAACAGTGAGGAAGGCGGGGATCTGACTACCTACATTCCCA

ATGGCGAGTGGGACCTGATAGGCGTGCCGGGAGTGCGCAACGTTCGCGAG

TATGCCTGCTGTCCGGAGCCGTACATCGACATCACGTACACCATCCACAT

CCGGCGGCGCACGCTCTACTACGGCTTCAACCTCATCATTCCCTGCGTGC

TCATCTCGTCCATGACTCTGCTCGGTTTCACGCTGCCCCCCGACACCGGA

```
GAGAGGCTCACCCTGGGTGTAACCATTTTGCTGTCCCTGACGGTATTCAT

GCTCCAGCTCGCCGAGACCATGCCTCCGACGTCCGATGCTGTCTCCATAA

TAGGAACTTATTTTGCCTGCATCATGATCATGGTTGCCTTTTCGGTGGTC

ATGACCGTGGTGGTCCTGAACTATCATCACAGAAATCAAGAGACGACCGA

AATGCCTGCTTTGATTCGCACGGTGTTCCTGGTGTGGCTCCCGTGGCTTC

TGCGCATGGAGCCTCCGGGCCAGAAGGCGAACAGGCGCAGCCTCTTCCTC

AACAGCAAGATGAAAGAGCTCGAGCTGAAGGAGCGCTCATCGCGGAGTCT

GCTGGCCAACGTGCTGGACATC
```

In some embodiments a nucleic acid molecule encoding a polypeptide provided herein may essentially consist of a nucleic acid sequence that has at least about 99%, including at least about 99.5% sequence identity to SEQ ID NO: 16. In some embodiments a nucleic acid molecule encoding a polypeptide provided herein may consist of a nucleic acid sequence that has at least about 99%, including at least about 99.5% sequence identity to SEQ ID NO: 16.

A nucleic acid molecule encoding a polypeptide provided herein may be a nucleic acid molecule that hybridizes to the sequence SEQ ID NO: 16 under stringent hybridization conditions. In some embodiments a nucleic acid molecule provided herein may be a nucleic acid molecule that hybridizes to the sequence of to SEQ ID NO: 16 under highly stringent hybridization conditions.

In some embodiments a nucleic acid molecule encoding a polypeptide provided herein may contain a nucleic acid sequence that has at least about 99%, including at least about 99.5% sequence identity to SEQ ID NO: 17. SEQ ID NO: 17 is represented by the following sequence:

```
ATCGCCGTGCTGCTCACCGCGCCTCAGGACTCTGAACAAGGCGCGCACGA

GCGGCGGCTTCTGGCAGACCTGCTGGCCAACTACAACACCCTGGAGCGGC

CCGTGCTCAACGAGTCGGAGCCGCTCATCCTCAGCTTCGGGCTCACACTG

CAGCAGATCATAGACGTCGACGAAAAGAATCAGCTAATTATTACAAATAT

CTGGTTAACATTGGATTGGATAGATGTGAATCTACGTTGGAACCCAAAAG

ACTACGGCGGAGTGCAGGACCTGCGTATTCCGCCAAACAAAATTTGGAAG

CCTGACGTGCTCATGTACAACAGCGCGGACGAAAAGTTCGACGGCACGTA

CCCGACCAACGTGGTCGTGCGGAGCAACGGCAGTTGCAACTACATCCCTC

CTGGCATCTTTAAGAGCACGTGCAAGATCGACATTACGTGGTTCCCTTTT

GACGATCAGAAGTGCGACCTGAAGTTCGGCTCCTGGACCTATCACGGTTA

TCAGCTGGACCTTCGTGTCAACAGTGAGGAAGGCGGGGATCTGACTACCT

ACATTCCCAATGGCGAGTGGGACCTGATAGGCGTGCCGGGAGTGCGCAAC

GTTCGCGAGTATGCCTGCTGTCCGGAGCCGTACATCGACATCACGTACAC

CATCCACATCCGGCGGCGCACGCTCTACTACGGCTTCAACCTCATCATTC

CCTGCGTGCTCATCTCGTCCATGACTCTGCTCGGTTTCACGCTGCCCCCC

GACACCGGAGAGGCTCACCCTGGGTGTAACCATTTTGCTGTCCCTGAC

GGTATTCATGCTCCAGCTCGCCGAGACCATGCCTCCGACGTCCGATGCTG

TCTCCATAATAGGAACTTATTTTGCCTGCATCATGATCATGGTTGCCTTT

TCGGTGGTCATGACCGTGGTGGTCCTGAACTATCATCACAGAAATCAAGA

GACGACCGAAATGCCTGCTTTGATTCGCACGGTGTTCCTGGTGTGGCTCC

CGTGGCTTCTGCGCATGGAGCCTCCGGGCCAGAAGGCGAACAGGCGCAGC

CTCTTCCTCAACAGCAAGATGAAAGAGCTCGAGCTGAAGGAGCGCTCATC

GCGGAGTCTGCTGGCCAACGTGCTGGACATCGAC
```

In some embodiments a nucleic acid molecule encoding a polypeptide provided herein may essentially consist of a nucleic acid sequence that has at least about 99%, including at least about 99.5% sequence identity to SEQ ID NO: 17. In some embodiments a nucleic acid molecule encoding a polypeptide provided herein may consist of a nucleic acid sequence that has at least about 99%, including at least about 99.5% sequence identity to SEQ ID NO: 17.

A nucleic acid molecule encoding a polypeptide provided herein may be a nucleic acid molecule that hybridizes to the sequence SEQ ID NO: 17 under stringent hybridization conditions. In some embodiments a nucleic acid molecule provided herein may be a nucleic acid molecule that hybridizes to the sequence of to SEQ ID NO: 17 under highly stringent hybridization conditions.

In some embodiments a nucleic acid molecule encoding a polypeptide provided herein may contain a nucleic acid sequence that has at least about 99%, including at least about 99.5% sequence identity to SEQ ID NO: 18. SEQ ID NO: 18 is represented by the following sequence:

```
CTGCTCACCGCGCCTCAGGACTCTGAACAAGGCGCGCACGAGCGGCGGCT

TCTGGCAGACCTGCTGGCCAACTACAACACCCTGGAGCGGCCCGTGCTCA

ACGAGTCGGAGCCGCTCATCCTCAGCTTCGGGCTCACACTGCAGCAGATC

ATAGACGTCGACGAAAAGAATCAAATAATAACAACAAACGTGTGGTTAAA

TCTGGATTGGATAGATGTGAATCTACGTTGGAACCCAAAAGACTACGGCG

GAGTGCAGGACCTGCGTATTCCGCCAAACAAAATTTGGAAGCCTGACGTG

CTCATGTACAACAGCGCGGACGAAAAGTTCGACGGCACGTACCCGACCAA

CGTGGTCGTGCGGAGCAACGGCAGTTGCAACTACATCCCTCCTGGCATCT

TTAAGAGCACGTGCAAGATCGACATTACGTGGTTCCCTTTTGACGATCAG

AAGTGCGACCTGAAGTTCGGCTCCTGGACCTATCACGGTTATCAGCTGGA

CCTTCGTGTCAACAGTGAGGAAGGCGGGGATCTGACTACCTACATTCCCA

ATGGCGAGTGGGACCTGATAGGCGTGCCGGGAGTGCGCAACGTTCGCGAG

TATGCCTGCTGTCCGGAGCCGTACATCGACATCACGTACACCATCCACAT

CCGGCGGCGCACGCTCTACTACGGCTTCAACCTCATCATTCCCTGCGTGC

TCATCTCGTCCATGACTCTGCTCGGTTTCACGCTGCCCCCCGACACCGGA

GAGAGGCTCACCCTGGGTGTAACCATTTTGCTGTCCCTGACGGTATTCAT

GCTCCAGCTCGCCGAGACCATGCCTCCGACGTCCGATGCTGTCTCCATAA

TAGGAACTTATTTTGCCTGCATCATGATCATGGTTGCCTTTTCGGTGGTC

ATGACCGTGGTGGTCCTGAACTATCATCACAGAAATCAAGAGACGACCGA

AATGCCTGCTTTGATTCGCACGGTGTTCCTGGTGTGGCTCCCGTGGCTTC
```

-continued

```
TGCGCATGGAGCCTCCGGGCCAGAAGGCGAACAGGCGCAGCCTCTTCCTC

AACAGCAAGATGAAAGAGCTCGAGCTGAAGGAGCGCTCATCGCGGAGTCT

GCTGGCCAACGTGCTGGACATC
```

In some embodiments a nucleic acid molecule encoding a polypeptide provided herein may essentially consist of a nucleic acid sequence that has at least about 99%, including at least about 99.5% sequence identity to SEQ ID NO: 18. In some embodiments a nucleic acid molecule encoding a polypeptide provided herein may consist of a nucleic acid sequence that has at least about 99%, including at least about 99.5% sequence identity to SEQ ID NO: 18.

A nucleic acid molecule encoding a polypeptide provided herein may be a nucleic acid molecule that hybridizes to the sequence SEQ ID NO: 18 under stringent hybridization conditions. In some embodiments a nucleic acid molecule provided herein may be a nucleic acid molecule that hybridizes to the sequence of to SEQ ID NO: 18 under highly stringent hybridization conditions.

In some embodiments a nucleic acid molecule encoding a polypeptide provided herein may contain a nucleic acid sequence that has at least about 99%, including at least about 99.5% sequence identity to SEQ ID NO: 19. SEQ ID NO: 19 is represented by the following sequence:

```
ATCGCCGTGCTGCTCACCGCGCCTCAGGACTCTGAACAAGGCGCGCACGA

GCGGCGGCTTCTGGCAGACCTGCTGGCCAACTACAACACCCTGGAGCGGC

CCGTGCTCAACGAGTCGGAGCCGCTCATCCTCAGCTTCGGGCTCACACTG

CAGCAGATCATAGACGTCGACGAAAAGAATCAAATAATAACAACAAACGT

GTGGTTAAATCTGGATTGGATAGATGTGAATCTACGTTGGAACCCAAAAG

ACTACGGCGGAGTGCAGGACCTGCGTATTCCGCCAAACAAAATTTGGAAG

CCTGACGTGCTCATGTACAACAGCGCGGACGAAAAGTTCGACGGCACGTA

CCCGACCAACGTGGTCGTGCGGAGCAACGGCAGTTGCAACTACATCCCTC

CTGGCATCTTTAAGAGCACGTGCAAGATCGACATTACGTGGTTCCCTTTT

GACGATCAGAAGTGCGACCTGAAGTTCGGCTCCTGGACCTATCACGGTTA

TCAGCTGGACCTTCGTGTCAACAGTGAGGAAGGCGGGGATCTGACTACCT

ACATTCCCAATGGCGAGTGGGACCTGATAGGCGTGCCGGGAGTGCGCAAC

GTTCGCGAGTATGCCTGCTGTCCGGAGCCGTACATCGACATCACGTACAC

CATCCACATCCGGCGGCGCACGCTCTACTACGGCTTCAACCTCATCATTC

CCTGCGTGCTCATCTCGTCCATGACTCTGCTCGGTTTCACGCTGCCCCCC

GACACCGGAGAGAGGCTCACCCTGGGTGTAACCATTTTGCTGTCCCTGAC

GGTATTCATGCTCCAGCTCGCCGAGACCATGCCTCCGACGTCCGATGCTG

TCTCCATAATAGGAACTTATTTTGCCTGCATCATGATCATGGTTGCCTTT

TCGGTGGTCATGACCGTGGTGGTCCTGAACTATCATCACAGAAATCAAGA

GACGACCGAAATGCCTGCTTTGATTCGCACGGTGTTCCTGGTGTGGCTCC

CGTGGCTTCTGCGCATGGAGCCTCCGGGCCAGAAGGCGAACAGGCGCAGC

CTCTTCCTCAACAGCAAGATGAAAGAGCTCGAGCTGAAGGAGCGCTCATC

GCGGAGTCTGCTGGCCAACGTGCTGGACATCGAC
```

In some embodiments a nucleic acid molecule encoding a polypeptide provided herein may essentially consist of a nucleic acid sequence that has at least about 99%, including at least about 99.5% sequence identity to SEQ ID NO: 19. In some embodiments a nucleic acid molecule encoding a polypeptide provided herein may consist of a nucleic acid sequence that has at least about 99%, including at least about 99.5% sequence identity to SEQ ID NO: 19.

A nucleic acid molecule encoding a polypeptide provided herein may be a nucleic acid molecule that hybridizes to the sequence SEQ ID NO: 19 under stringent hybridization conditions. In some embodiments a nucleic acid molecule provided herein may be a nucleic acid molecule that hybridizes to the sequence of to SEQ ID NO: 19 under highly stringent hybridization conditions.

A nucleic acid molecule provided herein may also contain a nucleotide sequence that has about 99% or more, including about 99.5% or more, sequence identity to a fragment of at least about 600 bases of SEQ ID NO: 15. In some embodiments a nucleic acid molecule provided herein may also contain a nucleotide sequence that has about 99% or more, including about 99.5% or more, sequence identity to a fragment of at least about 850 bases of SEQ ID NO: 15. A nucleic acid molecule provided herein may furthermore contain a nucleotide sequence that has about 99% or more, including about 99.5% or more, sequence identity to a fragment of at least about 600 bases of SEQ ID NO: 16. In some embodiments a nucleic acid molecule provided herein may also contain a nucleotide sequence that has about 99% or more, including about 99.5% or more, sequence identity to a fragment of at least about 850 bases of SEQ ID NO: 16.

A nucleic acid molecule disclosed in this specification may also contain a nucleotide sequence that has about 99% or more, including about 99.5% or more, sequence identity to a fragment of at least about 600 bases of SEQ ID NO: 17. In some embodiments a nucleic acid molecule provided herein may also contain a nucleotide sequence that has about 99% or more, including about 99.5% or more, sequence identity to a fragment of at least about 850 bases of SEQ ID NO: 17. A nucleic acid molecule provided herein may also contain a nucleotide sequence that has about 99% or more, including about 99.5% or more, sequence identity to a fragment of at least about 600 bases of SEQ ID NO: 18. In some embodiments a nucleic acid molecule provided herein may also contain a nucleotide sequence that has about 99% or more, including about 99.5% or more, sequence identity to a fragment of at least about 850 bases of SEQ ID NO: 18. A nucleic acid molecule disclosed herein may furthermore contain a nucleotide sequence that has about 99% or more, including about 99.5% or more, sequence identity to a fragment of at least about 600 bases of SEQ ID NO: 19. In some embodiments a nucleic acid molecule provided herein may also contain a nucleotide sequence that has about 99% or more, including about 99.5% or more, sequence identity to a fragment of at least about 850 bases of SEQ ID NO: 19.

In certain embodiments variants of a nucleic acid sequence or a polypeptide disclosed herein are contemplated. For example, it may be negligible to exchange certain amino acid residues that are nor critical for binding of a ligand. It may also be modify a polypeptide at one or more positions for detection purposes. Typically the difference from a given nucleic acid sequence or a polypeptide is a substitution. In some embodiments the difference from a given nucleic acid sequence or polypeptide is a deletion. A variant of a polypeptide provided herein may be a polypeptide obtained from the expression of a gene sequence altered by site-specific mutagenesis.

Variants of a polypeptide provided herein may be prepared by protein and/or chemical engineering, introducing appropriate modifications into the nucleic acid sequence encoding the polypeptide, or by protein/peptide synthesis. A variant may be obtained by any combination(s) of one or more deletions, substitutions, additions and insertions to nucleic acid and/or the amino acid sequence, provided that the obtained polypeptide defines a functional nACh receptor subunit. In some embodiments a variant of a polypeptide provided herein differs from a particular sequence of a polypeptide provided herein by up to five substitutions. A substitution in an amino acid sequence of a polypeptide provided herein may be a conservative substitution. Examples of conservative substitutions include:
1. Substituting alanine (A) by valine (V);
2. Substituting arginine (R) by lysine (K);
3. Substituting asparagine (N) by glutamine (Q);
4. Substituting aspartic acid (D) by glutamic acid (E);
5. Substituting cysteine (C) by serine (S);
6. Substituting glutamic acid (E) by aspartic acid (D);
7. Substituting glycine (G) by alanine (A);
8. Substituting histidine (H) by arginine (R) or lysine (K);
9. Substituting isoleucine (I) by leucine (L);
10. Substituting methionine (M) by leucine (L);
11. Substituting phenylalanine (F) by tyrosine (Y);
12. Substituting proline (P) by alanine (A);
13. Substituting serine (S) by threonine (T);
14. Substituting tryptophan (W) by tyrosine (Y);
15. Substituting phenylalanine (F) by tryptophan (W); and/or
16. Substituting valine (V) by leucine (L) and vice versa.

The sequences described herein may include one or more, such as two or three of such conservative substitutions. In some embodiments a polypeptide according to this disclosure includes a sequence that has four or more conservative substitutions in comparison to a sequence disclosed herein. In some embodiments a polypeptide includes a sequence that has five or more conservative substitutions. In some embodiments a polypeptide contains six or more, such as seven or more conservative substitutions relative to a sequence disclosed herein. In some embodiments a polypeptide may include eight or nine such conservative substitutions. In some embodiments a polypeptide according to this disclosure may include ten or more such conservative substitutions, e.g. eleven, twelve or more of such conservative substitutions.

Non-conservative substitutions may lead to more substantial changes, e.g., with respect to the charge, dipole moment, size, hydrophilicity, hydrophobicity or conformation of the polypeptide. In some embodiments the polypeptide includes one or more, such as two non-conservative substitutions. In some embodiments the polypeptide includes three or four non-conservative substitutions. The polypeptide may also include five or more, e.g. six, seven, eight, nine, ten, eleven, twelve or more of such non-conservative substitutions.

Noteworthy, the present inventors have identified two splice variants of R. microplus nAChRα$_6$. The corresponding amino acid sequences have SEQ ID NO: 4 and SEQ ID NO: 6, as depicted in FIG. 5 and FIG. 17. Splice variants can be regarded variants as described above. The presence of differently spliced variant subunits is important because the receptors may have different pharmacological profile and/or the variants can be expressed preferentially in different tissues/life stages (Hosie et al., Neuroscience [2001]102, 3: 709-714; Kita et al., Biochem Mol Biol [2014] 45: 1-10). Alternative splice transcripts of nAChRα$_6$ subunit have been previously characterised in insects (e.g. Grauso et al., Genetics [2002] 160, 4: 1519-1533; Rinkevich and Scott, Insect Molecular Biology [2009] 18(2): 233-242; Puinean et al., J Neurochem [2013]124(5): 590-601) with different isoforms found for exons 3 and 8. In the tick *R. microplus* two alternative variants of exon 3 were found following transcript sequencing and were named 3a (SEQ ID NO: 5) and 3b (SEQ ID NO: 3) in consensus with the annotation used in other studies. Both isoforms form functional receptors when expressed in *Xenopus* oocytes.

Identifying Suitable Compounds

In a method of identifying a compound capable of modulating activity of a *Rhipicephalus* nACh receptor a variety of techniques known in the art can be employed. Such techniques typically allow the formation of a detectable electrophysiological response to a known agonist. The respective response may be detected in the form of measurements of ionic currents. Automated electrophysiology instruments using planar arrays are commercially available to perform this task. Since an ion flux through a channel affects membrane potential, the respective response may also be detected using an electrophysiological method. As an example, conventional patch-clamp electrophysiology measurements can be employed. Changes in membrane potential may also be detected using a dye system, for example using a fluorescent dye. A fluorescent plate reader with kinetic capabilities may for instance be employed in this regard. 96-, 384-, or 1536-well plate formats may be used. The respective response may also be detected on the basis of a change in ion concentration on one side of a membrane. This may be achieved by an electromagnetic signal, for instance by means of a sensor dye that indicates the presence and/or absence of certain metal ions. Again, 96-, 384-, or 1536-well plates may be employed. An ion flux may for instance be detected using well-established genetically encoded ion flux indicators such as a chemiluminescent ion sensor, aequorin and an engineered fluorescent protein. An ion concentration may also be measured directly using atomic absorption spectroscopy or labelled isotopes.

Where one or more membrane potential sensing dyes are used, fluorescence resonance energy transfer (FRET) can be exploited if a pair of dyes is used. A phospholipid-anchored first dye such as a coumarin and a second hydrophobic dye that rapidly redistributes in the membrane according to the transmembrane field may be used.

Where desired, a physiological ion that permeates the nACh receptor in vivo may be replaced by a non-physiological ion that can permeate the pore defining a channel. As an illustration, thallium readily permeates many potassium channels and can be detected with fluorescent probes that can be loaded into cells.

To take account of conformational changes during gating it may be desired to use an assay format that can control channel gating in order to identify a compound with functional selectivity. In this regard techniques in automated electrophysiology, biochemical sensors, and plate readers provide a range of options for implementing an ion channel assay that can detect state-specific, or state-independent, channel modulation.

As an example, cells or oocytes expressing a polypeptide as disclosed herein in recombinant form can be contacted with a test compound, and the modulating effect(s) thereof can then be evaluated by comparing the AChR-mediated response in the presence and absence of the test compound. The AChR-mediated response of test cells, or control cells, typically cells that do not express nAChRs at all or cells that do not express a polypeptide as disclosed herein, may also be compared to the presence of the compound.

In accordance with a particular embodiment of the method, a detectable electrophysiological response may be produced in a cell such as an oocyte. The method generally includes expressing a polypeptide as disclosed herein on a cell surface, such as an oocyte cell surface. The method may also include contacting the oocyte with one or more test compounds, and identifying the electrophysiological response.

A method as disclosed herein may include introducing a nucleic acid molecule into a suitable host cell. Respective techniques are well established in the art. In some embodiments a nucleic acid as disclosed herein may be included in an expression cassette. An expression cassette generally includes a promoter operatively linked to the nucleotide sequence of interest, which is operatively linked to one or more termination signals. It may also include sequences required for proper translation of the nucleotide sequence. The coding region can encode a polypeptide of interest and can also encode a functional RNA of interest, including but not limited to, antisense RNA or a non-translated RNA, in the sense or antisense direction. The expression cassette that contains the nucleotide sequence of interest can be chimeric, meaning that at least one of its components is heterologous with respect to at least one of its other components. The expression cassette can also be one that is naturally occurring but has been obtained in a recombinant form useful for heterologous expression. In some embodiments the expression cassette may be heterologous with respect to the host; i.e., the particular nucleic acid sequence of the expression cassette does not occur naturally in the host cell and was introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism such as a plant or an animal, the promoter can also be specific to a particular tissue, organ, or stage of development In some embodiments a nucleic acid molecule as described herein, e.g. an RNA molecule, may be injected and expressed in an oocyte. Techniques for cytoplasmic injections of RNA are well-established in the art. Nucleic acid injections may for instance be performed on denuded oocytes using, for example, a glass microelectrode and a commercially available injection system. Amounts of nucleic acid molecules injected into an oocyte can vary from about 0.01 to about 10 ng per oocyte, including e.g. from about 1 up to about 10 ng of nucleic acid. Nucleic acid molecules may be injected in volumes ranging from 10 to 100 nl of buffer, including e.g. about 50 nl of buffer.

As explained above, in some embodiments an electrophysiological response can be detected using voltage clamp techniques. Oocytes can be voltage clamped with, for example, a two-electrode clamp. A suitable physiological buffer is perfused across the oocytes and a baseline recording obtained. Following baseline recording, oocytes can be perfused with an appropriate recording solution (e.g., 2 mM $NaCl_2$, 1 mM $MgCl_2$, 96 mM KCl, 5 mM Na-HEPES, 1 mM $CaCl_2$)). Oocyte solutions can, for example, be diluted (e.g., in distilled $H_2O$) from stock solutions. Test compounds may for instance be used in the form of stocks solutions, typically preserving the ionic and osmotic conditions of the recording solution. A dilution may then be prepared in recording solutions to a desired final concentration. Oocytes are perfused with recording solution containing final.

Commercial amplifiers are available for recording transmembrane currents. Electrodes are generally filled with a suitable ionic solution, and responses may be recorded at room temperature while the oocyte membrane is voltage-clamped at the desired membrane potential (e.g., −80 mV). Other configurations and equipment that are known in the art can also be used.

In some embodiments an electrophysiological response can be detected using a technique called "patch clamping". A small patch of cell membrane is generally isolated on the tip of a micropipette by pressing the tip against the membrane. It has been suggested that if a tight seal between the micropipette and the patch of membrane is established electric current may pass through the micropipette only via ion channels in the patch of membrane. If this is achieved the activity of the ion channels and their effect on membrane potential, resistance and current may be monitored. If the electric potential across the membrane remains constant, the current supplied to it is equal to the current flowing through ion channels in the membrane. The closing of ion channels in the membrane causes resistance of the membrane to increase. If the current applied remains constant; the increase of resistance is in direct proportion to an increase of electric potential across the membrane.

A method for identifying compounds that modulate nicotinic AChR activity (e.g., agonists and antagonists) typically requires comparison to a control. One type of a "control" cell or "control" culture is a cell or culture that is treated substantially the same way as the cell or culture exposed to the test compound. The only difference to the test cell or culture is that the control cell/culture is not exposed to a test compound. For example, in a method that is based on a voltage clamp electrophysiological technique, the same cell can be tested in the presence and absence of test compound, by merely changing the external solution bathing the cell. Another type of "control" cell or "control" culture may be a cell or a culture of cells that are identical to the transfected cells, except that the cells employed for the control culture do not express functional nicotinic AChRs. In this situation, the response of test cell to test compound is compared to the response (or lack of response) of receptor-negative (control) cell to test compound, when cells or cultures of each type of cell are exposed to substantially the same reaction conditions in the presence of compound being analysed.

In some embodiments a measurement may be compared to a predetermined threshold value. A predetermined threshold value may in some embodiments be set on the basis of data collected from preceding measurements using compounds known to modulate, e.g. activate or inhibit nAChR activity. In some embodiments a certain percentile of such data may be used as a threshold value. The range of the values of a set of data obtained from cells can be divided into 100 equal parts, i.e. percentages of the range can be determined. A percentile represents the value within the respective range below which a certain percent of the data fall, in other words the percentage of the values that are smaller than that value. For example the 95th percentile is the value below which 95 percent of the data are found. In some embodiments nAChR activity may be regarded as decreased or low if it is below the $90^{th}$ percentile, or below the $80^{th}$ percentile. In some embodiments nAChR activity may be regarded as decreased or low if it is below the $70^{th}$ percentile.

In some embodiments a substrate for use in screening disclosed in European patent application EP 1 621 888 is used in connection with a biological membrane.

Treatment and Application of Compounds

A compound disclosed herein may be useful for reducing a tick population and may be useful in a method of inhibiting a tick population, which includes applying to a locus of the tick an effective tick-inactivating amount of a compound described in this specification. A respective compounds may be useful for reducing the number of ticks on a particular animal or in a particular area, and may be useful in a method of inhibiting a tick population.

Provided is also a method of reducing a population of *Rhipicephalus* ticks. The method includes applying to a locus of the tick an effective amount of a compound disclosed herein. Provided herein is furthermore a method of clearing a surface with a compound effective to control ticks. Provided is also a method of treating a subject with a compound effective to control ticks. The method includes applying an agent that modulates the activity of a nAchR of a *Rhipicephalus* tick to a surface or to a subject agent known or suspected to include a *Rhipicephalus* tick. The respective compound may in some embodiments be a compound of the following formula (I), or a pharmaceutically acceptable salt, hydrate or prodrug thereof:

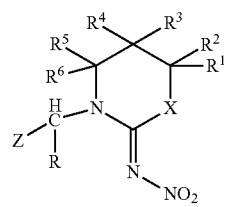

In this formula X may for example be a sulfur atom or an oxygen atom. In some embodiments X may be N—$R^7$ or (CH)—$R^8$. $R^7$ may be a hydrogen atom. In some embodiments $R^7$ may be a halogen atom. $R^7$ may also be a hydroxy group, an alkoxy group. In some embodiments $R^7$ may be a benzyloxy group. $R^7$ may also be an alkenyl group. $R^8$ may be a hydrogen atom or an alkyl group. In some embodiments $R^8$ may be an aryl group or a benzyl group.

R, $R^1$, $R^2$, $R^5$ and $R^6$ may be selected independently from one another. R, $R^1$, $R^2$, $R^5$ and $R^6$ may be a hydrogen atom or an alkyl group.

$R^3$ and $R^4$ may also be selected independently from one another. $R^3$ and $R^4$ may be a hydrogen atom or an alkyl group. $R^3$ and $R^4$ may also be a hydroxy group.

Z is a 5 or 6 membered heterocyclic group that includes at least one hetero atom. The hetero atom may for example be an oxygen atom or a sulphur atom. In some embodiments the hetero atom is a nitrogen atom. In some embodiments heterocyclic group Z is a 5 membered ring that contains two hetero atoms. In some embodiments heterocyclic group Z is a 6 membered ring that contains two hetero atoms.

Further explanations on these moieties can be found in U.S. Pat. No. 4,742,060, which is incorporated herein by reference for all purposes. In case of conflict, the present document, including definitions, will prevail.

The respective compound may in some embodiments be a compound of the following formula (II) or a pharmaceutically acceptable salt, hydrate or prodrug thereof:

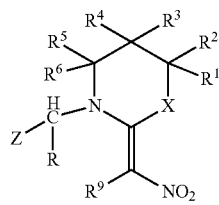

In this formula X, Z, R, and $R^1$ to $R^6$ are as defined above. $R^9$ may be a hydrogen atom or an alkyl group. $R^9$ may also be an alkenyl group or an alkynyl group. $R^9$ may in some embodiments be a halogen atom. In some embodiments $R^9$ may be a hydroxy group or an alkoxy group. In some embodiments $R^9$ may be a benzoyl group or a benzyloxy group. Further explanations and definitions can be found in U.S. Pat. No. 4,742,060 (supra).

The respective compound may in some embodiments be a compound of the following formula (III) or a pharmaceutically acceptable salt, hydrate or prodrug thereof:

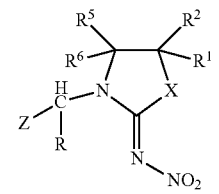

In this formula X, Z, R, $R^1$, $R^2$, $R^5$ and $R^6$ are as defined above.

The respective compound may in some embodiments be a compound of the following formula (IV) or a pharmaceutically acceptable salt, hydrate or prodrug thereof:

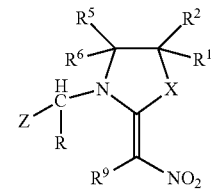

In this formula X, Z, R, $R^1$, $R^2$, $R^5$, $R^6$ and $R^9$ are as defined above.

A compound to be applied may also be an α-unsaturated amine as described in European patent application EP 0 302 389, incorporated herein by reference for all purposes. In case of conflict, the present document, including definitions, will prevail.

Further examples of respective α-unsaturated amines are the heterocyclic compounds described in international patent application WO 2010/099965, incorporated herein by reference for all purposes. In case of conflict, the present document, including definitions, will prevail.

A compound to be applied may also be a (tetrahydro-3-furanyl)methylamine compound as described in European patent application EP 0 649 845, incorporated herein by reference for all purposes. In case of conflict, the present document, including definitions, will prevail.

A compound to be applied may also be an imino- or alkenyl compound, or a pharmaceutically acceptable salt, hydrate or prodrug thereof, as described in European patent application EP 0 649 845, incorporated herein by reference for all purposes. In case of conflict, the present document, including definitions, will prevail.

A compound to be applied may also be a tetrahydro-2-(nitromethylene)-2H-1,3-thiazine, or a pharmaceutically acceptable salt, hydrate or prodrug thereof, as described in U.S. Pat. No. 3,993,648, incorporated herein by reference for all purposes. In case of conflict, the present document, including definitions, will prevail.

A compound to be applied may also be a compound of the following formula (V) or a pharmaceutically acceptable salt, hydrate or prodrug thereof:

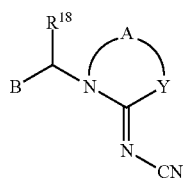

In this formula $R^{18}$ may be hydrogen or an alkyl group. In some embodiments $R^{18}$ may be a methyl group or an ethyl group. A is an ethylene group, which may be substituted by alkyl or a trimethylene group. Y may be an oxygen or sulfur atom. Y may also be a nitrogen atom carrying a hydrogen atom or an alkyl group. Y may also be a carbon atom carrying a hydrogen atom and a further group. This further group may be hydrogen or an alkyl group. B is a 5- or 6-membered heterocyclic group, which may optionally be substituted. The 5- or 6-membered heterocyclic group may be a 3- or 4-pyridyl group, which may optionally be substituted. The 5- or 6-membered heterocyclic group may also be a ring that contains two or more hetero atoms such as one or more nitrogen atoms. A respective hetero atom in the 5- or 6-membered heterocyclic group may also be an oxygen or a sulfur atom.

Further explanations on this compound and the respective moieties can be found in U.S. Pat. No. 4,849,432, which is incorporated herein by reference for all purposes. In case of conflict, the present document, including definitions, will prevail.

A compound to be applied may also be a guanidine compound, or a pharmaceutically acceptable salt, hydrate or prodrug thereof, as described in European patent application EP 0 376 279, incorporated herein by reference for all purposes. In case of conflict, the present document, including definitions, will prevail.

A compound to be applied may also be an oxadiazine compound, or a pharmaceutically acceptable salt, hydrate or prodrug thereof as described in U.S. Pat. No. 5,852,012, incorporated herein by reference for all purposes. In case of conflict, the present document, including definitions, will prevail.

In some embodiments a compound to be applied may be different from a compound disclosed in international patent applications WO 2006/061146 and WO 2006/061147. In some embodiments a compound to be applied may be a compound disclosed in international patent applications WO 2006/061146 and WO 2006/061147.

In some embodiments a compound to be applied may be different from a compound disclosed in international patent application WO 2008/003738. In some embodiments a compound to be applied may be a compound disclosed in international patent application WO 2008/003738.

In some embodiments a compound to be applied may be different from a compound disclosed in international patent application WO 2014/122083. In some embodiments a compound to be applied may be a compound disclosed in international patent application WO 2014/122083.

In some embodiments a compound to be applied may be different from a compound disclosed in international patent application WO 2005/036966. In some embodiments a compound to be applied may be a compound disclosed in international patent application WO 2005/036966.

In some embodiments a compound to be applied may be different from a compound disclosed in international patent application WO 2005/107468. In some embodiments a compound to be applied may be a compound disclosed in international patent application WO 2005/107468.

A compound effective to control ticks can be applied per se, or in a composition where it may be mixed with other active ingredients, or suitable carriers or excipient(s). Exemplary routes of uptake by an animal treated include, but are not limited to, oral, transdermal, and parenteral delivery.

The respective compound or a pharmaceutically acceptable salt, hydrate or prodrug thereof may in some embodiments be combined with a spinosyn compound, or a pharmaceutically acceptable salt, hydrate or prodrug thereof. A spinosyn compound generally consists of a 5,6,5-tricyclic ring system, fused to a 12-membered macrocyclic lactone, a neutral sugar moiety (2N,3N,4N-tri-O-methylrhamnose), and an amino sugar moiety (forosamine). A spinosyn compound is a macrolide that contains a tetracyclic ring system to which two different sugar moieties are attached. In one embodiment, the spinosyn is isolated from the pesticidal fraction from the soil bacteria *Saccharopolyspora spinosa*, coded A83543. Spinosyns are commercially available, for instance under the brand names Conserve™ SC, SpinTor™, Entrust™, Fire Ant Nightmare™ or Bulls-Eye™.

A spinosyn compound may for example be a compound of the following formula (VI):

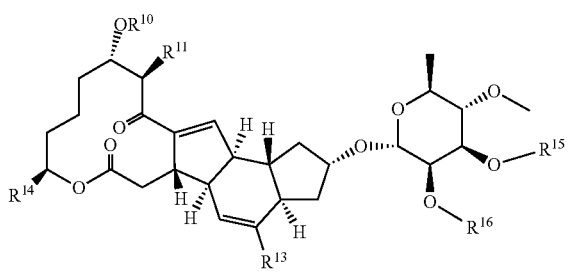

In this formula $R^{11}$, $R^{13}$, $R^{14}$, $R^{15}$ and $R^{16}$ may be selected independently from one another. $R^{11}$, $R^{13}$, $R^{15}$ and $R^{16}$ may be a hydrogen atom or an alkyl group. In some embodiments $R^{11}$, $R^3$, $R^{14}$, $R^{15}$ and $R^{16}$ may be a methyl group or an ethyl group.

$R^{10}$ may be H or one of the following groups:

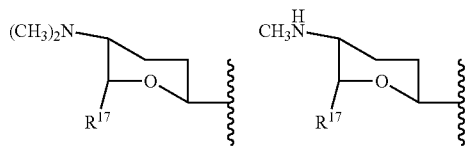

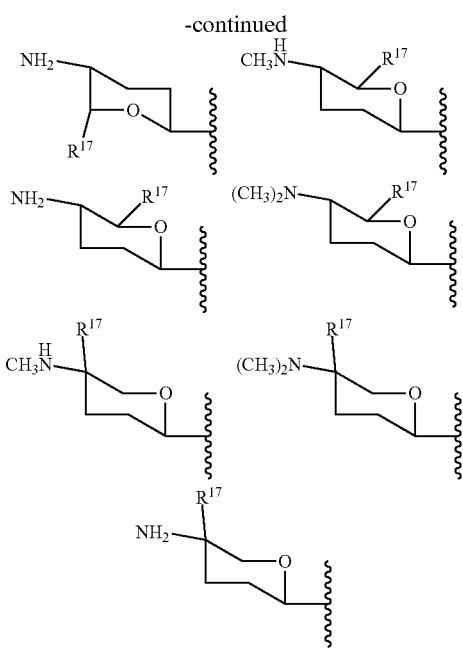

In this moiety $R^{17}$ may be an alkyl group. In some embodiments $R^{17}$ may be a methyl group or an ethyl group. In some embodiments $R^{17}$ may be an n-propyl group or an isopropyl group.

Further explanations on this compound and the respective moieties can be found in U.S. Pat. Nos. 5,571,901, 5,631, 155 and 5,202,242, which are incorporated herein by reference for all purposes. In case of conflict, the present document, including definitions, will prevail.

Illustrative examples of spinosyn compounds are spinetoram and spinosad. Spinetoram is a mixture consisting of the spinosyn derivatives 5,6-dihydro-3'-O-ethyl spinosyn J, and 3'—O— ethyl spinosyn L, i.e. (2R,3aR,5aR,5bS,9S, 13S,14R,16aS,16bR)-2-[(6-deoxy-3-O-ethyl-2,4-di-O-methyl-α-L-mannopyranosyl)oxy]-13-[[(2R,5R,6R)-5-(dimethylamino)tetrahydro-6-methyl-2H-pyran-2-yl]oxy]-9-ethyl-2,3,3a,4,5,5a,5b,6,9,10,11,12,13,14,16a,16b-hexadecahydro-14-methyl-1H-as-indaceno[3,2-d] oxacyclododecin-7,15-dione, mixture with (2S,3aR,5aS, 5bS,9S,13S,14R, 16aS,16bS)-2-[(6-deoxy-3-O-ethyl-2,4-di-O-methyl-α-L-mannopyranosyl)oxy]-13-[[(2R,5S, 6R)-5-(dimethylamino)tetrahydro-6-methyl-2H-pyran-2-yl] oxy]-9-ethyl-2,3,3a,5a,5b,6,9,10,11, 12,13,14,16a,16b-tetradecahydro-4,14-dimethyl-1H-αs-indaceno[3,2-d] oxacyclododecin-7,15-dione.

The present inventors have found that a spinosyn compound can act as an agonist on *R. microplus* nAChRα5, and act as an allosteric modulator on *R. microplus* nAChRα6. On *R. microplus* nAChRα5, no desensitization of responses by a spinosyn compound were found, similar to responses to ACh. Without being bound by theory, it can be concluded that at least with regard to nAChRα6, a spinosyn compound and a neonicotinoid compound do not act on identical sites of a receptor. It may thus be advantageous to combine a neonicotinoid compound with a spinosyn compound, as it may be assumed that ticks are less likely to develop a resistance against a combination of such compounds. The same may apply to a combination of a spinosyn compound and any other compound that may be identified using a method described herein.

A composition containing a compound effective to control ticks may in some embodiments be a concentrated formulation that is dispersed in water for application, or a dust or granular formulation which is applied without further treatment. A respective composition may be prepared according to procedures and formulae which are known in the veterinary and/or agricultural chemical art.

Suitable routes of administering to a subject a compound effective to control ticks may, for example, include depot, oral, rectal, transmucosal, or intestinal administration; parenteral delivery, including intramuscular, subcutaneous, or intravenous injections. Alternately, one may administer the compound in a local rather than systemic manner, for example, via application of the compound directly onto the coat or skin.

The listing or discussion of a previously published document in this specification should not necessarily be taken as an acknowledgement that the document is part of the state of the art or is common general knowledge.

While embodiments of the invention have been illustratively described, it is to be understood that the invention is not limited thereto but may be otherwise variously embodied and practiced within the scope of the appending claims. The invention may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

In order that the invention may be readily understood and put into practical effect, particular embodiments will now be described by way of the following non-limiting examples.

EXAMPLES

The examples illustrate techniques that can be used in a methods disclosed herein as well as exemplary embodiments of isolating and expressing a nucleic acid molecule and a polypeptide described above.

Materials

The ticks used in this study were reared at Bayer Animal Health (Monheim, Germany), life stages collected separately, snap-freezed in liquid nitrogen and shipped on dry ice. At arrival the samples were stored at −80° until needed.

Transcriptome Sequencing and Analysis

High quality total RNA extracted from a pool of larvae, nymphs and adults R. microplus was sent to Eurofins Genomics (Germany) for cDNA library preparation and normalisation. The cDNA was sequenced using Illumina HiSeq2002 technology, using two full lanes with 1×100 bp paired ends protocol.

Following the transcriptome analysis, a full sequence of a putative nAChRα5 (Rma5) subunit and a partial putative nAChRα6 (Rma6) subunit were identified. The partial Rma6 sequence was extended using 3' RACE amplification. Oligonucleotide primers were designed to amplify the coding region of the gene, which was then cloned into pCR4-TOPO vector and verified by sequencing.

Molecular Cloning of Rma5 and Rma6

Total RNA was extracted from a pool of cattle tick larvae, nymphs and adults using Trizol (Life Technologies) following manufacturer's protocol. RACE-cDNA was synthesized from total RNA using the FirstChoice RLM-RACE kit (Ambion) and Maxima H-reverse transcription kit (Thermo). Nicotinic AChRα6 sequence extracted from the transcriptome database lacked part of the 3' end therefore 3' RACE amplification was initially done to obtain the missing sequence. Full-length Rma5 and Rma6 sequences were amplified using KAPA HiFi polymerase (KAPA Biosystems) and the transcripts ligated into pCR4-TOPO TA vector (Life Technologies). One Shot Top10 competent E. coli cells (Life technologies) were transformed using the ligated products and grown on ampicillin-containing LB-agar plates at 37° C. overnight. Colonies of both Rmα5 and Rmα6 were grown in LB-broth, the plasmid DNA isolated using PureLink™ Quick plasmid miniprep kit following manufacturer's protocol and the DNA sequenced using the vector specific primers M13 Rev and M13 Uni (Eurofins Genomics).

The phylogenetic analysis of the sequences revealed that the Rmα5 sequence clusters with other insect (non-dipteran) alpha 5 subunits and has over 70% identity with Ixodes scapularis nAChRα5, cf. FIG. 1. The Rma6 sequence has around 60% identity with other insect alpha 6 subunits and 86% identity with I. scapularis nAChRα6.

Furthermore, following cloning and sequencing of a number of RNA samples from R. microplus, two alternative spliced variants have been identified for exon 3 of nAChR alpha6.

Results of Rmα5 and Rmα6 Isolation and Cloning

The cattle tick transcriptome has been sequenced in order to determine the sequence of a number of neuronal ion channels including nAChRs. In this study, the assembly has yielded a number of 250000 contigs of 950 bp average length. The BLAST search of the generated database using insect nAChR sequences (Anopheles gambiae nAChRα1, Anopheles gambiae nAChRα2, Bombyx mori nAChRα5) has pulled a number of contigs coding nAChRs which included a full-length alpha5-like and a partial alpha6-like sequence. Following RACE amplification of the 3' end of the alpha6-like sequence and the assembly of a full length contig, both alpha5-like and alpha6-like transcripts were amplified and cloned into pCR4-TOPO. The translation of the nucleotide sequence revealed a an open reading frame of 552 amino acids and 501 amino acids for alpha5-like and alpha6-like, respectively.

Heterologous Expression and Electrophysiological Recording in Xenopus Oocytes

The plasmids containing the sequences of choice were linearized using BeuI (SpeI) FastDigest (ThermoFisher) restriction enzyme for 30 min at 37°, and an aliquot run on an agarose gel to check for complete linearization. The plasmid DNA was phenol:chloroform purified and ethanol precipitated. The pellet was re-suspended in deionized water. Capped RNA was synthesized using mMessage mMachine T7 kit from 1 µg linearized plasmid DNA, the sample phenol:chloroform purified and isopropanol precipitated. The pellet was re-suspended in deionized water to a concentration of 500 ng/µl, analysed on an agarose gel for integrity and stored at −80° C. until further use.

Xenopus laevis oocytes were purchased as whole ovaries from the European Xenopus Resource Centre (University of Portsmouth), delivered in less than 24 h in Modified Barth's Saline (MBS) on wet ice. Upon arrival, the oocytes were treated with 2 mg/ml collagenase type I (Sigma-Aldrich) in calcium-free Barth's solution (NaCl 88 mM, Tris-HCl 15 mM, $NaHCO_3$ 2.4 mM, $MgCl_2$ 0.82 mM, KCl 1 mM, pH 7.5) for 30 min at room temperature. The separated oocytes were rinsed thoroughly in calcium-free Barth's solution, manually de-folliculated and injected using a Drummond microinjector with 25 ng/oocyte capped RNA. The oocytes were incubated at 18° C. in calcium-containing (77 mM) Barth's solution supplemented with 4 µg/ml Kanamycin, 50 µg/ml Tetracycline, 100 U/ml Penicillin and 100 µg/ml Streptomycin. Two-electrode voltage clamp recordings were performed after 3-5 days using an OC-725C oocyte clamp (Warner instruments) with the membrane potential clamped at −60 mV. The oocytes were continuously perfused with frog Ringer's solution (NaCl 115 mM, KCl 2.5 mM, $CaCl_2$) 1.8 mM and HEPES 10 mM) and the dilutions of ligands prepared in Ringer's saline applied using a VC-8 multi-valve perfusion system (Warner Instruments). Following ligand application, the current required to maintain the membrane potential at −60 mV was measured and used for subsequent data analysis.

Bioinformatics and Data Processing

The transcriptome sequencing data was trimmed to remove primers using FastQC, digitally normalised to reduce the abundance of the more common transcripts and assembled using Trinity software. The contigs were loaded onto a local DeCypher server (Active Motif, CA, USA) and searched using Terra-BLAST algorithm with sequence specific probes.

The sequences alignment, nucleotide primers design and the phylogenetic relationship of nAChR subunits were done using Genious® (Biomatters Ltd.).

Two-electrode voltage clamp electrophysiology data acquisition was done using LabScribe software (iWorks Systems) and the data transferred to GraphPad Prism (GraphPad Software) for traces analysis and dose-response curve fitting.

Characterisation of Rmα5 homopentamers

Figure 11:
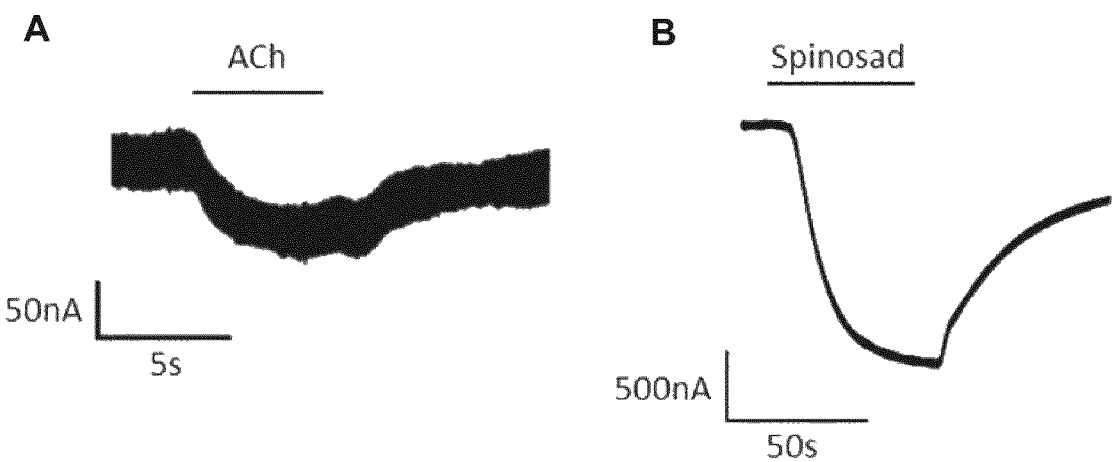
FIG. 11B depicts a representative trace showing a response of an *R. microplus* Rma5 to spinosad (30 μM) application.

Representative responses to acetylcholine (ACh) and spinosad are presented in FIGS. 11A and B. The responses to ACh are relatively small and are non-desensitizing while the responses to spinosad application are large and also non-desensitizing. Spinosad activates the receptor slowly, the first signs of depolarization showing after about 15 s of perfusion and the response plateaus after around 30 s application. The dose-response curves for ACh and spinosad are presented in FIG. 10. Spinosad activates the Rmα5 receptor with higher efficacy than ACh, the $EC_{50}$ of the spinosad ($9.39\pm0.87$ µM) being over 10 times lower than ACh $EC_{50}$ ($108\pm27$ µM).

Characterisation of Rmα6 Homopentamers

Rma6 homopentamers expressed in *Xenopus* oocytes are responding with big, fast desensitizing inward currents to ACh exposure. The $EC_{50}$ calculated from a dose-response curve is $1.97\pm1.2$ µM (FIG. 5). Spinosad does not directly activate the Rma6 receptor but seems to act like an allosteric modulator, affecting the desensitization rate of the receptor. As seen in FIGS. 14A and B, after 15 s pre-application of spinosad followed by a 3 s co-application of ACh, the desensitization rate of subsequent ACh responses is affected in a dose-response manner by spinosad (provisional $EC_{50}=5.1$ µM).

Figure 12A:
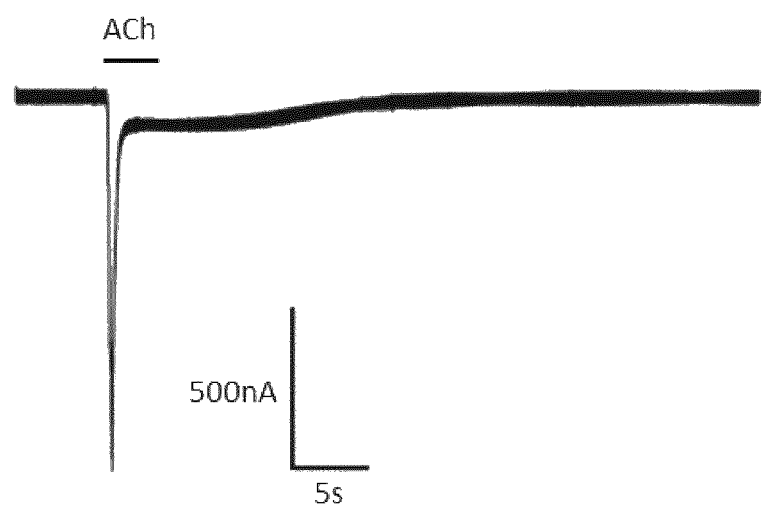
FIG. 12A shows a representative response of Rma6 to ACh (10 μM) prior to pre-application of 30 μM spinosad.
Figure 12B:
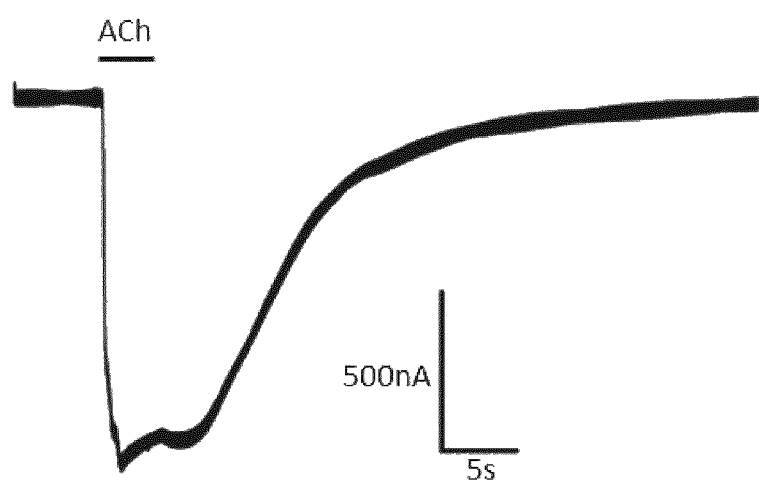
FIG. 12B shows a representative response of Rma6 to ACh (10 μM) after pre-application of 30 μM spinosad.
Figure 13:
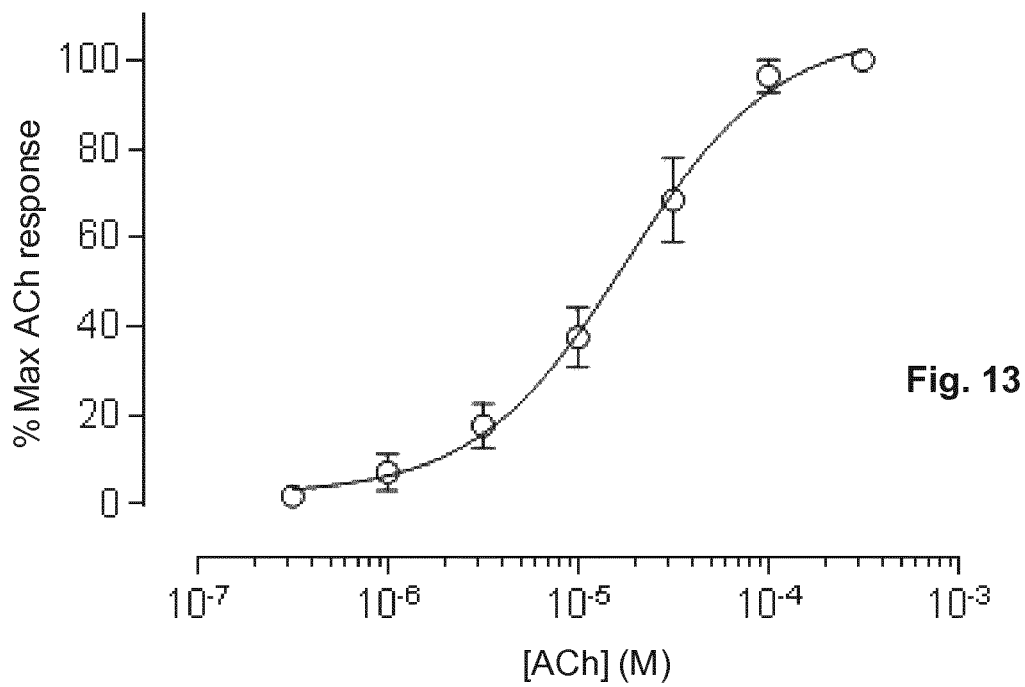
FIG. 13 depicts a dose response curve of Acetylcholine on *Xenopus* oocytes expressing Rma6 homopentamers (subunits of SEQ ID NO: 4).

Imidacloprid, is a partial agonist on Rmα6 homopentamers, producing small, non-desensitizing responses following a 5 s application (FIGS. 12A and B).

CONCLUSION

In summary, the nAChRα5 (Rma5) and nAChRα6 (Rma6) subunits isolated from the cattle tick *Rhipicephalus microplus* are forming functional homopentamers when injected into *Xenopus* oocytes. ACh activates both receptors with high efficacy for Rma6 ($EC_{50}=1.97\pm0.2$ µM) and a much lower one for Rmα5 ($EC_{50}=108\pm27$ µM). Spinosad acts as an agonist on the Rma5 receptors ($EC_{50}=9.39\pm0.87$ µM) and as a type II allosteric modulator on Rma6 receptors (provisional $EC_{50}=5.1$ µM). Imidacloprid is a partial agonist on Rma6 receptors, producing non-desensitizing responses.

What is claimed is:

1. A vector or chimeric expression cassette comprising a recombinant nucleic acid molecule encoding a polypeptide, wherein the polypeptide comprises the amino acid sequence of SEQ ID NO: 10 or SEQ ID NO: 2.

2. The vector or chimeric expression cassette of claim 1, wherein the recombinant nucleic acid molecule comprises the nucleotide sequence of SEQ ID NO: 1 or SEQ ID NO: 9.

3. The vector or chimeric expression cassette of claim 1, wherein the recombinant nucleic acid molecule further comprises one or more regulatory regions operatively linked to the nucleic acid sequence encoding said amino acid sequence.

* * * * *

```
                        SEQUENCE LISTING

<160> NUMBER OF SEQ ID NOS: 21

<210> SEQ ID NO 1
<211> LENGTH: 1770
<212> TYPE: DNA
<213> ORGANISM: artificial sequence
<220> FEATURE:
<223> OTHER INFORMATION: cDNA based on Rhipicephalus microplus

<400> SEQUENCE: 1
acctccacca tgtttcttcg gggactgatt ccagccatcg tgtacgtgtg cctgtggacg      60
gcctgcctcc tctccacaaa cctcgtggcc gaggtggacg agacgtggtc ggctcgcgag     120
aacgactcct cgtcgccgcc gccgccgcca ctgagtcacg agaagcggct gatggactcg     180
ctgctgcgcc actacgacgc cagcgtgagg cccgtcaaga actcctcgga gcccgtcatc     240
attcggctgg gcatcacgct cacgcagata ttcgacctgg acgagaagaa tcaagtccta     300
acaaccatcg tttggcttga ccaggaatgg ttcgacgagt acctcacttg ggacccgttg     360
gagtttggaa acttcagcaa cctcaggctg ccctgccaca agatttggct gcctgacatc     420
gttctctaca caacgcgga cgactacacg cggggctact tccagacgcg cgccatgatc     480 gaccccagg gccgagtgtt ctggccgcca cccaccaagt ttcgcagcac ctgcccggtg     540
gacgtaacgt acttcccttt cgacgaccag gtctgcacaa tgaagttcgg ttcttggatc     600
tatgacgggc tacaagtgga catccagaac cggacatccg aggttgacct ggtcaattac     660
atgcccaacg gcgagtggga gctgcttgag gcacgcatgg tgcgcaacgt ggtctactac     720
ccttgctgtc cagaccagcc gttcccggac atcaccgtgg tcttggtcat gaggcgcaag     780
acgctctact acatgtacaa cgtggtcctg ccctgcatca tgatgtctgt gctgactctg     840
ctcgtcttct gcctaccgcc ggactcgggc gagaagatcg cgctcggcgt cacagtgctg     900
ctagcattct ccgtgttcat gctggccata gcggagaaga tgcccgagac atcggagtcc     960 ataccttac tgggaatata cctgacggcc gtgatggcca tcacgtccat ctcggtcgtc    1020
atgaccgtga tcgtcctcaa cttccactac cgcggcccca gccggaaaga agtgccagcg    1080
tggctccgcc gtctcctgct caacaagtca tcctccagtc gtggttggtt ctcgaagccg    1140
gcgcgccgca gacgtcgg cgacaatcac gtgcacttct acgacttgcc atcgcgcaca    1200
gcagcctcca aggaccgctc agacctggac gacgacgtag acggcagcag aagacctgcg    1260
```

-continued

```
gccgacgaca ccttccggct cgtcgtggac agcgtcgtga tcggcagcga agaccgctac    1320
actcgcggcg agtacgccga gcactccgcg agcaacgagt ccccgagtcc cgtcctccac    1380
ggcgacatgt cgcggaacaa tgcctccggg tcggccaggc accgccgctg tcgcgctggt    1440
gccgctagtg gcggatccac taagcgcgtg caggaagaag tgctgcggac tttgcggtac    1500
ctgatggaga aacagcagcg cgaggagcac ctcaccccga ctgtgaacga gtggagacag    1560
atggctctcg tgatagatcg caccttgttc tggttctttc tgatcatcac agccgtgtca    1620
tccrtctgct tcctagtcgt catacccata cagaggcggg gactgtgact gtgacttggg    1680
cggagttgtg agcaactctg cattgccatg acgtgctaaa acacttaaag agagaggcag    1740
acgggagaga tccgagggat tcatgtgtca                                    1770
```

<210> SEQ ID NO 2
<211> LENGTH: 552
<212> TYPE: PRT
<213> ORGANISM: Rhipicephalus microplus

<400> SEQUENCE: 2

```
Met Phe Leu Arg Gly Leu Ile Pro Ala Ile Val Tyr Val Cys Leu Trp
1               5                   10                  15

Thr Ala Cys Leu Leu Ser Thr Asn Leu Val Ala Glu Val Asp Glu Thr
                20                  25                  30

Trp Ser Ala Arg Glu Asn Asp Ser Ser Pro Pro Pro Pro Pro Pro Leu
            35                  40                  45

Ser His Glu Lys Arg Leu Met Asp Ser Leu Leu Arg His Tyr Asp Ala
        50                  55                  60

Ser Val Arg Pro Val Lys Asn Ser Ser Glu Pro Val Ile Ile Arg Leu
65                  70                  75                  80

Gly Ile Thr Leu Thr Gln Ile Phe Asp Leu Asp Glu Lys Asn Gln Val
                85                  90                  95

Leu Thr Thr Ile Val Trp Leu Asp Gln Glu Trp Phe Asp Glu Tyr Leu
            100                 105                 110

Thr Trp Asp Pro Leu Glu Phe Gly Asn Phe Ser Asn Leu Arg Leu Pro
        115                 120                 125

Cys His Lys Ile Trp Leu Pro Asp Ile Val Leu Tyr Asn Asn Ala Asp
    130                 135                 140

Asp Tyr Thr Arg Gly Tyr Phe Gln Thr Arg Ala Met Ile Asp Pro Gln
145                 150                 155                 160

Gly Arg Val Phe Trp Pro Pro Thr Lys Phe Arg Ser Thr Cys Pro
                165                 170                 175

Val Asp Val Thr Tyr Phe Pro Phe Asp Asp Gln Val Cys Thr Met Lys
            180                 185                 190

Phe Gly Ser Trp Ile Tyr Asp Gly Leu Gln Val Asp Ile Gln Asn Arg
        195                 200                 205

Thr Ser Glu Val Asp Leu Val Asn Tyr Met Pro Asn Gly Glu Trp Glu
    210                 215                 220

Leu Leu Glu Ala Arg Met Val Arg Asn Val Val Tyr Tyr Pro Cys Cys
225                 230                 235                 240

Pro Asp Gln Pro Phe Pro Asp Ile Thr Val Leu Val Met Arg Arg
                245                 250                 255

Lys Thr Leu Tyr Tyr Met Tyr Asn Val Val Leu Pro Cys Ile Met Met
            260                 265                 270

Ser Val Leu Thr Leu Leu Val Phe Cys Leu Pro Pro Asp Ser Gly Glu
```

```
              275                 280                 285
Lys Ile Ala Leu Gly Val Thr Val Leu Leu Ala Phe Ser Val Phe Met
        290                 295                 300
Leu Ala Ile Ala Glu Lys Met Pro Glu Thr Ser Glu Ser Ile Pro Leu
305                 310                 315                 320
Leu Gly Ile Tyr Leu Thr Ala Val Met Ala Ile Thr Ser Ile Ser Val
                325                 330                 335
Val Met Thr Val Ile Val Leu Asn Phe His Tyr Arg Gly Pro Ser Arg
            340                 345                 350
Lys Glu Val Pro Ala Trp Leu Arg Arg Leu Leu Leu Asn Lys Ser Ser
        355                 360                 365
Ser Ser Arg Gly Trp Phe Ser Lys Pro Ala Arg Arg Lys Thr Val Gly
    370                 375                 380
Asp Asn His Val His Phe Tyr Asp Leu Pro Ser Arg Thr Ala Ala Ser
385                 390                 395                 400
Lys Asp Arg Ser Asp Leu Asp Asp Asp Val Asp Gly Ser Arg Arg Pro
                405                 410                 415
Ala Ala Asp Asp Thr Phe Arg Leu Val Val Asp Ser Val Val Ile Gly
            420                 425                 430
Ser Glu Asp Arg Tyr Thr Arg Gly Glu Tyr Ala Glu His Ser Ala Ser
        435                 440                 445
Asn Glu Ser Pro Ser Pro Val Leu His Gly Asp Met Ser Arg Asn Asn
    450                 455                 460
Ala Ser Gly Ser Ala Arg His Arg Arg Cys Arg Ala Gly Ala Ala Ser
465                 470                 475                 480
Gly Gly Ser Thr Lys Arg Val Gln Glu Glu Val Leu Arg Thr Leu Arg
                485                 490                 495
Tyr Leu Met Glu Lys Gln Gln Arg Glu Glu His Leu Thr Arg Thr Val
            500                 505                 510
Asn Glu Trp Arg Gln Met Ala Leu Val Ile Asp Arg Thr Leu Phe Trp
        515                 520                 525
Phe Phe Leu Ile Ile Thr Ala Val Ser Ser Val Cys Phe Leu Val Val
    530                 535                 540
Ile Pro Ile Gln Arg Arg Gly Leu
545                 550

<210> SEQ ID NO 3
<211> LENGTH: 1535
<212> TYPE: DNA
<213> ORGANISM: artificial sequence
<220> FEATURE:
<223> OTHER INFORMATION: cDNA based on Rhipicephalus microplus

<400> SEQUENCE: 3
accacgacgc ggaccatgcg ccccggacgc ctgtctgtgc cgctgcagct aggcttctgc      60
gccaacctgc tgtggatcgc cgtgctgctc accgcgcctc aggactctga acaaggcgcg     120
cacgagcggc ggcttctggc agacctgctg gccaactaca cacccctgga gcggcccgtg     180
ctcaacgagt cggagccgct catcctcagc ttcgggctca cactgcagca gatcatagac     240
gtcgacgaaa agaatcagct aattattaca aatatctggt taacattgga ttggatagat     300
gtgaatctac gttggaaccc aaaagactac ggcggagtgc aggacctgcg tattccgcca     360
aacaaaattt ggaagcctga cgtgctcatg tacaacagcg cggacgaaaa gttcgacggc     420
acgtacccga ccaacgtggt cgtgcggagc aacggcagtt gcaactacat ccctcctggc     480
```

-continued

```
atctttaaga gcacgtgcaa gatcgacatt acgtggttcc cttttgacga tcagaagtgc    540
gacctgaagt tcggctcctg gacctatcac ggttatcagc tggaccttcg tgtcaacagt    600
gaggaaggcg gggatctgac tacctacatt cccaatggcg agtgggacct gataggcgtg    660
ccggagtgc gcaacgttcg cgagtatgcc tgctgtccgg agccgtacat cgacatcacg     720
tacaccatcc acatccggcg gcgcacgctc tactacggct caacctcat cattccctgc     780
gtgctcatct cgtccatgac tctgctcggt ttcacgctgc ccccgacac cggagagagg     840
ctcaccctgg gtgtaaccat tttgctgtcc ctgacggtat tcatgctcca gctcgccgag    900
accatgcctc cgacgtccga tgctgtctcc ataataggaa cttattttgc ctgcatcatg    960
atcatggttg ccttttcggt ggtcatgacc gtggtggtcc tgaactatca tcacagaaat   1020
caagagacga ccgaaatgcc tgctttgatt cgcacggtgt tcctggtgtg gctcccgtgg   1080
cttctgcgca tggagcctcc gggccagaag gcgaacaggc gcagcctctt cctcaacagc   1140
aagatgaaag agctcgagct gaaggagcgc tcatcgcgga gtctgctggc caacgtgctg   1200
gacatcgacg acgacttccg cacggccaac agcgccgccg ccgccgccga ctgccacggg   1260
tctcggaccc cgttcctggg cggtggcggc ggggcgtcca cggtgcacgc ttgcgtccac   1320
tcgtcgcgtg aactgaactt gatcttgcgc gagctgcgct tcatcacgag ccgcatgcgc   1380
aaggacgagc aagagcggga ggtcgttggc gagtggaagt tcgcggccat ggtcgtcgac   1440
cgctgctgcc tcatcatctt ctccctgttc accatcatct ccacctgcgc ctgcctcttc   1500
tcggcgcccc atctggtcgc ctagcgcacc ctgct                              1535
```

<210> SEQ ID NO 4
<211> LENGTH: 502
<212> TYPE: PRT
<213> ORGANISM: Rhipicephalus microplus

<400> SEQUENCE: 4

```
Met

Val Asn Ser Glu Glu Gly Gly Asp Leu Thr Thr Tyr Ile Pro Asn Gly
            195                 200                 205

Glu Trp Asp Leu Ile Gly Val Pro Gly Val Arg Asn Val Arg Glu Tyr
210                 215                 220

Ala Cys Cys Pro Glu Pro Tyr Ile Asp Ile Thr Tyr Thr Ile His Ile
225                 230                 235                 240

Arg Arg Arg Thr Leu Tyr Tyr Gly Phe Asn Leu Ile Ile Pro Cys Val
            245                 250                 255

Leu Ile Ser Ser Met Thr Leu Leu Gly Phe Thr Leu Pro Pro Asp Thr
            260                 265                 270

Gly Glu Arg Leu Thr Leu Gly Val Thr Ile Leu Leu Ser Leu Thr Val
            275                 280                 285

Phe Met Leu Gln Leu Ala Glu Thr Met Pro Pro Thr Ser Asp Ala Val
290                 295                 300

Ser Ile Ile Gly Thr Tyr Phe Ala Cys Ile Met Ile Met Val Ala Phe
305                 310                 315                 320

Ser Val Val Met Thr Val Val Leu Asn Tyr His His Arg Asn Gln
            325                 330                 335

Glu Thr Thr Glu Met Pro Ala Leu Ile Arg Thr Val Phe Leu Val Trp
            340                 345                 350

Leu Pro Trp Leu Leu Arg Met Glu Pro Pro Gly Gln Lys Ala Asn Arg
            355                 360                 365

Arg Ser Leu Phe Leu Asn Ser Lys Met Lys Glu Leu Glu Leu Lys Glu
            370                 375                 380

Arg Ser Ser Arg Ser Leu Leu Ala Asn Val Leu Asp Ile Asp Asp Asp
385                 390                 395                 400

Phe Arg Thr Ala Asn Ser Ala Ala Ala Ala Asp Cys His Gly Ser
            405                 410                 415

Arg Thr Pro Phe Leu Gly Gly Gly Gly Ala Ser Thr Val His Ala
            420                 425                 430

Cys Val His Ser Ser Arg Glu Leu Asn Leu Ile Leu Arg Glu Leu Arg
            435                 440                 445

Phe Ile Thr Ser Arg Met Arg Lys Asp Glu Gln Glu Arg Glu Val Val
            450                 455                 460

Gly Glu Trp Lys Phe Ala Ala Met Val Val Asp Arg Cys Cys Leu Ile
465                 470                 475                 480

Ile Phe Ser Leu Phe Thr Ile Ile Ser Thr Cys Ala Cys Leu Phe Ser
            485                 490                 495

Ala Pro His Leu Val Ala
            500

<210> SEQ ID NO 5
<211> LENGTH: 1535
<212> TYPE: DNA
<213> ORGANISM: artificial sequence
<220> FEATURE:
<223> OTHER INFORMATION: cDNA based on Rhipicephalus microplus

<400> SEQUENCE: 5
accacgacgc ggaccatgcg ccccggacgc ctgtctgtgc cgctgcagct aggcttctgc      60
gccaacctgc tgtggatcgc cgtgctgctc accgcgcctc aggactctga acaaggcgcg     120
cacgagcggc ggcttctggc agacctgctg gccaactaca caccctgga gcggcccgtg     180 ctcaacgagt cggagccgct catcctcagc ttcgggctca cactgcagca gatcatagac     240

```
gtcgacgaaa agaatcaaat aataacaaca aacgtgtggt taaatctgga ttggatagat    300
gtgaatctac gttggaaccc aaaagactac ggcggagtgc aggacctgcg tattccgcca    360
aacaaaattt ggaagcctga cgtgctcatg tacaacagcg cggacgaaaa gttcgacggc    420
acgtacccga ccaacgtggt cgtgcggagc aacggcagtt gcaactacat ccctcctggc    480
atctttaaga gcacgtgcaa gatcgacatt acgtggttcc cttttgacga tcagaagtgc    540
gacctgaagt tcggctcctg gacctatcac ggttatcagc tggaccttcg tgtcaacagt    600
gaggaaggcg gggatctgac tacctacatt cccaatggcg agtgggacct gataggcgtg    660
ccgggagtgc gcaacgttcg cgagtatgcc tgctgtccgg agccgtacat cgacatcacg    720
tacaccatcc acatccggcg gcgcacgctc tactacggct tcaacctcat cattccctgc    780
gtgctcatct cgtccatgac tctgctcggt ttcacgctgc cccccgacac cggagagagg    840
ctcaccctgg gtgtaaccat tttgctgtcc ctgacggtat tcatgctcca gctcgccgag    900
accatgcctc cgacgtccga tgctgtctcc ataataggaa cttattttgc ctgcatcatg    960
atcatggttg cctttttcggt ggtcatgacc gtggtggtcc tgaactatca tcacagaaat   1020
caagagacga ccgaaatgcc tgctttgatt cgcacggtgt tcctggtgtg gctcccgtgg   1080
cttctgcgca tggagcctcc gggccagaag gcgaacaggc gcagcctctt cctcaacagc   1140
aagatgaaag agctcgagct gaaggagcgc tcatcgcgga gtctgctggc caacgtgctg   1200
gacatcgacg acgacttccg cacggccaac agcgccgccg ccgccgccga ctgccacggg   1260
tctcggaccc cgttcctggg cggtggcggc ggggcgtcca cggtgcacgc ttgcgtccac   1320
tcgtcgcgtg aactgaactt gatcttgcgc gagctgcgct tcatcacgag ccgcatgcgc   1380
aaggacgagc aagagcggga ggtcgttggc gagtggaagt cgcggccat ggtcgtcgac    1440 cgctgctgcc tcatcatctt ctccctgttc accatcatct ccacctgcgc ctgcctcttc   1500
tcggcgcccc atctggtcgc ctagcgcacc ctgct                              1535
```

<210> SEQ ID NO 6  
<211> LENGTH: 502  
<212> TYPE: PRT  
<213> ORGANISM: Rhipicephalus microplus

<400> SEQUENCE: 6

```
Met Arg Pro Gly Arg Leu Ser Val Pro Leu Gln Leu Gly Phe Cys Ala
1               5                   10                  15

Asn Leu Leu Trp Ile Ala Val Leu Leu Thr Ala Pro Gln Asp Ser Glu
            20                  25                  30

Gln Gly Ala His Glu Arg Arg Leu Leu Ala Asp Leu Leu Ala Asn Tyr
        35                  40                  45

Asn Thr Leu Glu Arg Pro Val Leu Asn Glu Ser Glu Pro Leu Ile Leu
    50                  55                  60

Ser Phe Gly Leu Thr Leu Gln Gln Ile Ile Asp Val Asp Glu Lys Asn
65                  70                  75                  80

Gln Ile Ile Thr Thr Asn Val Trp Leu Asn Leu Asp Trp Ile Asp Val
                85                  90                  95

Asn Leu Arg Trp Asn Pro Lys Asp Tyr Gly Gly Val Gln Asp Leu Arg
            100                 105                 110

Ile Pro Pro Asn Lys Ile Trp Lys Pro Asp Val Leu Met Tyr Asn Ser
        115                 120                 125

Ala Asp Glu Lys Phe Asp Gly Thr Tyr Pro Thr Asn Val Val Val Arg
    130                 135                 140
```

Ser Asn Gly Ser Cys Asn Tyr Ile Pro Pro Gly Ile Phe Lys Ser Thr
145                 150                 155                 160

Cys Lys Ile Asp Ile Thr Trp Phe Pro Phe Asp Asp Gln Lys Cys Asp
                165                 170                 175

Leu Lys Phe Gly Ser Trp Thr Tyr His Gly Tyr Gln Leu Asp Leu Arg
            180                 185                 190

Val Asn Ser Glu Glu Gly Gly Asp Leu Thr Thr Tyr Ile Pro Asn Gly
        195                 200                 205

Glu Trp Asp Leu Ile Gly Val Pro Gly Val Arg Asn Val Arg Glu Tyr
    210                 215                 220

Ala Cys Cys Pro Glu Pro Tyr Ile Asp Ile Thr Tyr Thr Ile His Ile
225                 230                 235                 240

Arg Arg Arg Thr Leu Tyr Tyr Gly Phe Asn Leu Ile Ile Pro Cys Val
                245                 250                 255

Leu Ile Ser Ser Met Thr Leu Leu Gly Phe Thr Leu Pro Pro Asp Thr
            260                 265                 270

Gly Glu Arg Leu Thr Leu Gly Val Thr Ile Leu Leu Ser Leu Thr Val
        275                 280                 285

Phe Met Leu Gln Leu Ala Glu Thr Met Pro Pro Thr Ser Asp Ala Val
    290                 295                 300

Ser Ile Ile Gly Thr Tyr Phe Ala Cys Ile Met Ile Met Val Ala Phe
305                 310                 315                 320

Ser Val Val Met Thr Val Val Leu Asn Tyr His His Arg Asn Gln
                325                 330                 335

Glu Thr Thr Glu Met Pro Ala Leu Ile Arg Thr Val Phe Leu Val Trp
            340                 345                 350

Leu Pro Trp Leu Leu Arg Met Glu Pro Pro Gly Gln Lys Ala Asn Arg
        355                 360                 365

Arg Ser Leu Phe Leu Asn Ser Lys Met Lys Glu Leu Glu Leu Lys Glu
    370                 375                 380

Arg Ser Ser Arg Ser Leu Leu Ala Asn Val Leu Asp Ile Asp Asp Asp
385                 390                 395                 400

Phe Arg Thr Ala Asn Ser Ala Ala Ala Ala Asp Cys His Gly Ser
                405                 410                 415

Arg Thr Pro Phe Leu Gly Gly Gly Gly Ala Ser Thr Val His Ala
            420                 425                 430

Cys Val His Ser Ser Arg Glu Leu Asn Leu Ile Leu Arg Glu Leu Arg
        435                 440                 445

Phe Ile Thr Ser Arg Met Arg Lys Asp Glu Gln Glu Arg Glu Val Val
    450                 455                 460

Gly Glu Trp Lys Phe Ala Ala Met Val Val Asp Arg Cys Cys Leu Ile
465                 470                 475                 480

Ile Phe Ser Leu Phe Thr Ile Ile Ser Thr Cys Ala Cys Leu Phe Ser
                485                 490                 495

Ala Pro His Leu Val Ala
            500

<210> SEQ ID NO 7
<211> LENGTH: 1653
<212> TYPE: DNA
<213> ORGANISM: artificial sequence
<220> FEATURE:
<223> OTHER INFORMATION: portion of cDNA based on Rhipicephalus
      microplus

<400> SEQUENCE: 7

```
tttcttcggg gactgattcc agccatcgtg tacgtgtgcc tgtggacggc ctgcctcctc    60
tccacaaacc tcgtggccga ggtggacgag acgtggtcgg ctcgcgagaa cgactcctcg   120
tcgccgccgc cgccgccact gagtcacgag aagcggctga tggactcgct gctgcgccac   180
tacgacgcca gcgtgaggcc cgtcaagaac tcctcggagc ccgtcatcat tcggctgggc   240
atcacgctca cgcagatatt cgacctggac gagaagaatc aagtcctaac aaccatcgtt   300
tggcttgacc aggaatggtt cgacgagtac ctcacttggg acccgttgga gtttggaaac   360
ttcagcaacc tcaggctgcc ctgccacaag atttggctgc tgacatcgt tctctacaac    420 aacgcggacg actacacgcg gggctacttc cagacgcgcg ccatgatcga cccccagggc   480
cgagtgttct ggccgccacc caccaagttt cgcagcacct gcccggtgga cgtaacgtac   540
ttccctttcg acgaccaggt ctgcacaatg aagttcggtt cttggatcta tgacgggcta   600
caagtggaca tccagaaccg acatccgag gttgacctgg tcaattacat gcccaacggc    660
gagtgggagc tgcttgaggc acgcatggtg cgcaacgtgg tctactaccc ttgctgtcca   720
gaccagccgt tcccggacat caccgtggtc ttggtcatga ggcgcaagac gctctactac   780
atgtacaacg tggtcctgcc ctgcatcatg atgtctgtgc tgactctgct cgtcttctgc   840
ctaccgccgg actcgggcga agatcgcg ctcggcgtca cagtgctgct agcattctcc     900
gtgttcatgc tggccatagc ggagaagatg cccgagacat cggagtccat accccttactg  960 ggaatatacc tgacggccgt gatggccatc acgtccatct cggtcgtcat gaccgtgatc  1020
gtcctcaact ccactaccg cggccccagc cggaaagaag tgccagcgtg gctccgccgt   1080
ctcctgctca acaagtcatc ctccagtcgt ggttggttct cgaagccggc gcgccgcaag   1140
accgtcggcg acaatcacgt gcacttctac gacttgccat cgcgcacagc agcctccaag   1200
gaccgctcag acctggacga cgacgtagac ggcagcagaa gacctgcggc cgacgacacc   1260
ttccggctcg tcgtggacag cgtcgtgatc ggcagcgaag accgctacac tcgcggcgag   1320
tacgccgagc actccgcgag caacgagtcc ccgagtcccg tcctccacgg cgacatgtcg   1380
cggaacaatg cctccgggtc ggccaggcac cgccgctgtc gcgctggtgc cgctagtggc   1440
ggatccacta agcgcgtgca ggaagaagtg ctgcggactt tgcggtacct gatggagaaa   1500
cagcagcgcg aggagcacct cacccggact gtgaacgagt ggagacagat ggctctcgtg   1560
atagatcgca ccttgttctg gttctttctg atcatcacag ccgtgtcatc crtctgcttc   1620
ctagtcgtca tacccataca gaggcgggga ctg                               1653
```

<210> SEQ ID NO 8
<211> LENGTH: 1503
<212> TYPE: DNA
<213> ORGANISM: artificial sequence
<220> FEATURE:
<223> OTHER INFORMATION: portion of cDNA based on Rhipicephalus microplus

<400> SEQUENCE: 8

```
cgccccggac gcctgtctgt gccgctgcag ctaggcttct gcgccaacct gctgtggatc     60
gccgtgctgc tcaccgcgcc tcaggactct gaacaaggcg cgcacgagcg gcggcttctg    120
gcagacctgc tggccaacta caacaccctg gagcggcccg tgctcaacga gtcggagccg    180
ctcatcctca gcttcgggct cacactgcag cagatcatag acgtcgacga aaagaatcag    240
ctaattatta caaatatctg gttaacattg gattggatag atgtgaatct acgttggaac    300
ccaaaagact acggcggagt gcaggacctg cgtattccgc caaacaaaat ttggaagcct    360
```

```
gacgtgctca tgtacaacag cgcggacgaa aagttcgacg gcacgtaccc gaccaacgtg      420
gtcgtgcgga gcaacggcag ttgcaactac atccctcctg gcatctttaa gagcacgtgc      480
aagatcgaca ttacgtggtt cccttttgac gatcagaagt gcgacctgaa gttcggctcc      540
tggacctatc acggttatca gctggacctt cgtgtcaaca gtgaggaagg cggggatctg      600
actacctaca ttcccaatgg cgagtgggac ctgataggcg tgccgggagt gcgcaacgtt      660
cgcgagtatg cctgctgtcc ggagccgtac atcgacatca cgtacaccat ccacatccgg      720
cggcgcacgc tctactacgg cttcaacctc atcattccct gcgtgctcat ctcgtccatg      780
actctgctcg gtttcacgct gccccccgac accggagaga ggctcaccct gggtgtaacc      840
attttgctgt ccctgacggt attcatgctc cagctcgccg agaccatgcc tccgacgtcc      900
gatgctgtct ccataatagg aacttatttt gcctgcatca tgatcatggt tgccttttcg      960
gtggtcatga ccgtggtggt cctgaactat catcacagaa atcaagagac gaccgaaatg     1020
cctgctttga ttcgcacggt gttcctggtg tggctcccgt ggcttctgcg catggagcct     1080
ccgggccaga aggcgaacag gcgcagcctc ttcctcaaca gcaagatgaa agagctcgag     1140
ctgaaggagc gctcatcgcg gagtctgctg gccaacgtgc tggacatcga cgacgacttc     1200
cgcacggcca acagcgccgc cgccgccgcc gactgccacg ggtctcggac cccgttcctg     1260
ggcggtggcg gcggggcgtc cacggtgcac gcttgcgtcc actcgtcgcg tgaactgaac     1320
ttgatcttgc gcgagctgcg cttcatcacg agccgcatgc gcaaggacga gcaagagcgg     1380
gaggtcgttg gcgagtggaa gttcgcggcc atggtcgtcg accgctgctg cctcatcatc     1440
ttctccctgt tcaccatcat ctccacctgc gcctgcctct tctcggcgcc ccatctggtc     1500
gcc                                                                   1503

<210> SEQ ID NO 9
<211> LENGTH: 1503
<212> TYPE: DNA
<213> ORGANISM: artificial sequence
<220> FEATURE:
<223> OTHER INFORMATION: portion of cDNA based on Rhipicephalus
      microplus

<400> SEQUENCE: 9
cgccccggac gcctgtctgt gccgctgcag ctaggcttct cgccaacct gctgtggatc        60 gccgtgctgc tcaccgcgcc tcaggactct gaacaaggcg cgcacgagcg gcggcttctg      120
gcagacctgc tggccaacta caacaccctg gagcggcccg tgctcaacga gtcggagccg      180
ctcatcctca gcttcgggct cacactgcag cagatcatag acgtcgacga aaagaatcaa      240
ataataacaa caaacgtgtg gttaaatctg gattggatag atgtgaatct acgttggaac      300
ccaaaagact acggcggagt gcaggacctg cgtattccgc caaacaaaat ttggaagcct      360
gacgtgctca tgtacaacag cgcggacgaa aagttcgacg gcacgtaccc gaccaacgtg      420
gtcgtgcgga gcaacggcag ttgcaactac atccctcctg gcatctttaa gagcacgtgc      480
aagatcgaca ttacgtggtt cccttttgac gatcagaagt gcgacctgaa gttcggctcc      540
tggacctatc acggttatca gctggacctt cgtgtcaaca gtgaggaagg cggggatctg      600
actacctaca ttcccaatgg cgagtgggac ctgataggcg tgccgggagt gcgcaacgtt      660
cgcgagtatg cctgctgtcc ggagccgtac atcgacatca cgtacaccat ccacatccgg      720
cggcgcacgc tctactacgg cttcaacctc atcattccct gcgtgctcat ctcgtccatg      780
actctgctcg gtttcacgct gccccccgac accggagaga ggctcaccct gggtgtaacc      840
```

```
attttgctgt ccctgacggt attcatgctc cagctcgccg agaccatgcc tccgacgtcc    900
gatgctgtct ccataatagg aacttatttt gcctgcatca tgatcatggt tgcctttcg    960
gtggtcatga ccgtggtggt cctgaactat catcacagaa atcaagagac gaccgaaatg   1020
cctgctttga ttcgcacggt gttcctggtg tggctcccgt ggcttctgcg catggagcct   1080
ccgggccaga aggcgaacag gcgcagcctc ttcctcaaca gcaagatgaa agagctcgag   1140
ctgaaggagc gctcatcgcg gagtctgctg gccaacgtgc tggacatcga cgacgacttc   1200
cgcacggcca acagcgccgc cgccgccgcc gactgccacg ggtctcggac cccgttcctg   1260
ggcggtggcg gcggggcgtc cacggtgcac gcttgcgtcc actcgtcgcg tgaactgaac   1320
ttgatcttgc gcgagctgcg cttcatcacg agccgcatgc gcaaggacga gcaagagcgg   1380
gaggtcgttg gcgagtggaa gttcgcggcc atggtcgtcg accgctgctg cctcatcatc   1440
ttctccctgt tcaccatcat ctccacctgc gcctgcctct tctcggcgcc ccatctggtc   1500
gcc                                                                 1503
```

<210> SEQ ID NO 10
<211> LENGTH: 523
<212> TYPE: PRT
<213> ORGANISM: artificial sequence
<220> FEATURE:
<223> OTHER INFORMATION: portion of protein from Rhipicephalus microplus

<400> SEQUENCE: 10

```
Leu Val Ala Glu Val Asp Glu Thr Trp Ser Ala Arg Glu Asn Asp Ser
1               5                   10                  15

Ser Ser Pro Pro Pro Pro Leu Ser His Glu Lys Arg Leu Met Asp
            20                  25                  30

Ser Leu Leu Arg His Tyr Asp Ala Ser Val Arg Pro Val Lys Asn Ser
        35                  40                  45

Ser Glu Pro Val Ile Ile Arg Leu Gly Ile Thr Leu Thr Gln Ile Phe
    50                  55                  60

Asp Leu Asp Glu Lys Asn Gln Val Leu Thr Thr Ile Val Trp Leu Asp
65                  70                  75                  80

Gln Glu Trp Phe Asp Glu Tyr Leu Thr Trp Asp Pro Leu Glu Phe Gly
                85                  90                  95

Asn Phe Ser Asn Leu Arg Leu Pro Cys His Lys Ile Trp Leu Pro Asp
            100                 105                 110

Ile Val Leu Tyr Asn Asn Ala Asp Asp Tyr Thr Arg Gly Tyr Phe Gln
        115                 120                 125

Thr Arg Ala Met Ile Asp Pro Gln Gly Arg Val Phe Trp Pro Pro Pro
    130                 135                 140

Thr Lys Phe Arg Ser Thr Cys Pro Val Asp Val Thr Tyr Phe Pro Phe
145                 150                 155                 160

Asp Asp Gln Val Cys Thr Met Lys Phe Gly Ser Trp Ile Tyr Asp Gly
                165                 170                 175

Leu Gln Val Asp Ile Gln Asn Arg Thr Ser Glu Val Asp Leu Val Asn
            180                 185                 190

Tyr Met Pro Asn Gly Glu Trp Glu Leu Leu Glu Ala Arg Met Val Arg
        195                 200                 205

Asn Val Val Tyr Tyr Pro Cys Cys Pro Asp Gln Pro Phe Pro Asp Ile
    210                 215                 220

Thr Val Val Leu Val Met Arg Arg Lys Thr Leu Tyr Tyr Met Tyr Asn
225                 230                 235                 240
```

```
Val Val Leu Pro Cys Ile Met Met Ser Val Leu Thr Leu Leu Val Phe
            245                 250                 255

Cys Leu Pro Pro Asp Ser Gly Glu Lys Ile Ala Leu Gly Val Thr Val
            260                 265                 270

Leu Leu Ala Phe Ser Val Phe Met Leu Ala Ile Ala Glu Lys Met Pro
            275                 280                 285

Glu Thr Ser Glu Ser Ile Pro Leu Leu Gly Ile Tyr Leu Thr Ala Val
            290                 295                 300

Met Ala Ile Thr Ser Ile Ser Val Val Met Thr Val Ile Val Leu Asn
305                 310                 315                 320

Phe His Tyr Arg Gly Pro Ser Arg Lys Glu Val Pro Ala Trp Leu Arg
            325                 330                 335

Arg Leu Leu Leu Asn Lys Ser Ser Ser Arg Gly Trp Phe Ser Lys
            340                 345                 350

Pro Ala Arg Arg Lys Thr Val Gly Asp Asn His Val His Phe Tyr Asp
            355                 360                 365

Leu Pro Ser Arg Thr Ala Ala Ser Lys Asp Arg Ser Asp Leu Asp Asp
            370                 375                 380

Asp Val Asp Gly Ser Arg Arg Pro Ala Ala Asp Asp Thr Phe Arg Leu
385                 390                 395                 400

Val Val Asp Ser Val Val Ile Gly Ser Glu Asp Arg Tyr Thr Arg Gly
            405                 410                 415

Glu Tyr Ala Glu His Ser Ala Ser Asn Glu Ser Pro Ser Pro Val Leu
            420                 425                 430

His Gly Asp Met Ser Arg Asn Asn Ala Ser Gly Ser Ala Arg His Arg
            435                 440                 445

Arg Cys Arg Ala Gly Ala Ala Ser Gly Gly Ser Thr Lys Arg Val Gln
            450                 455                 460

Glu Glu Val Leu Arg Thr Leu Arg Tyr Leu Met Glu Lys Gln Gln Arg
465                 470                 475                 480

Glu Glu His Leu Thr Arg Thr Val Asn Glu Trp Arg Gln Met Ala Leu
            485                 490                 495

Val Ile Asp Arg Thr Leu Phe Trp Phe Phe Leu Ile Ile Thr Ala Val
            500                 505                 510

Ser Ser Val Cys Phe Leu Val Val Ile Pro Ile
            515                 520

<210> SEQ ID NO 11
<211> LENGTH: 374
<212> TYPE: PRT
<213> ORGANISM: artificial sequence
<220> FEATURE:
<223> OTHER INFORMATION: portion of protein from Rhipicephalus microplus

<400> SEQUENCE: 11

Leu Leu Thr Ala Pro Gln Asp Ser Glu Gln Gly Ala His Glu Arg Arg
1               5                   10                  15

Leu Leu Ala Asp Leu Leu Ala Asn Tyr Asn Thr Leu Glu Arg Pro Val
            20                  25                  30

Leu Asn Glu Ser Glu Pro Leu Ile Leu Ser Phe Gly Leu Thr Leu Gln
            35                  40                  45

Gln Ile Ile Asp Val Asp Glu Lys Asn Gln Leu Ile Ile Thr Asn Ile
            50                  55                  60

Trp Leu Thr Leu Asp Trp Ile Asp Val Asn Leu Arg Trp Asn Pro Lys
65              70                  75                  80
```

-continued

Asp Tyr Gly Gly Val Gln Asp Leu Arg Ile Pro Pro Asn Lys Ile Trp
            85                  90                  95

Lys Pro Asp Val Leu Met Tyr Asn Ser Ala Asp Glu Lys Phe Asp Gly
            100                 105                 110

Thr Tyr Pro Thr Asn Val Val Arg Ser Asn Gly Ser Cys Asn Tyr
        115                 120                 125

Ile Pro Pro Gly Ile Phe Lys Ser Thr Cys Lys Ile Asp Ile Thr Trp
    130                 135                 140

Phe Pro Phe Asp Asp Gln Lys Cys Asp Leu Lys Phe Gly Ser Trp Thr
145                 150                 155                 160

Tyr His Gly Tyr Gln Leu Asp Leu Arg Val Asn Ser Glu Glu Gly Gly
                165                 170                 175

Asp Leu Thr Thr Tyr Ile Pro Asn Gly Glu Trp Asp Leu Ile Gly Val
            180                 185                 190

Pro Gly Val Arg Asn Val Arg Glu Tyr Ala Cys Cys Pro Glu Pro Tyr
        195                 200                 205

Ile Asp Ile Thr Tyr Thr Ile His Ile Arg Arg Thr Leu Tyr Tyr
    210                 215                 220

Gly Phe Asn Leu Ile Ile Pro Cys Val Leu Ile Ser Ser Met Thr Leu
225                 230                 235                 240

Leu Gly Phe Thr Leu Pro Pro Asp Thr Gly Glu Arg Leu Thr Leu Gly
                245                 250                 255

Val Thr Ile Leu Leu Ser Leu Thr Val Phe Met Leu Gln Leu Ala Glu
            260                 265                 270

Thr Met Pro Pro Thr Ser Asp Ala Val Ser Ile Ile Gly Thr Tyr Phe
        275                 280                 285

Ala Cys Ile Met Ile Met Val Ala Phe Ser Val Val Met Thr Val Val
    290                 295                 300

Val Leu Asn Tyr His His Arg Asn Gln Glu Thr Thr Glu Met Pro Ala
305                 310                 315                 320

Leu Ile Arg Thr Val Phe Leu Val Trp Leu Pro Trp Leu Leu Arg Met
                325                 330                 335

Glu Pro Pro Gly Gln Lys Ala Asn Arg Arg Ser Leu Phe Leu Asn Ser
            340                 345                 350

Lys Met Lys Glu Leu Glu Leu Lys Glu Arg Ser Ser Arg Ser Leu Leu
        355                 360                 365

Ala Asn Val Leu Asp Ile
    370

<210> SEQ ID NO 12
<211> LENGTH: 378
<212> TYPE: PRT
<213> ORGANISM: artificial sequence
<220> FEATURE:
<223> OTHER INFORMATION: portion of protein from Rhipicephalus microplus

<400> SEQUENCE: 12

Ile Ala Val Leu Leu Thr Ala Pro Gln Asp Ser Glu Gln Gly Ala His
1               5                   10                  15

Glu Arg Arg Leu Leu Ala Asp Leu Leu Ala Asn Tyr Asn Thr Leu Glu
            20                  25                  30

Arg Pro Val Leu Asn Glu Ser Glu Pro Leu Ile Leu Ser Phe Gly Leu
        35                  40                  45

Thr Leu Gln Gln Ile Ile Asp Val Asp Glu Lys Asn Gln Leu Ile Ile
    50                  55                  60

-continued

```
Thr Asn Ile Trp Leu Thr Leu Asp Trp Ile Asp Val Asn Leu Arg Trp
 65                  70                  75                  80

Asn Pro Lys Asp Tyr Gly Gly Val Gln Asp Leu Arg Ile Pro Pro Asn
                 85                  90                  95

Lys Ile Trp Lys Pro Asp Val Leu Met Tyr Asn Ser Ala Asp Glu Lys
            100                 105                 110

Phe Asp Gly Thr Tyr Pro Thr Asn Val Val Arg Ser Asn Gly Ser
            115                 120                 125

Cys Asn Tyr Ile Pro Pro Gly Ile Phe Lys Ser Thr Cys Lys Ile Asp
130                 135                 140

Ile Thr Trp Phe Pro Phe Asp Asp Gln Lys Cys Asp Leu Lys Phe Gly
145                 150                 155                 160

Ser Trp Thr Tyr His Gly Tyr Gln Leu Asp Leu Arg Val Asn Ser Glu
                165                 170                 175

Glu Gly Gly Asp Leu Thr Thr Tyr Ile Pro Asn Gly Glu Trp Asp Leu
            180                 185                 190

Ile Gly Val Pro Gly Val Arg Asn Val Arg Glu Tyr Ala Cys Cys Pro
            195                 200                 205

Glu Pro Tyr Ile Asp Ile Thr Tyr Thr Ile His Ile Arg Arg Arg Thr
210                 215                 220

Leu Tyr Tyr Gly Phe Asn Leu Ile Ile Pro Cys Val Leu Ile Ser Ser
225                 230                 235                 240

Met Thr Leu Leu Gly Phe Thr Leu Pro Pro Asp Thr Gly Glu Arg Leu
                245                 250                 255

Thr Leu Gly Val Thr Ile Leu Leu Ser Leu Thr Val Phe Met Leu Gln
            260                 265                 270

Leu Ala Glu Thr Met Pro Pro Thr Ser Asp Ala Val Ser Ile Ile Gly
            275                 280                 285

Thr Tyr Phe Ala Cys Ile Met Ile Met Val Ala Phe Ser Val Val Met
290                 295                 300

Thr Val Val Leu Asn Tyr His His Arg Asn Gln Glu Thr Thr Glu
305                 310                 315                 320

Met Pro Ala Leu Ile Arg Thr Val Phe Leu Val Trp Leu Pro Trp Leu
                325                 330                 335

Leu Arg Met Glu Pro Pro Gly Gln Lys Ala Asn Arg Arg Ser Leu Phe
            340                 345                 350

Leu Asn Ser Lys Met Lys Glu Leu Glu Leu Lys Glu Arg Ser Ser Arg
            355                 360                 365

Ser Leu Leu Ala Asn Val Leu Asp Ile Asp
    370                 375
```

<210> SEQ ID NO 13
<211> LENGTH: 374
<212> TYPE: PRT
<213> ORGANISM: artificial sequence
<220> FEATURE:
<223> OTHER INFORMATION: portion of protein from Rhipicephalus microplus

<400> SEQUENCE: 13

```
Leu Leu Thr Ala Pro Gln Asp Ser Glu Gln Gly Ala His Glu Arg Arg
  1               5                  10                  15

Leu Leu Ala Asp Leu Leu Ala Asn Tyr Asn Thr Leu Glu Arg Pro Val
             20                  25                  30

Leu Asn Glu Ser Glu Pro Leu Ile Leu Ser Phe Gly Leu Thr Leu Gln
         35                  40                  45
```

```
Gln Ile Ile Asp Val Asp Glu Lys Asn Gln Ile Ile Thr Thr Asn Val
    50                  55                  60

Trp Leu Asn Leu Asp Trp Ile Asp Val Asn Leu Arg Trp Asn Pro Lys
65                  70                  75                  80

Asp Tyr Gly Gly Val Gln Asp Leu Arg Ile Pro Pro Asn Lys Ile Trp
                    85                  90                  95

Lys Pro Asp Val Leu Met Tyr Asn Ser Ala Asp Glu Lys Phe Asp Gly
                100                 105                 110

Thr Tyr Pro Thr Asn Val Val Arg Ser Asn Gly Ser Cys Asn Tyr
                115                 120                 125

Ile Pro Pro Gly Ile Phe Lys Ser Thr Cys Lys Ile Asp Ile Thr Trp
    130                 135                 140

Phe Pro Phe Asp Asp Gln Lys Cys Asp Leu Lys Phe Gly Ser Trp Thr
145                 150                 155                 160

Tyr His Gly Tyr Gln Leu Asp Leu Arg Val Asn Ser Glu Glu Gly Gly
                165                 170                 175

Asp Leu Thr Thr Tyr Ile Pro Asn Gly Glu Trp Asp Leu Ile Gly Val
                180                 185                 190

Pro Gly Val Arg Asn Val Arg Glu Tyr Ala Cys Cys Pro Glu Pro Tyr
            195                 200                 205

Ile Asp Ile Thr Tyr Thr Ile His Ile Arg Arg Thr Leu Tyr Tyr
    210                 215                 220

Gly Phe Asn Leu Ile Ile Pro Cys Val Leu Ile Ser Ser Met Thr Leu
225                 230                 235                 240

Leu Gly Phe Thr Leu Pro Pro Asp Thr Gly Glu Arg Leu Thr Leu Gly
                245                 250                 255

Val Thr Ile Leu Leu Ser Leu Thr Val Phe Met Leu Gln Leu Ala Glu
                260                 265                 270

Thr Met Pro Pro Thr Ser Asp Ala Val Ser Ile Ile Gly Thr Tyr Phe
            275                 280                 285

Ala Cys Ile Met Ile Met Val Ala Phe Ser Val Val Met Thr Val Val
    290                 295                 300

Val Leu Asn Tyr His His Arg Asn Gln Glu Thr Thr Glu Met Pro Ala
305                 310                 315                 320

Leu Ile Arg Thr Val Phe Leu Val Trp Leu Pro Trp Leu Leu Arg Met
                325                 330                 335

Glu Pro Pro Gly Gln Lys Ala Asn Arg Arg Ser Leu Phe Leu Asn Ser
            340                 345                 350

Lys Met Lys Glu Leu Glu Leu Lys Arg Ser Ser Arg Ser Leu Leu
    355                 360                 365

Ala Asn Val Leu Asp Ile
    370
```

<210> SEQ ID NO 14
<211> LENGTH: 378
<212> TYPE: PRT
<213> ORGANISM: artificial sequence
<220> FEATURE:
<223> OTHER INFORMATION: portion of protein from Rhipicephalus microplus

<400> SEQUENCE: 14

```
Ile Ala Val Leu Leu Thr Ala Pro Gln Asp Ser Glu Gln Gly Ala His
1               5                   10                  15

Glu Arg Arg Leu Leu Ala Asp Leu Leu Ala Asn Tyr Asn Thr Leu Glu
            20                  25                  30
```

Arg Pro Val Leu Asn Glu Ser Glu Pro Leu Ile Leu Ser Phe Gly Leu
    35                  40                  45

Thr Leu Gln Gln Ile Ile Asp Val Asp Glu Lys Asn Gln Ile Ile Thr
 50                  55                  60

Thr Asn Val Trp Leu Asn Leu Asp Trp Ile Asp Val Asn Leu Arg Trp
 65                  70                  75                  80

Asn Pro Lys Asp Tyr Gly Gly Val Gln Asp Leu Arg Ile Pro Pro Asn
                 85                  90                  95

Lys Ile Trp Lys Pro Asp Val Leu Met Tyr Asn Ser Ala Asp Glu Lys
                100                 105                 110

Phe Asp Gly Thr Tyr Pro Thr Asn Val Val Arg Ser Asn Gly Ser
                115                 120                 125

Cys Asn Tyr Ile Pro Pro Gly Ile Phe Lys Ser Thr Cys Lys Ile Asp
    130                 135                 140

Ile Thr Trp Phe Pro Phe Asp Asp Gln Lys Cys Asp Leu Lys Phe Gly
145                 150                 155                 160

Ser Trp Thr Tyr His Gly Tyr Gln Leu Asp Leu Arg Val Asn Ser Glu
                165                 170                 175

Glu Gly Gly Asp Leu Thr Thr Tyr Ile Pro Asn Gly Glu Trp Asp Leu
                180                 185                 190

Ile Gly Val Pro Gly Val Arg Asn Val Arg Glu Tyr Ala Cys Cys Pro
            195                 200                 205

Glu Pro Tyr Ile Asp Ile Thr Tyr Thr Ile His Ile Arg Arg Arg Thr
            210                 215                 220

Leu Tyr Tyr Gly Phe Asn Leu Ile Ile Pro Cys Val Leu Ile Ser Ser
225                 230                 235                 240

Met Thr Leu Leu Gly Phe Thr Leu Pro Pro Asp Thr Gly Glu Arg Leu
                245                 250                 255

Thr Leu Gly Val Thr Ile Leu Ser Leu Thr Val Phe Met Leu Gln
                260                 265                 270

Leu Ala Glu Thr Met Pro Pro Thr Ser Asp Ala Val Ser Ile Ile Gly
            275                 280                 285

Thr Tyr Phe Ala Cys Ile Met Ile Met Val Ala Phe Ser Val Val Met
290                 295                 300

Thr Val Val Leu Asn Tyr His His Arg Asn Gln Glu Thr Thr Glu
305                 310                 315                 320

Met Pro Ala Leu Ile Arg Thr Val Phe Leu Val Trp Leu Pro Trp Leu
                325                 330                 335

Leu Arg Met Glu Pro Pro Gly Gln Lys Ala Asn Arg Arg Ser Leu Phe
            340                 345                 350

Leu Asn Ser Lys Met Lys Glu Leu Glu Leu Lys Glu Arg Ser Ser Arg
            355                 360                 365

Ser Leu Leu Ala Asn Val Leu Asp Ile Asp
    370                 375

<210> SEQ ID NO 15
<211> LENGTH: 1569
<212> TYPE: DNA
<213> ORGANISM: artificial sequence
<220> FEATURE:
<223> OTHER INFORMATION: portion of cDNA based on Rhipicephalus
      microplus

<400> SEQUENCE: 15
ctcgtggccg aggtggacga gacgtggtcg gctcgcgaga acgactcctc gtcgccgccg      60

```
ccgccgccac tgagtcacga gaagcggctg atggactcgc tgctgcgcca ctacgacgcc      120
agcgtgaggc ccgtcaagaa ctcctcggag cccgtcatca ttcggctggg catcacgctc      180
acgcagatat tcgacctgga cgagaagaat caagtcctaa caaccatcgt ttggcttgac      240
caggaatggt tcgacgagta cctcacttgg gacccgttgg agtttggaaa cttcagcaac      300
ctcaggctgc cctgccacaa gatttggctg cctgacatcg ttctctacaa caacgcggac      360
gactacacgc ggggctactt ccagacgcgc gccatgatcg accccagggc cgagtgttc       420 tggccgccac ccaccaagtt tcgcagcacc tgcccggtgg acgtaacgta cttccctttc      480
gacgaccagg tctgcacaat gaagttcggt tcttggatct atgacgggct acaagtggac      540
atccagaacc ggacatccga ggttgacctg gtcaattaca tgcccaacgg cgagtgggag      600
ctgcttgagg cacgcatggt gcgcaacgtg gtctactacc cttgctgtcc agaccagccg      660
ttcccggaca tcaccgtggt cttggtcatg aggcgcaaga cgctctacta catgtacaac      720
gtggtcctgc cctgcatcat gatgtctgtg ctgactctgc tcgtcttctg cctaccgccg      780
gactcgggcg agaagatcgc gctcggcgtc acagtgctgc tagcattctc cgtgttcatg      840
ctggccatag cggagaagat gcccgagaca tcggagtcca tacccttact gggaatatac      900
ctgacggccg tgatggccat cacgtccatc tcggtcgtca tgaccgtgat cgtcctcaac      960
ttccactacc gcggccccag ccggaaagaa gtgccagcgt ggctccgccg tctcctgctc     1020
aacaagtcat cctccagtcg tggttggttc tcgaagccgg cgcgccgcaa gaccgtcggc     1080
gacaatcacg tgcacttcta cgacttgcca tcgcgcacag cagcctccaa ggaccgctca     1140
gacctggacg acgacgtaga cggcagcaga agacctgcgg ccgacgacac cttccggctc     1200
gtcgtggaca cgtcgtgat cggcagcgaa gaccgctaca ctcgcggcga gtacgccgag     1260
cactccgcga gcaacgagtc cccgagtccc gtcctccacg gcgacatgtc gcggaacaat     1320
gcctccgggt cggccaggca ccgccgctgt cgcgctggtg ccgctagtgg cggatccact     1380
aagcgcgtgc aggaagaagt gctgcggact ttgcggtacc tgatggagaa acagcagcgc     1440
gaggagcacc tcacccggac tgtgaacgag tggagacaga tggctctcgt gatagatcgc     1500
accttgttct ggttctttct gatcatcaca gccgtgtcat ccrtctgctt cctagtcgtc     1560
atacccata                                                             1569
```

<210> SEQ ID NO 16
<211> LENGTH: 1122
<212> TYPE: DNA
<213> ORGANISM: artificial sequence
<220> FEATURE:
<223> OTHER INFORMATION: portion of cDNA based on Rhipicephalus microplus

<400> SEQUENCE: 16

```
ctgctcaccg cgcctcagga ctctgaacaa ggcgcgcacg agcggcggct tctggcagac       60
ctgctggcca actacaacac cctggagcgg cccgtgctca acgagtcgga gccgctcatc      120
ctcagcttcg ggctcacact gcagcagatc atagacgtcg acgaaaagaa tcagctaatt      180
attacaaata tctggttaac attggattgg atagatgtga atctacgttg gaacccaaaa      240
gactacggcg gagtgcagga cctgcgtatt ccgccaaaca aaatttggaa gcctgacgtg      300
ctcatgtaca acagcgcgga cgaaaagttc gacggcacgt acccgaccaa cgtggtcgtg      360
cggagcaacg gcagttgcaa ctacatccct cctggcatct ttaagagcac gtgcaagatc      420
gacattacgt ggttcccttt tgacgatcag aagtgcgacc tgaagttcgg ctcctggacc      480
```

```
tatcacggtt atcagctgga ccttcgtgtc aacagtgagg aaggcgggga tctgactacc    540
tacattccca atggcgagtg ggacctgata ggcgtgccgg gagtgcgcaa cgttcgcgag    600
tatgcctgct gtccggagcc gtacatcgac atcacgtaca ccatccacat ccggcggcgc    660 acgtctact acggcttcaa cctcatcatt ccctgcgtgc tcatctcgtc catgactctg    720
ctcggtttca cgctgccccc cgacaccgga gagaggctca ccctgggtgt aaccatttg    780 ctgtccctga cggtattcat gctccagctc gccgagacca tgcctccgac gtccgatgct    840
gtctccataa taggaactta ttttgcctgc atcatgatca tggttgcctt ttcggtggtc    900
atgaccgtgg tggtcctgaa ctatcatcac agaaatcaag acgaccga aatgcctgct    960 ttgattcgca cggtgttcct ggtgtggctc ccgtggcttc tgcgcatgga gcctccgggc    1020
cagaaggcga acaggcgcag cctcttcctc aacagcaaga tgaaagagct cgagctgaag    1080
gagcgctcat cgcggagtct gctggccaac gtgctggaca tc    1122
```

<210> SEQ ID NO 17
<211> LENGTH: 1134
<212> TYPE: DNA
<213> ORGANISM: artificial sequence
<220> FEATURE:
<223> OTHER INFORMATION: portion of cDNA based on Rhipicephalus microplus

<400> SEQUENCE: 17

```
atcgccgtgc tgctcaccgc gcctcaggac tctgaacaag gcgcgcacga gcggcggctt    60
ctggcagacc tgctggccaa ctacaacacc ctggagcggc ccgtgctcaa cgagtcggag    120
ccgctcatcc tcagcttcgg gctcacactg cagcagatca tagacgtcga cgaaaagaat    180
cagctaatta ttacaaatat ctggttaaca ttggattgga tagatgtgaa tctacgttgg    240
aacccaaaag actacggcgg agtgcaggac ctgcgtattc cgccaaacaa aatttggaag    300
cctgacgtgc tcatgtacaa cagcgcggac gaaaagttcg acggcacgta cccgaccaac    360
gtggtcgtgc ggagcaacgg cagttgcaac tacatccctc ctggcatctt aagagcacg    420 tgcaagatcg acattacgtg gttccctttt gacgatcaga agtgcgacct gaagttcggc    480
tcctggacct atcacggtta tcagctggac cttcgtgtca acagtgagga aggcgggat    540 ctgactacct acattcccaa tggcgagtgg gacctgatag gcgtgccggg agtgcgcaac    600
gttcgcgagt atgcctgctg tccggagccg tacatcgaca tcacgtacac catccacatc    660
cggcggcgca cgtctacta cggcttcaac ctcatcattc cctgcgtgct catctcgtcc    720
atgactctgc tcggtttcac gctgccccc gacaccggag agaggctcac cctgggtgta    780
accattttgc tgtccctgac ggtattcatg ctccagctcg ccgagaccat gcctccgacg    840
tccgatgctg tctccataat aggaacttat tttgcctgca tcatgatcat ggttgccttt    900
tcggtggtca tgaccgtggt ggtcctgaac tatcatcaca gaaatcaaga cgaccgaa    960 atgcctgctt tgattcgcac ggtgttcctg gtgtggctcc cgtggcttct gcgcatggag    1020
cctccgggcc agaaggcgaa caggcgcagc ctcttcctca acagcaagat gaaagagctc    1080
gagctgaagg agcgctcatc gcggagtctg ctggccaacg tgctggacat cgac    1134
```

<210> SEQ ID NO 18
<211> LENGTH: 1122
<212> TYPE: DNA
<213> ORGANISM: artificial sequence
<220> FEATURE:
<223> OTHER INFORMATION: portion of cDNA based on Rhipicephalus microplus

<400> SEQUENCE: 18

| | |
|---|---|
| ctgctcaccg cgcctcagga ctctgaacaa ggcgcgcacg agcggcggct tctggcagac | 60 |
| ctgctggcca actacaacac cctggagcgg cccgtgctca acgagtcgga gccgctcatc | 120 |
| ctcagcttcg ggctcacact gcagcagatc atagacgtcg acgaaaagaa tcaaataata | 180 |
| acaacaaacg tgtggttaaa tctggattgg atagatgtga atctacgttg gaacccaaaa | 240 |
| gactacggcg gagtgcagga cctgcgtatt ccgccaaaca aaatttggaa gcctgacgtg | 300 |
| ctcatgtaca acagcgcgga cgaaaagttc gacggcacgt acccgaccaa cgtggtcgtg | 360 |
| cggagcaacg gcagttgcaa ctacatccct cctggcatct taagagcac gtgcaagatc | 420 |
| gacattacgt ggttcccttt tgacgatcag aagtgcgacc tgaagttcgg ctcctggacc | 480 |
| tatcacggtt atcagctgga ccttcgtgtc aacagtgagg aaggcgggga tctgactacc | 540 |
| tacattccca atggcgagtg ggacctgata ggcgtgccgg gagtgcgcaa cgttcgcgag | 600 |
| tatgcctgct gtccggagcc gtacatcgac atcacgtaca ccatccacat ccggcggcgc | 660 |
| acgctctact acggcttcaa cctcatcatt ccctgcgtgc tcatctcgtc catgactctg | 720 |
| ctcggtttca cgctgccccc cgacaccgga gagaggctca ccctgggtgt aaccattttg | 780 |
| ctgtccctga cggtattcat gctccagctc gccgagacca tgcctccgac gtccgatgct | 840 |
| gtctccataa taggaactta ttttgcctgc atcatgatca tggttgcctt ttcggtggtc | 900 |
| atgaccgtgg tggtcctgaa ctatcatcac agaaatcaag agacgaccga aatgcctgct | 960 |
| ttgattcgca cggtgttcct ggtgtggctc ccgtggcttc tgcgcatgga gcctccgggc | 1020 |
| cagaaggcga acaggcgcag cctcttcctc aacagcaaga tgaaagagct cgagctgaag | 1080 |
| gagcgctcat cgcggagtct gctggccaac gtgctggaca tc | 1122 |

<210> SEQ ID NO 19
<211> LENGTH: 1134
<212> TYPE: DNA
<213> ORGANISM: artificial sequence
<220> FEATURE:
<223> OTHER INFORMATION: portion of cDNA based on Rhipicephalus microplus

<400> SEQUENCE: 19

| | |
|---|---|
| atcgccgtgc tgctcaccgc gcctcaggac tctgaacaag gcgcgcacga gcggcggctt | 60 |
| ctggcagacc tgctggccaa ctacaacacc ctggagcggc ccgtgctcaa cgagtcggag | 120 |
| ccgctcatcc tcagcttcgg gctcacactg cagcagatca tagacgtcga cgaaaagaat | 180 |
| caaataataa caacaaacgt gtggttaaat ctggattgga tagatgtgaa tctacgttgg | 240 |
| aacccaaaag actacggcgg agtgcaggac ctgcgtattc cgccaaacaa aatttggaag | 300 |
| cctgacgtgc tcatgtacaa cagcgcggac gaaaagttcg acggcacgta cccgaccaac | 360 |
| gtggtcgtgc ggagcaacgg cagttgcaac tacatccctc ctggcatctt aagagcacg | 420 |
| tgcaagatcg acattacgtg gttccctttt gacgatcaga agtgcgacct gaagttcggc | 480 |
| tcctggacct atcacggtta tcagctggac cttcgtgtca acagtgagga aggcggggat | 540 |
| ctgactacct acattcccaa tggcgagtgg gacctgatag gcgtgccggg agtgcgcaac | 600 |
| gttcgcgagt atgcctgctg tccggagccg tacatcgaca tcacgtacac catccacatc | 660 |
| cggcggcgca cgctctacta cggcttcaac ctcatcattc cctgcgtgct catctcgtcc | 720 |
| atgactctgc tcggtttcac gctgccccc gacaccggag agaggctcac cctgggtgta | 780 |

| | |
|---|---|
| accattttgc tgtccctgac ggtattcatg ctccagctcg ccgagaccat gcctccgacg | 840 |
| tccgatgctg tctccataat aggaacttat tttgcctgca tcatgatcat ggttgccttt | 900 |
| tcggtggtca tgaccgtggt ggtcctgaac tatcatcaca gaaatcaaga gacgaccgaa | 960 |
| atgcctgctt tgattcgcac ggtgttcctg gtgtggctcc cgtggcttct gcgcatggag | 1020 |
| cctccgggcc agaaggcgaa caggcgcagc ctcttcctca acagcaagat gaaagagctc | 1080 |
| gagctgaagg agcgctcatc gcggagtctg ctggccaacg tgctggacat cgac | 1134 |

<210> SEQ ID NO 20
<211> LENGTH: 5185
<212> TYPE: DNA
<213> ORGANISM: Rhipicephalus microplus

<400> SEQUENCE: 20

| | |
|---|---|
| acatggggaa agcccgtccg tcgcctcgtc cgcgaggaca cgcttgccgc gccgggcgcg | 60 |
| tccctactgt gctgcctctt tttcctcctg cagcgcccac atcaccactt cgcctccaac | 120 |
| cctgcaacag agatacgcct cttcgtggag agaacttcta gtcaactcgc cgcacgcaag | 180 |
| ttttcctccc tgtggattgc tgcgctgcgt gaagcgaaac ttacaaagaa agttttcgt | 240 |
| tccccgcgcc tgtggattcc gatcgacgac gctggatctt ttgtagcgaa agttaggaac | 300 |
| attagttttg tcaacgaggc tccctcgaag gcagcatttt tttcttcctt aaaaaagggt | 360 |
| gtatgaggcg cgctacttaa ttttttttttt tgtcttcctg agtcggtctg ggctttccgg | 420 |
| aaattatttg ttcctgcctt gaacagttct tcgagcagtt cataagaagt gtaaaattag | 480 |
| cgccactttc gtaagaggaa caggaacctt aagaaaaaag agatacctgc aagtagagtt | 540 |
| aaagctctct aatctaagca ttcctcccca cagagaaaaa cgcgcagtgt acttgatacg | 600 |
| cgcagtaaac gcctagcaag gtatattgag gggcctgcgt cggcagcgag aagtttacgc | 660 |
| gcggccaacc acgagcttta ctgcgcagaa agaagaaaa ggggacggga ctgcgaaagc | 720 |
| ctaaaagctc aacctaatca agtaaagca ggtcgttcag attgtcattt tgtcgagctg | 780 |
| aagaagcgac ttcgctgcgt actcggcctt aatcgtagga cagaaggagc acccacatct | 840 |
| gacgcagtgg tcgaagggggg agacggtaca ggagacgtgg aagtgaaaac aaaaatcgcg | 900 |
| aaggacaatg tcgagcaagt tgtcttcgtt gtcaaaggcg gtcgcctcgc cgcgaaaacc | 960 |
| cgtagtctgc gtgttgcaga gatggtcgat gttgggcgtc gaaacttgaa caaaaagcag | 1020 |
| gagctggccg tttcaattga acctccacca tgtttcttcg gggactgatt ccagccatcg | 1080 |
| tgtacgtgtg cctgtggacg gcctgcctcc tctccacaaa cctcgtggcc gaggtggacg | 1140 |
| agacgtggtc ggctcgcgag aacgactcct cgtcgccgcc gccgccgcca ctgagtcacg | 1200 |
| agaagcggct gatggactcg ctgctgcgcc actacgacgc cagcgtgagg cccgtcaaga | 1260 |
| actcctcgga gcccgtcatc attcggctgg gcatcacgct cacgcagata ttcgacctgg | 1320 |
| acgagaagaa tcaagtccta caaccatcg tttggcttga ccaggaatgg ttcgacgagt | 1380 |
| acctcacttg ggacccgttg gagtttggaa acttcagcaa cctcaggctg ccctgccaca | 1440 |
| agatttggct gcctgacatc gttctctaca caacgcgga cgactacacg cggggctact | 1500 |
| tccagacgcg cgccatgatc gacccccagg gccgagtgtt ctggccgcca cccaccaagt | 1560 |
| ttcgcagcac ctgcccggtg gacgtaacgt acttcccttt cgacgaccag gtctgcacaa | 1620 |
| tgaagttcgg ttcttggatc tatgacgggc tacaagtgga catccagaac cggacatccg | 1680 |
| aggttgacct ggtcaattac atgcccaacg gcgagtggga gctgcttgag gcacgcatgg | 1740 |
| tgcgcaacgt ggtctactac ccttgctgtc cagaccagcc gttcccggac atcaccgtgg | 1800 |

```
tcttggtcat gaggcgcaag acgctctact acatgtacaa cgtggtcctg ccctgcatca   1860
tgatgtctgt gctgactctg ctcgtcttct gcctaccgcc ggactcgggc gagaagatcg   1920
cgctcggcgt cacagtgctg ctagcattct ccgtgttcat gctggccata gcggagaaga   1980
tgcccgagac atcggagtcc ataccctac tgggaatata cctgacgcc gtgatggcca    2040
tcacgtccat ctcggtcgtc atgaccgtga tcgtcctcaa cttccactac cgcggcccca   2100
gccggaaaga agtgccagcg tggctccgcc gtctcctgct caacaagtca tcctccagtc   2160
gtggttggtt ctcgaagccg gcgcgccgca agaccgtcgg cgacaatcac gtgcacttct   2220
acgacttgcc atcgcgcaca gcagcctcca aggaccgctc agacctggac gacgacgtag   2280
acggcagcag aagacctgcg gccgacgaca ccttccggct cgtcgtggac agcgtcgtga   2340
tcggcagcga agaccgctac actcgcggcg agtacgccga gcactccgcg agcaacgagt   2400
ccccgagtcc cgtcctccac ggcgacatgt cgcggaacaa tgcctccggg tcggccaggc   2460
accgccgctg tcgcgctggt gccgctagtg gcggatccac taagcgcgtg caggaagaag   2520
tgctgcggac tttgcggtac ctgatggaga acagcagcg cgaggagcac ctcacccgga    2580
ctgtgaacga gtggagacag atggctctcg tgatagatcg caccttgttc tggttctttc   2640
tgatcatcac agccgtgtca tccrtctgct tcctagtcgt catacccata cagaggcggg   2700
gactgtgact gtgacttggg cggagttgtg agcaactctg cattgccatg acgtgctaaa   2760
acacttaaag agagaggcag acgggagaga tccgagggat tcatgtgtca ccattttgac   2820
taaactctgg tggtatggag cctgtattcg tttcgcctaa ataattggtt tacaactctc   2880
taaaatacta gcacatcgta ggcgcgctga agtttagtac ttctcaagag taaacgttag   2940
aaggcatctg cagccttttt gatgttagag acaagtgtac acacaatatt gataatccta   3000
gccacgaatt cttgctatgt tcatctcgga gtttgctaaa tattctttaa cagcgctaat   3060
attgtctaat ttctagacaa gttgcatcta ttgggaaaat cagaggtgga attcacaaag   3120
tatgtcactt gttactattc gtgattattg accatcaagc ttacataata tttccagcat   3180
atgtgttggt tgaaacttcc tttaaattct ttaaactaat atgataatga gtaaagaaag   3240
ttataagcca agtttaaatc tcaccgaggt gtatcgtaca aaacaccaat aaaatgctgt   3300
ataattagtt tcgctatcaa atggtaagaa cattattagt ctttgaagat atgcgagtct   3360
tattatgcag tgtacacaca tgcatcacct tgagtgttgt gattttgatt aggcaaaatt   3420
aaaggtcgaa acggtgatcc aagcaattat gtttcgcata atatccttgc gcctcctgtt   3480
ggagtgtttg tatatttttt ctccttggaa acaagcttgc attcgtgcca aaagagccac   3540
gttattacag atgtgcgtcc aagaaaagag tgggcaaatg aagtgtgtcc acggagctta   3600
atgaatgcaa ttattcgact acaataacgt cactttcaca ctcacttctt tgacggattg   3660
cgcgttttaa aaagcgcgat tgttcataat gtcttcgtcg aaaaccgctg tgctatattt   3720
aggtattgtc aggtttgtct tgttagtgt gccctaccat catgtacaaa actggtcgag    3780
aagaattcga ggaggtgcag gcaaaaaaat atatatttct tagtctgcag ccagtttctc   3840
ctatagataa cgaaccacta ctatggtgcc tatgctgttc taaaaatcta acttagcgca   3900
aaccagcact cgcacgttct caagcgtctg gcattacttt attaaggagg gatttcattg   3960
agtgcaatca cgacagctcc atcaccgcga actcaccatg tgtgtgatac aacagaccgt   4020
ttaactgcag tgctacagca taacttgtca taaatgggcc aaaatgagta accaaatatt   4080
aggtataaag ttgcgtagct tttcacgacc actttcgcaa caccacatta agtatatagg   4140
```

```
catgtgcgac acaggcacaa aaatcccggg aacatgactc aattcacagg attcacctct      4200
gaattatttt ttttctttgc atcttagact gcatcttcat tattcaacca tctttaggct      4260
tgcatagaaa tttcccacgt atttcctgcg acggcagtac tgaaagtacg tactaatctt      4320
tagacaagtg ctcagagtaa cacaagcaca tcgttgctca atactacact aatcatagta      4380
tcttccggta gatgtatatc gtgctagtga cttgtccatt gcttgccgct gctgtagtag      4440
taattttacg catccaaagt gcgatcatgt agttgcttgc aaggcacgtg gatgataaaa      4500
tatactacta cagcgatcta cagcgtttgt gtcttgtttt tgttgttgtt acgttgttga      4560
ttggtgtgag cggtcgatga cgtagcattg tcatcacaaa cagcctgttg aacgcgtatg      4620
gcatctttgc gtcgagaata ccagcaaaac tgaaacggag cgtgcatgga gcatttgcga      4680
ccaatttacg acccctattt gtatgtgatt tgattaataa agtctgtgct cagggaagac      4740
agaaatttgg acggcataaa gcagcctcgg gaaccactag caacgcactt aagcgtttgt      4800
tttatagaaa aattttcttc tttcgctata ttgcgatcac ttgttgttgt tgggcctgct      4860
taagttcttt cagatgcacc tatgcacaac cgttcttttg atgcccgagt catatcactg      4920
ctcagaccga aatgcggacg agggcctgag cagcggtgtg acttgagcgc acgatttcgt      4980
atttttgcac agagatattt cctacttaag gcttccttct caaatccgac tgtggatttt      5040
gtgttagagc gcaaaatttg tttgtctcca tgcacgcgag ctgctttagc cttacttgtg      5100
ttttggggcg agaaaatctg tgtagttgtt tgtgcaataa acgaccacta caggaaaaaa      5160
aaaaaaaaaa aaaaaaaaa aaaaa                                            5185

<210> SEQ ID NO 21
<211> LENGTH: 2316
<212> TYPE: DNA
<213> ORGANISM: Rhipicephalus microplus

<400> SEQUENCE: 21
gaagaggccc gcaggcccac cactcgcggc gtaccacgac gcggaccatg cgccccggac        60
gcctgtctgt gccgctgcag ctaggcttct gcgccaacct gctgtggatc gccgtgctgc       120
tcaccgcgcc tcaggactct gaacaaggcg cgcacgagcg gcggcttctg cagacctgc        180
tggccaacta caacaccctg gagcggcccg tgctcaacga gtcggagccg ctcatcctca       240
gcttcgggct cacactgcag cagatcatag acgtcgacga aaagaatcag ctaattatta       300
caaatatctg gttaacattg gattggatag atgtgaatct acgttggaac ccaaaagact       360
acggcggagt gcaggacctg cgtattccgc caaacaaaat ttggaagcct gacgtgctca       420
tgtacaacag cgcggacgaa aagttcgacg gcacgtaccc gaccaacgtg gtcgtgcgga       480
gcaacggcag ttgcaactac atccctcctg gcatctttaa gagcacgtgc aagatcgaca       540
ttacgtggtt ccctttgac gatcagaagt gcgacctgaa gttcggctcc tggacctatc       600
acggttatca gctggacctt cgtgtcaaca gtgaggaagg cggggatctg actacctaca       660
ttcccaatgg cgagtgggac ctgataggcg tgccggagtc gcgcaacgtt cgcgagtatg       720
cctgctgtcc ggagccgtac atcgacatca cgtacaccat ccacatccgg cggcgcacgc       780
tctactacgg cttcaacctc atcattccct gcgtgctcat ctcgtccatg actctgctcg       840
gtttcacgct gccccccgac accggagaga ggctcaccct gggtgtaacc atttttgctgt      900
ccctgacggt attcatgctc cagctcgccg agaccatgcc tccgacgtcc gatgctgtct       960
ccataatagg aacttatttt gcctgcatca tgatcatggt tgccttttcg gtggtcatga      1020
ccgtggtggt cctgaactat catcacagaa atcaagagac gaccgaaatg cctgctttga      1080
```

-continued

```
ttcgcacggt gttcctggtg tggctcccgt ggcttctgcg catggagcct ccgggccaga    1140
aggcgaacag gcgcagcctc ttcctcaaca gcaagatgaa agagctcgag ctgaaggagc    1200
gctcatcgcg gagtctgctg gccaacgtgc tggacatcga cgacgacttc cgcacggcca    1260
acagcgccgc cgccgccgcc gactgccacg ggtctcggac cccgttcctg ggcggtggcg    1320
gcggggcgtc cacggtgcac gcttgcgtcc actcgtcgcg tgaactgaac ttgatcttgc    1380
gcgagctgcg cttcatcacg agccgcatgc gcaaggacga gcaagagcgg gaggtcgttg    1440
gcgagtggaa gttcgcggcc atggtcgtcg accgctgctg cctcatcatc ttctccctgt    1500
tcaccatcat ctccacctgc gcctgcctct tctcggcgcc ccatctggtc gcctagcgca    1560
ccctgctyct aggacagcac wttaaccgcc accagcttcc tccaccggcg gccttcctct    1620
cggagagctt gttcgctacg ttcttttgcg caagccctgc ttgttagagc gcggcttcyg    1680
agattgattg ctggagccaa tctcgaaggc cacaatctca cagcgcgggc tcgtgtgcga    1740
gaacgtggct cgtgaagagt tccaggtgac gcccttgttg caacayeccg tgaagtcctg    1800 tccacttccc cacgccatca cgtgcgaaga gatgcagcgc gaaacacgta ygacgcgaag    1860
acttcgtacc gcactgaccc ttactgtggg gaggaggaag acacgtggag gtcgcaggag    1920
ctagtttttt tttaagtctc aactcatgtg ccaatcatga gccgccactt gtgcgaaagc    1980
gttggaccat ctcggaggat ctggtagcac cgtccgaagc tggtgccttg gccgtcgctt    2040
tcattctata taggataaaa taacttcatg tatggctgcc aaactgtttg aagggtcaag    2100
cggacttatc aaccgagccc aacgaaggaa gtaaagcacc gggtcttccc tctacgagct    2160
tcgtgatcgt gagatgcccg ccatgatgcg acgccactyg ttacttgctt gaccaccgtc    2220
atggacggct cgtcggagta ggataagcca cgcrcgcaac gtcatcttgc cagtcctttc    2280
tttcgtcggt gaatggtgcg tatgagtaaa aaaaaa                              2316
```